US007183401B1

(12) United States Patent
Yu et al.

(10) Patent No.: US 7,183,401 B1
(45) Date of Patent: Feb. 27, 2007

(54) NOEY2 GENE COMPOSITIONS AND METHODS OF USE

(75) Inventors: Yinhua Yu, Pearland, TX (US); Fengji Xu, Houston, TX (US); Robert C. Bast, Jr., Houston, TX (US)

(73) Assignee: Board of Regents, the University of Texas System, Austin, TX (US)

( * ) Notice: Subject to any disclaimer, the term of this patent is extended or adjusted under 35 U.S.C. 154(b) by 0 days.

(21) Appl. No.: 10/166,325

(22) Filed: Mar. 20, 1998

Related U.S. Application Data

(60) Provisional application No. 60/071,263, filed on Jan. 13, 1998, provisional application No. 60/041,580, filed on Mar. 21, 1997.

(51) Int. Cl.
*C07H 21/04* (2006.01)
*C12N 15/00* (2006.01)
*C12N 5/00* (2006.01)

(52) U.S. Cl. .................. 536/23.5; 435/320.1; 435/325

(58) Field of Classification Search ............... 536/23.1, 536/23.5; 435/320.1, 325, 69.1
See application file for complete search history.

(56) References Cited

U.S. PATENT DOCUMENTS 6,043,088 A * 3/2000 Bookstein et al. .......... 435/366

OTHER PUBLICATIONS

Albanese et al., "Transforming p21$^{ras}$ mutants and c-Ets-2 activate the cyclin D1 promoter through distinguishable regions," *J. Biol. Chem.*, 270:23589-23597, 1995.
Bast et al., "A radioimmunoassay using a monoclonal antibody to monitor the course of epithelial ovarian cancer," *New Engl. J. Med.*, 309:883-887, 1983.
Bast et al., "Malignant transformation of ovarian epithelium," *J. Natl. Cancer Inst.*, 84:556-558, 1992.
Bast et al., "Reactivity of a monoclonal antibody with human ovarian carcinoma," *J. Clin. Invest.*, 68:1331-1337, 1981.
Berchuck et al., "Epidermal growth factor receptor expression in normal ovarian epithelium and ovarian cancer. I. Correlation of receptor expression with prognostic factors in patients with ovarian cancer," *Am. J. Obstet. Gynecol.*, 164:669-674, 1991.
Berchuck et al., "Overexpression of HER-2/neu is associated with poor survival in advanced epithelial ovarian cancer," *Cancer Res.*, 50:4087-4091, 1990.
Berchuck et al., "Regulation of growth of normal ovarian epithelial cells and ovarian cancer cell lines by transforming growth factor-β," *Am. J. Obstet. Gynecol.*, 166:676-684, 1992.
Berchuck et al., "The p53 tumor suppressor gene frequently is altered in gynecologic cancers," *Am. J. Obstet. Gynecol.*, 170:246-252, 1994.
Feig et al., "Somatic activation of RasK gene in a human ovarian carcinoma," *Science*, 223:698-700, 1984.
Havrilesky et al., "Regulation of apoptosis in normal and malignant ovarian epithelial cells by transforming growth factor-β" *Cancer Res.*, 55:944-948, 1995.
Hoggard et al., "Allelic imbalance on chromosome 1 in human breast cancer. II. Microsatellite repeat analysis," *Genes, Chromosome Cancer*, 12:24-31, 1995.
Hurteau et al., "Transforming growth factor-β inhibits proliferation of human ovarian cancer cells obtained from ascites," *Cancer*, 74:93-99, 1994.
Jacobs et al., "A deletion unit on chromosome 17q in epithelial ovarian tumors distal to the familial breast/ovarian cancer locus," *Cancer Res.*, 53:1218-1221, 1993.
Jacobs et al., "Clonal origin of epithelial ovarian cancer: Analysis by loss of heterozygosity, p53 mutation and X chromosome inactivation," *J. Natl. Cancer Inst.*, 84:1793-1798, 1992.
Kacinski et al., "Neu protein overexpression in benign, borderline, and malignant ovarian neoplasms," *Gynecol. Oncol.*, 44:245-253, 1992.
Karlan et al., "Secreted ovarian stromal substance inhibits ovarian epithelial cell proliferation," *Gyn. Onc*, 59(1):67-74, 1995.
Kitayama et al., "A Ras-related gene with transformation suppressor activity," *Cell*, 56:77-84, 1989.
Kohler et al., "Spectrum of mutation and frequency of allelic deletion of the p53 gene in ovarian cancer," *J. Natl. Cancer Inst.*, 85:1513-1519, 1993.
Li et al., "Advanced ovarian carcinoma: molecular evidence of unifocal origin," *Gyn. Onc.*, 51(1):21-25, 1993.
Lidor et al., "Constitutive production of macrophage colony stimulating factor and interleukin-6 by human ovarian surface epithelial cells," *Exp. Cell Res.*, 207:332-339, 1993.
Lidor et al., "Synergistic cytotoxicity of different alkylating agents for epithelial ovarian cancer," *Int. J. Cancer*, 49(5):704-710, 1991.
Loupart et al., "Allelic imbalance on chromosome 1 in human breast cancer. 1. Ministellite and RFLP analysis," *Genes Chromosomes Cancer*, 12:16-23, 1995.
Lynch et al., "Overview of natural history, pathology, molecular genetics and management of HNPCC (Lynch Syndrome)," *Int. J. Cancer*, 69(1):38-43, 1996.
Malkin et al., "Germ line p53 mutations in a familial syndrome of breast cancer, sarcomas, and other neoplasms," *Science*, 250:1233-1238, 1990.

(Continued)

*Primary Examiner*—Gary B. Nickol
(74) *Attorney, Agent, or Firm*—Fulbright & Jaworski L.L.P.

(57) ABSTRACT

Disclosed are compositions and methods comprising a novel tumor suppressor gene, designated NOEY2, that is expressed in normal ovarian and breast surface epithelial cells but consistently absent or down-regulated in ovarian and breast cancer cells. Disclosed are polynucleotide compositions comprising a NOEY2 gene from mammalian sources, and polypeptides encoded by these nucleic acid sequences. Also disclosed are methods for preparing NOEY2 polypeptides, transformed host cells, and antibodies reactive with NOEY2 polypeptides. In certain embodiments, the invention describes methods for diagnosing and treating cancers, as well as methods for identifying NOEY2-related polynucleotide and polypeptide compositions.

23 Claims, 11 Drawing Sheets

OTHER PUBLICATIONS

Figure 3A:
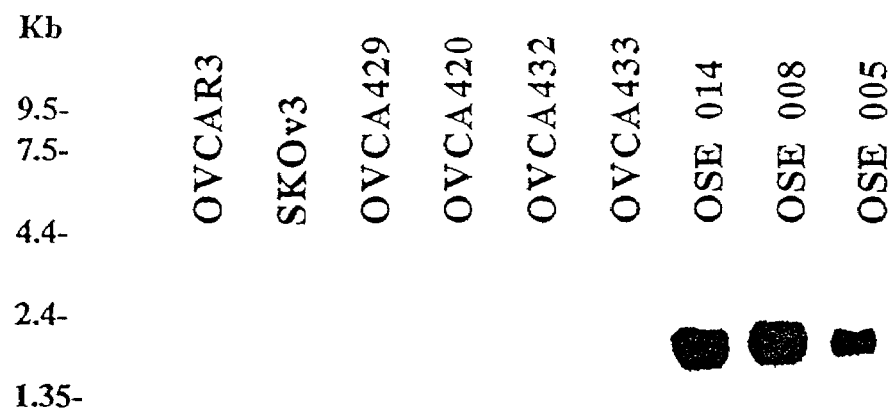

Miki et al., "A strong candidate for the breast and ovarian cancer susceptibility gene BRCA1," *Science*, 266:66-71, 1994.

Mok et al., "Unifocal origin of advanced human epithelial ovarian cancers," *Cancer Res.*, 52:5119-5122, 1992.

Morishige et al., "Involvement of transforming growth factor alpha/ epidermal growth factor receptor autocrine growth mechanism in ovarian cancer cell line in vitro," *Cancer Res.*, 51(21):5951-5955, 1991.

Moser et al., "Secretion of extracellular matrix-degrading proteinases is increased in epithelial ovarian carcinomas," *Int J. Cancer*, 56:552-559, 1994.

Nagai et al., "Detection and cloning of a common region of loss of heterozygosity at chromosome 1p in breast cancer," *Cancer Res.*, 55:1752-1757, 1995.

Rodriguez et al., "Epidermal growth factor receptor expression in normal ovarian epithelium and ovarian cancer. II. Relationship between receptor expression and response to epidermal growth factor" *Am. J. Obstet. Gynecol.*, 164:745-750, 1991.

Rubin et al., "Prognostic significance of HER-2/neu expression in advanced ovarian cancer," *Am. J. Obstet. Gynecol.*, 168:162-169, 1993.

Shultz et al., "Mutations at the murine motheaten locus are within the hematopoietic cell protein-tyrosine phosphatase (Hcph) gene," *Cell*, 73(7):1445-1454, 1993.

Stromberg et al., "Transforming growth factor-alpha acts as an autocrine growth factor in ovarian carcinoma cell lines," *Cancer Res.*, 52(2):341-347, 1992.

Wiener et al., "Overexpression of the tyrosine phosphatase PTP1B is associated with human ovarian carcinomas," *Am. J. Obstet. Gynecol.*, 170:1177-1183, 1994.

Wiener et al., "Transfection of human ovarian cancer cells with the HER-2/*neu* receptor tyrosine kinase induces a selective increase in PTP-H1, PTP-1B, and PTP- expression," *Gynecol. Oncol.*, 61:223-240, 1996.

Wooster et al., "Localization of a breast cancer susceptibility gene, BRCA2, to chromosome 13q12-13," *Science*, 265:2088-2090, 1994.

Worsley et al., "Overexpression of cyclin D1 in epithelial ovarian cancers," *Gynecol. Oncol.*, 64:189-195, 1997.

Wu et al., "Stimulation of ovarian tumor cell proliferation with monocyte products including interleukin-1, interleukin-6, and tumor necrosis factor-alpha," *Am. J. Obstet. Gynecol.*, 166:997-1007, 1992.

Xu et al., "Development of two new monoclonal antibodies reactive to a surface antigen present on human ovarian epithelial cancer cells," *Cancer Res.*, 51:4012-4019, 1991.

Xu et al., "Heregulin and anti-p185c-$erb^{B-2}$ antibodies inhibit proliferation, increase invasiveness and enhance tyrosine autophosphorylation of breast cancer cells that overexpress p185c-$erb^{B-2}$:Increased invasiveness may contribute to poor prognosis," *Clin. Cancer Res.*, 3:1629-1634, 1997.

Xu et al., "Increased serum levels of macrophage colony-stimulating factor in ovarian cancer," *Am. J. Obstet. Gynecol.*, 165:1356-1362, 1991.

Xu et al., "The outcome of Heregulin-induced activation of ovarian cancer cells depends on the relative levels of HER-2 and HER-3 expression," *Clin. Cancer Res.*, 5:3653-3660, 1999.

Yu et al., "Expression of a murine cytomegalovirus early and late protein in latently infected mice," *J. Infectious Diseases*, 172:371-379, 1995.

Yu et al., "Liposome-mediated *in vivo* E1A gene transfer suppressed dissemination of ovarian cancer cells that overexpress HER-2/neu," *Oncogene*, 11(7):1383-1388, 1995b.

\* cited by examiner

```
         10        20        30        40        50        60
CGGGGTGTCCAGTTGGTTGCCGCGGCAGTCTCTCCGAGCAGCGCATTTGTCTTCTAGGCT
         70        80        90       100       110       120
GCTTGGTTCGTGCCTCCGAGAAAGGGGTCTCCTGCTGCCAGCTAAGTGTGGGAGAACTTG
        130       140       150       160       170
TGCACGTATCTCCCCTCCGAATCCCAACGATG GGT AAC GCC AGC TTT GGC TCC AAG
                                 Met Gly Asn Ala Ser Phe Gly Ser Lys
        180       190       200       210       220       230
GAA CAG AAG CTG CTG AAG CGG TTG CGG CTT CTG CCC GCC CTG CTT ATC CTC CGC
Glu Gln Lys Leu Leu Lys Arg Leu Arg Leu Leu Pro Ala Leu Leu Ile Leu Arg
           240       250       260       270       280
GCC TTC AAG CCC CAC AGG AAG ATC AGA GAT TAC CGC GTC GTG GTA GTC GGC ACC
Ala Phe Lys Pro His Arg Lys Ile Arg Asp Tyr Arg Val Val Val Val Gly Thr
          290       300       310       320       330
GCT GGT GTG GGG AAA AGT ACG CTG CTG CAC AAG TGG GCG AGC GGC AAC TTC CGT
a Gly Val Gly Lys Ser Thr Leu Leu His Lys Trp Ala Ser Gly Asn Phe Arg
           350       360       370       380       390
AT GAG TAC CTG CCG ACC ATT GAA AAT ACC TAC TGC CAG TTG CTG GCT GCA GCC
is Glu Tyr Leu Pro Thr Ile Glu Asn Thr Tyr Cys Gln Leu Leu Ala Ala Ala
          400       410       420       430       440
CG GTG TGC TTT CCC TGC ACA TCA CCG ACA GCA AGA GTG GCG ACG GCA ACC GCT
r Val Cys Phe Pro Cys Thr Ser Pro Thr Ala Arg Val Ala Thr Ala Thr Ala
           450       460       470       480       490       500
TG CAG CGC CAC GTT ATA GCC CGG GGC CAC GCC TTC GTC CTG GTC TAC TCA GTC
u Gln Arg His Val Ile Ala Arg Gly His Ala Phe Val Leu Val Tyr Ser Val
          510       520       530       540       550
ACC AAG AAG GAA ACC CTG GAA GAG CTG AAG GCC TTC TAT GAG CTG ATC TGC AAG
Thr Lys Lys Glu Thr Leu Glu Glu Leu Lys Ala Phe Tyr Glu Leu Ile Cys Lys
        560       570       580       590       600
ATC AAA GGT AAC AAC CTG CAT AAG TTC CCC ATC GTG CTG GTG GGC AAT AAA AGT
Ile Lys Gly Asn Asn Leu His Lys Phe Pro Ile Val Leu Val Gly Asn Lys Ser
610       620       630       640       650       660
GAT GAC ACC CAC CGG GAG GTG GCC CTG AAT GAT GGT GCC ACC TGT GCG ATG GAG
Asp Asp Thr His Arg Glu Val Ala Leu Asn Asp Gly Ala Thr Cys Ala Met Glu
        670       680       690       700       710
TGG AAT TGC GCC TTC ATG GAG ATT TCA GCC AAG ACC GAT GTG AAT GTG CAG GAG
Trp Asn Cys Ala Phe Met Glu Ile Ser Ala Lys Thr Asp Val Asn Val Gln Glu
       ·720       730       740       750       760       770
CTG TTC CAC ATG CTG CTG AAT TAC AAG AAA AAG CCC ACC ACC GGC CTC CAG GAG
Leu Phe His Met Leu Leu Asn Tyr Lys Lys Lys Pro Thr Thr Gly Leu Gln Glu
```

FIG. 1A

FIG. 1B

```
          780         790         800              810         820
CCC GAG AAG AAA TCC CAG ATG CCC AAC ACC ACT GAG AAG CTG CTT GAC AAG TGC
Pro Glu Lys Lys Ser Gln Met Pro Asn Thr Thr Glu Lys Leu Leu Asp Lys Cys
      830           840         850         860         870         880
ATA ATC ATG TGAGCCCTGGGCCTTAAGAGCCAGCTCTTCCTATCCTGTAGCGTGTAGAAA
Ile Ile Met *
          890         900         910         920         930         940
ACGTGGACTCATTTCACTATGTTACATGTACATGGTTGATTTTGTGCTGTTGTTTGGACTGTA
      950         960         970         980         990         1000
ACATCCATGTTGTCAATACGTATACCTTGTAAGTGGATAACTTTTCTTTTTCCCAGGCCAGA
  1010        1020        1030        1040        1050        1060        1070
GAATTCAAATTGTTAAAACATTGGCATTTGAAGAGGAGAACAAAATGTAGCATGATGTATT
      1080        1090        1100        1110        1120        1130
TAAAGTAAGGCCTTTAGTAATGAATGTAATGAGAGAAAATGTTTTGAAAAGAACAAAACA
      1140        1150        1160        1170        1180        1190
TCAAAATGAATAGAAAGAAAAATTGGAAGGCGTCCTTTTGGTAACCCGATTATTGTGTATT
      1200        1210        1220        1230        1240        1250
ACCTTTAAATATTTCACATCCTGTAAGTGCTTAATCATATCTTTTAATTGTGTATTTAAGAAA
      1260        1270        1280        1290        1300        1310
AGTGTTTTCACAACAAAAGCTTTTGATAAATTGCTGCGTGACATATACTAAATAAAAAAAT
      1320        1330        1340        1350        1360        1370
GAATATGTTGATCATTAGGGGTGTGGGAGCAGAGAAAATTGTGAAAGTGACTCTCACTAAA
      1380        1390        1400        1410        1420        1430
GATGTTAGTAGTTTCTCATGTCATTTAAAAATGTTTGAGTATTCTGCATAGCAGTTTGTAAA
  1440        1450        1460        1470        1480        1490
AGTGTAACAGCTTATTGACTTAATAAAGCTTTTCCTGCATGCAAAAAAAAAAAA
```

```
H-Ras    MTEYKLVVVGAGGVGKSALTIQLIQ
Rap2     MREYKVVVLGSGGVGKSALTVQFVT
Rap1A    MREYKIVVLGSGGVGKSALTVQFVQ
Rap1B    MREYKIVVLGSGGVGKSALTVQFVQ
NOEY2    IRDYRVVVVGTAGVGKSTLLHKWAS

H-Ras    NHFVDEYDPTIEDSYRKQVVIDGET
Rap2     GTFIEKYDPTIEDFYRKEIEVDSSP
Rap1A    GIFVEKYDPTIEDSYRKQVEVDCQQ
Rap1B    GIFVEKYDPTIEDSYRKQVEVDAQQ
NOEY2    GNFRHEYLPTIENTYCQLLAAATVC

H-Ras    CLLDILDTAGQEEYSAMRDQYMRTG
Rap2     SVLEILDTAGTEQFASMRDLYIKNG
Rap1A    CMLEILDTAGTEQFTAMRDLYMKNG
Rap1B    CMLEILDTAGTEQFTAMRDLYMKNG
NOEY2    FPCTISPTARVATATALQRHVIARG

H-Ras    EGFLCVFAINNTKSFEDIHQYREQI
Rap2     QGFILVYSLVNQQSFQDIKPMRDQI
Rap1A    QGFALVYSITAQSTFNDLQDLREQI
Rap1B    QGFALVYSITAQSTFNDLQDLREQI
NOEY2    HAFVLVYSVTKKETLEELKAFYELI

H-Ras    KRVKDSDDVPMVLVGNK........
Rap2     IRVKRYEKVPVILVGNK........
Rap1A    LRVKDTEDVPNILVGNK........
Rap1B    LRVKDTDDVPMILVGNK........
NOEY2    CKIKNLHKFPIVLVGNK........

H-Ras    SGPGCMSCKCVLS  (SEQ ID NO:6)
Rap2     DKDDPCCSACNIQ  (SEQ ID NO:7)
Rap1A    EKKKPKKKSCLLL  (SEQ ID NO:8)
Rap1B    PGKARKKSSCQLL  (SEQ ID NO:9)
NOEY2    NTTEKLLDKCIIM  (SEQ ID NO:10)
```

FIG. 2

FIG. 4A
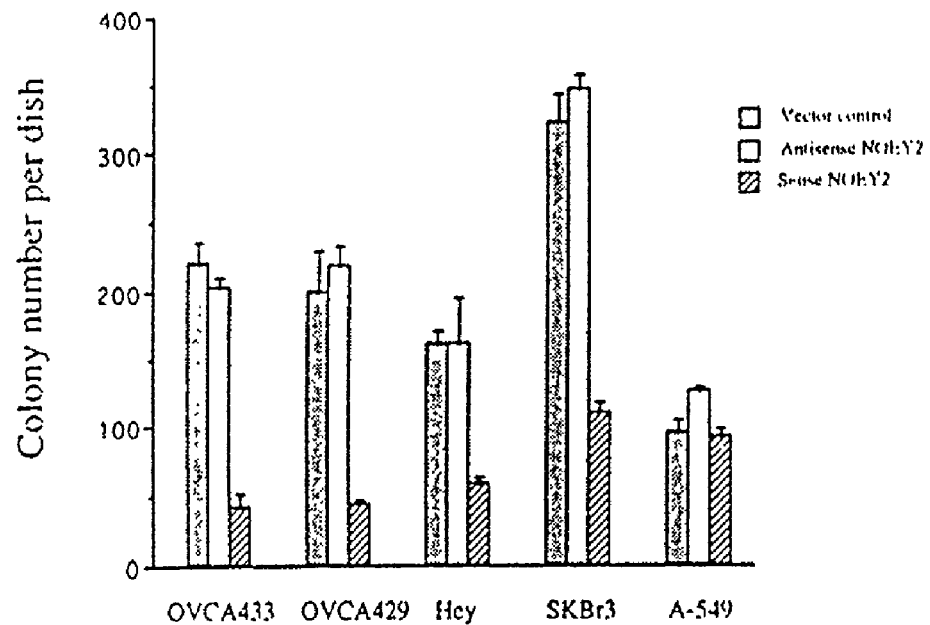
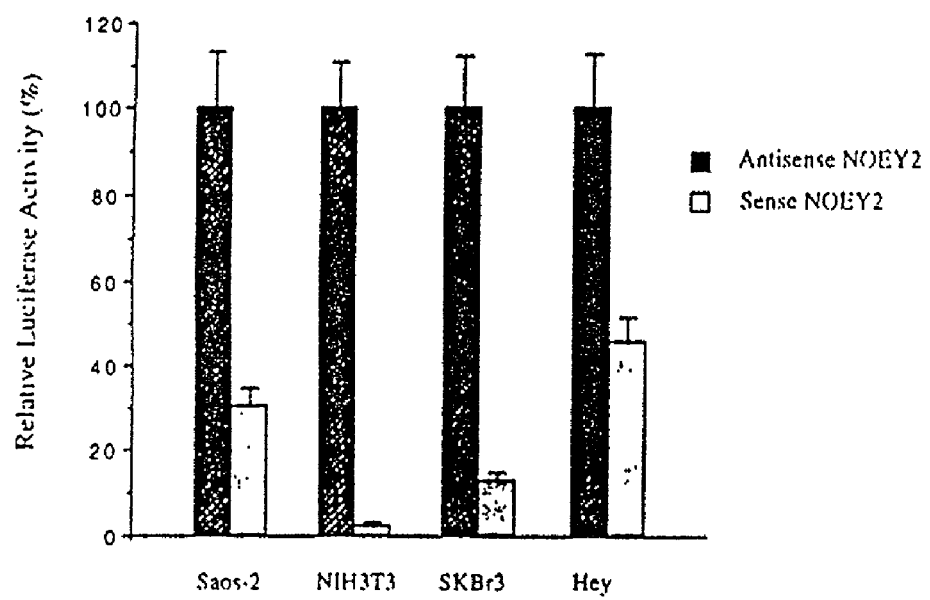
FIG. 4B

FIG. 6A
FIG. 6B
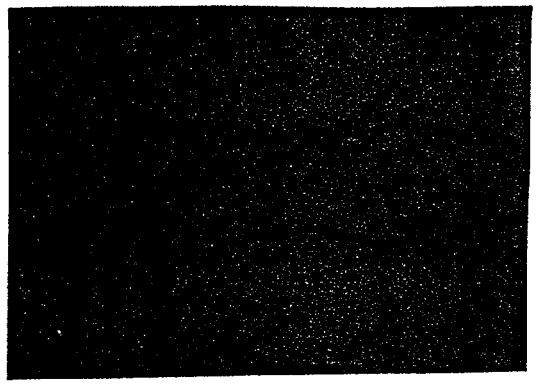
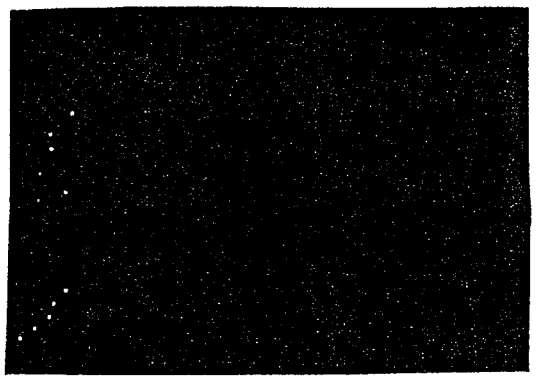
FIG. 6C
FIG. 6D
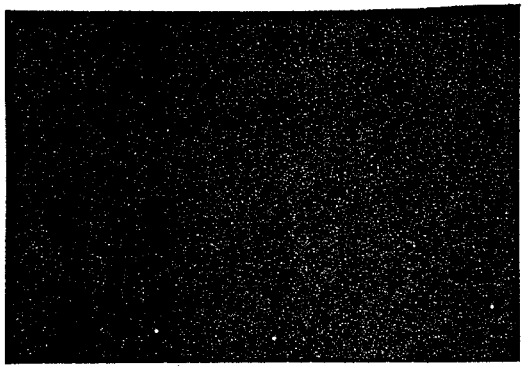
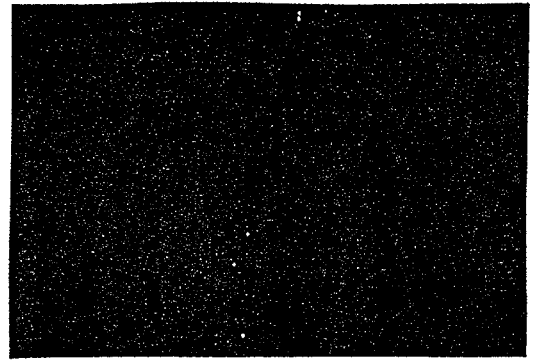

SEQUENCE LISTING

```
<160> NUMBER OF SEQ ID NOS: 10

<210> SEQ ID NO 1
<211> LENGTH: 1481
<212> TYPE: DNA
<213> ORGANISM: Artificial Sequence
<220> FEATURE:
<223> OTHER INFORMATION: Description of Artificial Sequence:  Synthetic
      Primer
<220> FEATURE:
<221> NAME/KEY: CDS
<222> LOCATION: (150)..(833)

<400> SEQUENCE: 1
cggggtgtcc agttggttgc cgcggcagtc tctccgagca gcgcatttgt cttctaggct      60
gcttggttcg tgcctccgag aaagggggtct cctgctgcca gctaagtgtg ggagaacttg     120
tgcacgtatc tcccctccga atcccaacg atg ggt aac gcc agc ttt ggc tcc       173
                                Met Gly Asn Ala Ser Phe Gly Ser
                                 1               5 aag gaa cag aag ctg ctg aag cgg ttg cgg ctt ctg ccc gcc ctg ctt       221
Lys Glu Gln Lys Leu Leu Lys Arg Leu Arg Leu Leu Pro Ala Leu Leu
     10              15                  20 atc ctc cgc gcc ttc aag ccc cac agg aag atc aga gat tac cgc gtc       269
Ile Leu Arg Ala Phe Lys Pro His Arg Lys Ile Arg Asp Tyr Arg Val
 25                  30                  35                  40 gtg gta gtc ggc acc gct ggt gtg ggg aaa agt acg ctg ctg cac aag       317
Val Val Val Gly Thr Ala Gly Val Gly Lys Ser Thr Leu Leu His Lys
                     45                  50                  55 tgg gcg agc ggc aac ttc cgt cat gag tac ctg ccg acc att gaa aat       365
Trp Ala Ser Gly Asn Phe Arg His Glu Tyr Leu Pro Thr Ile Glu Asn
                 60                  65                  70 acc tac tgc cag ttg ctg gct gca gcc acg gtg tgc ttt ccc tgc aca       413
Thr Tyr Cys Gln Leu Leu Ala Ala Thr Val Cys Phe Pro Cys Thr
             75                  80                  85 tca ccg aca gca aga gtg gcg acg gca acc gct ctg cag cgc cac gtt       461
Ser Pro Thr Ala Arg Val Ala Thr Ala Thr Ala Leu Gln Arg His Val
         90                  95                 100 ata gcc cgg ggc cac gcc ttc gtc ctg gtc tac tca gtc acc aag aag       509
Ile Ala Arg Gly His Ala Phe Val Leu Val Tyr Ser Val Thr Lys Lys
105                 110                 115                 120
```

```
gaa acc ctg gaa gag ctg aag gcc ttc tat gag ctg atc tgc aag atc      557
Glu Thr Leu Glu Glu Leu Lys Ala Phe Tyr Glu Leu Ile Cys Lys Ile
            125                 130                 135 aaa ggt aac aac ctg cat aag ttc ccc atc gtg ctg gtg ggc aat aaa      605
Lys Gly Asn Asn Leu His Lys Phe Pro Ile Val Leu Val Gly Asn Lys
            140                 145                 150 agt gat gac acc cac cgg gag gtg gcc ctg aat gat ggt gcc acc tgt      653
Ser Asp Asp Thr His Arg Glu Val Ala Leu Asn Asp Gly Ala Thr Cys
            155                 160                 165 gcg atg gag tgg aat tgc gcc ttc atg gag att tca gcc aag acc gat      701
Ala Met Glu Trp Asn Cys Ala Phe Met Glu Ile Ser Ala Lys Thr Asp
            170                 175                 180 gtg aat gtg cag gag ctg ttc cac atg ctg ctg aat tac aag aaa aag      749
Val Asn Val Gln Glu Leu Phe His Met Leu Leu Asn Tyr Lys Lys Lys
185                 190                 195                 200 ccc acc acc ggc ctc cag gag ccc gag aag aaa tcc cag atg ccc aac      797
Pro Thr Thr Gly Leu Gln Glu Pro Glu Lys Lys Ser Gln Met Pro Asn
            205                 210                 215 acc act gag aag ctg ctt gac aag tgc ata atc atg tgagccctgg           843
Thr Thr Glu Lys Leu Leu Asp Lys Cys Ile Ile Met
            220                 225 gccttaagag ccagctcttc ctatcctgta gcgtgtagaa aacgtggact catttcacta    903
tgttacatgt acatggttga ttttgtgctg ttgtttggac tgtaacatcc atgttgtcaa    963
tacgtatacc ttgtaagtgg ataactttc tttttcccag gccagagaat tcaaattgtt    1023
aaaacattgg catttgaaga ggagaacaaa atgtagcatg atgtatttaa agtaaggcct   1083
ttagtaatga atgtaatgag agaaaatgtt ttgaaaagaa caaaacatca aaatgaatag   1143
aaagaaaaat tggaaggcgt cctttttggta acccgattat tgtgtattac ctttaaatat  1203
ttcacatcct gtaagtgctt aatcatatct tttaattgtg tatttaagaa aagtgttttc   1263
acaacaaaag cttttgataa attgctgcgt gacatatact aaataaaaaa atgaatatgt   1323
tgatcattag gggtgtggga gcagagaaaa ttgtgaaagt gactctcact aaagatgtta   1383
gtagtttctc atgtcattta aaaatgtttg agtattctgc atagcagttt gtaaaagtgt   1443
aacagcttat tgacttaata aagcttttcc tgcatgca                           1481

<210> SEQ ID NO 2
<211> LENGTH: 228
<212> TYPE: PRT
<213> ORGANISM: Artificial Sequence
<220> FEATURE:
<223> OTHER INFORMATION: Description of Artificial Sequence:  Synthetic
      Primer

<400> SEQUENCE: 2

Met Gly Asn Ala Ser Phe Gly Ser Lys Glu Gln Lys Leu Leu Lys Arg
 1               5                  10                  15

Leu Arg Leu Leu Pro Ala Leu Leu Ile Leu Arg Ala Phe Lys Pro His
            20                  25                  30

Arg Lys Ile Arg Asp Tyr Arg Val Val Val Gly Thr Ala Gly Val
            35                  40                  45

Gly Lys Ser Thr Leu Leu His Lys Trp Ala Ser Gly Asn Phe Arg His
        50                  55                  60

Glu Tyr Leu Pro Thr Ile Glu Asn Thr Tyr Cys Gln Leu Leu Ala Ala
65                  70                  75                  80

Ala Thr Val Cys Phe Pro Cys Thr Ser Pro Thr Ala Arg Val Ala Thr
                85                  90                  95
```

Ala Thr Ala Leu Gln Arg His Val Ile Ala Arg Gly His Ala Phe Val
                100                 105                 110

Leu Val Tyr Ser Val Thr Lys Lys Glu Thr Leu Glu Glu Leu Lys Ala
            115                 120                 125

Phe Tyr Glu Leu Ile Cys Lys Ile Lys Gly Asn Asn Leu His Lys Phe
        130                 135                 140

Pro Ile Val Leu Val Gly Asn Lys Ser Asp Asp Thr His Arg Glu Val
145                 150                 155                 160

Ala Leu Asn Asp Gly Ala Thr Cys Ala Met Glu Trp Asn Cys Ala Phe
                165                 170                 175

Met Glu Ile Ser Ala Lys Thr Asp Val Asn Val Gln Glu Leu Phe His
            180                 185                 190

Met Leu Leu Asn Tyr Lys Lys Lys Pro Thr Thr Gly Leu Gln Glu Pro
        195                 200                 205

Glu Lys Lys Ser Gln Met Pro Asn Thr Thr Gly Lys Leu Leu Asp Lys
    210                 215                 220

Cys Ile Ile Met
225

<210> SEQ ID NO 3
<211> LENGTH: 9
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 3

Tyr Leu Pro Thr Ile Glu Asn Thr Tyr
 1               5

<210> SEQ ID NO 4
<211> LENGTH: 9
<212> TYPE: PRT
<213> ORGANISM: Artificial Sequence
<220> FEATURE:
<223> OTHER INFORMATION: Description of Artificial Sequence:   Synthetic
      Peptide

<400> SEQUENCE: 4

Tyr Asp Pro Thr Ile Glu Asp Ser Tyr
 1               5

<210> SEQ ID NO 5
<211> LENGTH: 7397
<212> TYPE: DNA
<213> ORGANISM: Artificial Sequence
<220> FEATURE:
<223> OTHER INFORMATION: Description of Artificial Sequence:   Synthetic
      Peptide
<220> FEATURE:
<221> NAME/KEY: modified_base
<222> LOCATION: (1)..(7386)
<223> OTHER INFORMATION: N = A, C, G, T/U

<400> SEQUENCE: 5
nagaanaggg tccaaggngt gggagaatag nttgtgtana cattgnagga agacngaaga      60
tacaggcaga acatcngtca atagagggna ggganaacat gggtttgacc nggaaagccg    120
gtacatttng gaggaggagg ggtntggcca gtggtggcag gagggaggtt gtggaagcca    180
gggttcttgt tacatatgng aagcctgtaa tatgcttcag aaagaataga nggcatatgt    240
acctcaaaag gtaaatgacc ttaaacggtg tcagactntn agttaaatct ctcccggatc    300

```
agagaaagac ctggaaaggg aaggagattg tccacagaac acaaatttcc ctcgcaaaag    360
atagcattgc acaggaccat tccaaaatat gtcagaaata tattntgggg taaaatactt    420
tgatcgccct tagggctgnt acctgtcatg tgatgctata ccagaatcag gttggaattt    480
gttttgagac aggttctcac tttgttgctc agattggagt acagtggcag tgatcacggc    540
tcactgcagc ctcgatctcc ttgatgtggg aggctcaagt gatcntccca catcagcctc    600
ccaaatagct gggactacag gcggccacca ccacactggg cgatattntt taaaagtaga    660
gacaagttct ccccatgttg cccaggctgg tntntaactc ntggcctcaa cctccttatt    720
ttntaggatt acaggcgcca ggntagacct cacaggtctt tagactttta cgcaccaggt    780
acctggtagg gggagggatt atagtggcag aagagcagta ccagtggccc acaccacaca    840
ccctggcntc agctggctgg ggcacacaaa accaggtgct accgtcaacg actaggccca    900
tagggtactg ctgtcaaaac ctgctgccaa caanttccac acactcccca aaacgctcgg    960
taggcggtgg tgcgcagctt tcaatgcatc cgccgccagg cgctcacagg caagggagaa   1020
agaagccaga cggagctcgg agatgtggag ggcagacgca ggcgcatttg aaaagggac     1080 tggcggtggg aggcgcagag ggaaaaagga acgacacaat cgggcttcnt agccgctggc   1140
ggacccgatg gggcgtcctg cgagggttcg gcgagggttc tgccaggata gtagcattgc   1200
gcccaaggag tgagaggcac ccgggggntac tggagccaga ccctcaaccc gccctagtgg   1260
gaggcgaaga acaacgaaag cctcgtattc ccatttctnt aatggctaat gacattaaag   1320
gttttcatat ggttatttgc catctgcata tcttcagtga aatgtctgtt tatgtcttct   1380
gactattctc taattggatt tttaaaaata attggttttt gagttattta catattctag   1440
atactggttg tatgccagat atatggcttg taaatatttt ctcctaggta aaccttttca   1500
gtatcgttac agggtctttc acaaagcaaa agttttaaat ttatggagtc taattcatca   1560
acatttcttt ttaccggtct tgccactaat gtcaatttaa gaaccttttg cctagccttta  1620 gacaatagtt tgttgttttt taaaaccgtt ttgtaatttt actcgtcaca gttatatcta   1680
gccattaatt tttatgtaag ggttattttt ggcggggggg aatntataga gtcctgtct    1740 tttcagtatc atttgtggaa aagattatnt gtcctgcatt aaantgcttt tggacttttng  1800 tctaaaatca gttggaccgg tttttgttgg caaagttttg cctgaagctt attccaacag   1860
gtgagaaaaa gtccacagtt taacagttcn tccccaacct gtaacccgc cttgaacttt    1920 tggaatagcc cctcgattgt tgtagatgcc aagcggacct cgcgccgctn tgcgttgggc    1980
cagcccctca cagctggttt nttaccangt attgcgcaag cggaatttat gcntgttacc   2040
cacactccnt gcgcccccgc accccgntcc tgtgcgcaag tcggaatata aaaccgcgga   2100
ggagtgagct cttggggtgt ccagttggtt gccgcggcag tctctccgag cagcgcattt   2160
gtcttctagg ctgcttggtt cgtgcctccg agaaaggtaa gtctttcttt cgcttttta   2220 ggggtacttg aaaacaacaa gtgtcagaca aagcagcaga tgctgttgcg cagtanaagt    2280
ttatgggcga gttgtccctg aaactggaac caggtctttc ttggcgcgat tacgcaagaa   2340
ccacccgcag ccctgcgggc tcctggcagg tcctgcaact gcactttgga tagtcccgtt   2400
gggaagctag cacttttaa tataaaagaa cgaggtttga taagtgtgcg agcttaaagg    2460
ttgacacagt gtccactatt acagctgcgt angtagctag tgttcaggaa gtaatagtgg   2520
agtcatgtag tgtgaaagta agattgaaat gggcgaggag ggtagcagcc gccacagcca   2580
ccagagagaa acctgacctt gcaggtgcgt ggtgatgtcc atgagccagg ctggtgccgc   2640
```

-continued

```
aacagcagcg gcgggacctt gagctccgca cggccgctgg gtttggacgc cctctggttc    2700
ctggaaactt tcacctcccc ctcagcctga ggccaggtgg cctgggaagg tggaacgagt    2760
gtggagggga gtgggggggg gggtccactg cctganaatg anaattctct tcacatctgg    2820
aaattcagtt atcacgtgtg tcctttacca attttttttc ttttattttc tttttgatag    2880
agacggcgt ctccctatgt tacccaggct agtcttgaac tcctgtgctt aagcgatcct    2940
cccaccttga cttcccaaag tgctggaatt acaggcatga gccaatgcgc ccggctgctt    3000
taccaattt ctatgaatga atttgtacat acatcccta gancaggaag tnatgtanaa     3060
cagaataatt agtaatgcac atttcctaat gtgggatgtt ggtggccnac agatatttgg    3120
tctttactgg aactcttgat actaacatgg nagtttataa tagttgtgga gagtgcagac    3180
aaggctagga tttctgtgac tagagaactc ttagtgcgtg aagacctaag gaaagctgga    3240
ttgttgattt ttgttaataa ataagatgtg aaagattgca tcactgtagc agaaatctcc    3300
tagtttttta agctaaattc tattaaaggt catcattgct aaaggaattg tgcccaggat    3360
ttggatagct gatgtcatta cttaatatta gatgatatca actaaccaca tctcatagac    3420
tggaataaag tgctagattt tacctgaaag ctgcaaaaat gaatggttta gatatatgta    3480
tgtatttatt ttatatcaat ttcaaatatt tactgtatta acctccctgg cccccttaa    3540
tcaagaatat aaaatcatct acttaaattt tgccacttaa gtttagaaca ctcttagaat    3600
cacactatct taaagaagcc agactagaat tagaagcaan ttaantctga agatataaca    3660
accagcaaca acatttttt ttttcaaatg aaaactctaa tatggggtgg gtatgttgtg    3720
tcacacctgt aatcccaaca ctttgggagg ctgatgcagg aggatcactt gaacacagga    3780
gttcaagacc ancctggaca acatagcaaa accctgtccc tacaaaaaat aanaaaatta    3840
gctgggcatg gtgtcacatg cctgtagtcc cagctactcg ggaggctgag gtganaggat    3900
tgattgatcc caggaggttg aggctgcagt gagtcatgat cgcatgactg cactccaacc    3960
tgagggacan agcaagaccc tgactcaaaa aaaaaaaaca aaaaaaaaa aaccaccacc    4020
aaaactctaa tatggacata ttactctctc atgggacttg cacattctaa aaagggtcct    4080
tttcccagt actgggganan tatntgttca actacgcagc cagcaanaca ggctatttta    4140
tatagggagt gtgctattca caaaaagcct ctcttctctt tctggtattg tacatgacac    4200
aatcatagct gtacctgaaa aaantgcat tttaaggacc atcatcacct aaaaacatgt    4260
ntaaatttct atacctagtg ccacaggaat nacattgcct tgtactattc ctacctctgt    4320
ccaaaggcca gctatgtggt ctgtctgcat ggtgcctaaa acttttttcca tctgacctag    4380
gatgcttctg aagcagtccc cctgggcagc tgtctggtat ttaggatata cctgtgagaa    4440
aanttncta caacccctaat ctactatgtt tattcctgaa ctcaaaaant tcatttgact    4500
gttcaattcc tgaaatttnc tctatttcca naaggctgaa ttaaaattac tttgttaaag    4560
gtantagcca tggcaaaaaa aaaaccactg ttctgtaaaa aaactcattc aatatttaca    4620
atcttttcta atcaaaaatt anatcctgaa aagaaaggtt catatatata tatatatata    4680
tatatatata tatatatata tatatatata tatatcttt tttttttttt tttttttttt    4740
tttttactc cactgtcatt gtgactaagg attcatgaac taagacccct ccctcagctt    4800
ttggtggcac atggtgacag catgctcaga gcaaaggtgc tccccatgcc tnttctgggg    4860
ntgcactgac tgcaggtacc tccccttttt acatcccaca ccagtgaatc caaaaacccc    4920
ctcctttctc ctgtantgat gactctgtag ctttaaccag ggngacggtg tcactntaaa    4980
tgtcaccttg gcattcagcc ccatagagtg gggaaaattc cctcacctgt ttctctttga    5040
```

-continued

```
ctgttcagtc cacttcaatt aaaatcttaa ttttacaagc gaggaaatga gagtgtttct    5100
tgtaggggtg tagtgagaat ttaataaaac agtttaagga aagaaaacaa aaggtagtat    5160
tgctgcactt tntagatggt aaaaagcaaa ccaccatgtc tgtttaatat atatcacctg    5220
ctggtccntc ggtctagcag gctgaactgt gtgcctggga attttttttct cgctgtgtgc    5280 acccctttac gtcacaggg tggatctcttc agagtccatg nggagcagct ggccaggctg    5340
acatgatctg acaagattgt aggttaccan taccatctct caccgtctca ctttcttcct    5400 agggggtctcc tgctgccagc taagtgtggg agaacttgtg cacgtatctc ccctccgaat    5460
cccaacgatg ggtaacgcca gctttggctc caaggaacag aagctgctga gcggttgcg    5520 gcttctgccc gccctgctta tcctccgcgc cttcaagccc cacaggaaga tcagagatta    5580
ccgcgtcgtg gtagtcggca ccgctggtgt gggaaaagt acgctgctgc acaagtgggc    5640
gagcggcaac ttccgtcatg agtacctgcc gaccattgaa atacctact gccagttgct    5700 gggctgcagc cacggtgtgc tttccctgca catcaccgac agcaagagtg gcgacggcaa    5760
ccgcgctctg cagcgccacg ttatagcccg gggccacgcc ttcgtcctgg tctactcagt    5820
caccaagaag gaaaccctgg aagagctgaa ggccttctat gagctgatct gcaagatcaa    5880
aggtaacaac ctgcataagt tccccatcgt gctggtgggc aataaaagtg atgcaccca    5940 ccgggaggtg gccctgaatg atggtgccac ctgtgcgatg gagtggaatt gcgccttcat    6000
ggagatttca gccaagaccg atgtgaatgt gcaggagctg ttccacatgc tgctgaatta    6060
caagaaaaag cccaccaccg gcctccagga gcccgagaag aaatcccaga tgcccaacac    6120
cactgagaag ctgcttgaca agtgcataat catgtgagcc ctgggcctta agagccagct    6180
cttcctatcc tgtagcgtgt agaaaacgtg gactcatttc actatgttac atgtacatgg    6240
ttgattttgt gctgttgttt ggactgtaac atccatgttg tcaatacgta taccttgtaa    6300
gtggataact tttcttttc ccaggccaga gaattcaaat tgttaaaaca ttggcatttg    6360
aagaggagaa caaatgtag catgatgtat ttaaagtaag gcctttagta atgaatgtaa    6420
tgagagaaaa tgttttgaaa agaacaaaac atcaaaatga atagaaagaa aaattggaag    6480
gcgtcctttt ggtaacccga ttattgtgta ttaccttttaa atatttcaca tcctgtaagt    6540
gcttaatcat atcttttaat tgtgtattta agaaaagtgt tttcacaaca aaagcttttg    6600
ataaattgct gcgtgacata tactaaataa aaaatgaat atgttgatca ttaggggtgt    6660
gggagcagag aaaattgtga aagtgactct cactaaagat gttagtagtt tctcatgtca    6720
tttaaaaatg tttgagtatt ctgcatagca gtttgtaaaa gtgtaacagc ttattgactt    6780
aataaagctt ttcctgcatg caatcagctg taanaatttg tctcaccana aaacaaaaca    6840
ttgcccattg tattaaaatt taaccatat ctgttaaaag tttccaataa gaacttcaca    6900 catgatgtc cttgccatgt tgaaattatc caatatggga gggggtgtt ttagggaggt    6960 ctctgcaata canagctgtt ttgtgtcttt cctgaactga catcccgaaa aactccaggc    7020
atctttgagg aaaatggtca cagtgttgct gtctcanagg aagcgggtga aaagcaagcc    7080
tctgccttct gcctcttcct atattctgaa atactggata taggcaatag ggagcagaat    7140
gaaagacaag gggaggaatg atatttgaga nactcccca taagggagtt tttaaagaga    7200
ttatatttga acataatttt ttgagcgagg gaataaagta tacatatcct tgcttttgan    7260
agtttttttt ttttttttaa attgggaaan gttcagggga ggcnctnaat ctantgattt    7320
ttttcccccc naaatnttat tgaacnaata tctattgaac aatnttntnt ntttctacac    7380
```
aaaaancaca ttgttcc                                                    7397

<210> SEQ ID NO 6
<211> LENGTH: 130
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 6

Met Thr Glu Tyr Lys Leu Val Val Val Gly Ala Gly Gly Val Gly Lys
 1               5                  10                  15

Ser Ala Leu Thr Ile Gln Leu Ile Gln Asn His Phe Val Asp Glu Tyr
                20                  25                  30

Asp Pro Thr Ile Glu Asp Ser Tyr Arg Lys Gln Val Val Ile Asp Gly
            35                  40                  45

Glu Thr Cys Leu Leu Asp Ile Leu Asp Thr Ala Gly Gln Glu Glu Tyr
    50                  55                  60

Ser Ala Met Arg Asp Gln Tyr Met Arg Thr Gly Glu Gly Phe Leu Cys
65                  70                  75                  80

Val Phe Ala Ile Asn Asn Thr Lys Ser Phe Glu Asp Ile His Gln Tyr
                85                  90                  95

Arg Glu Gln Ile Lys Arg Val Lys Asp Ser Asp Asp Val Pro Met Val
            100                 105                 110

Leu Val Gly Asn Lys Ser Gly Pro Gly Cys Met Ser Cys Lys Cys Val
        115                 120                 125

Leu Ser
    130

<210> SEQ ID NO 7
<211> LENGTH: 130
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 7

Met Arg Glu Tyr Lys Val Val Val Leu Gly Ser Gly Gly Val Gly Lys
 1               5                  10                  15

Ser Ala Leu Thr Val Gln Phe Val Thr Gly Thr Phe Ile Glu Lys Tyr
                20                  25                  30

Asp Pro Thr Ile Glu Asp Phe Tyr Arg Lys Glu Ile Glu Val Asp Ser
            35                  40                  45

Ser Pro Ser Val Leu Glu Ile Leu Asp Thr Ala Gly Thr Glu Gln Phe
    50                  55                  60

Ala Ser Met Arg Asp Leu Tyr Ile Lys Asn Gly Gln Gly Phe Ile Leu
65                  70                  75                  80

Val Tyr Ser Leu Val Asn Gln Gln Ser Phe Gln Asp Ile Lys Pro Met
                85                  90                  95

Arg Asp Gln Ile Ile Arg Val Lys Arg Tyr Glu Lys Val Pro Val Ile
            100                 105                 110

Leu Val Gly Asn Lys Asp Lys Asp Pro Cys Cys Ser Ala Cys Asn
        115                 120                 125

Ile Gln
    130

```
<210> SEQ ID NO 8
<211> LENGTH: 130
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 8

Met Arg Glu Tyr Lys Ile Val Val Leu Gly Ser Gly Gly Val Gly Lys
 1               5                  10                  15

Ser Ala Leu Thr Val Gln Phe Val Gln Gly Ile Phe Val Glu Lys Tyr
                20                  25                  30

Asp Pro Thr Ile Glu Asp Ser Tyr Arg Lys Gln Val Glu Val Asp Cys
            35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Glu Asp Val Pro Asn Ile
            100                 105                 110

Leu Val Gly Asn Lys Glu Lys Lys Pro Lys Lys Ser Cys Leu
        115                 120                 125

Leu Leu
    130

<210> SEQ ID NO 9
<211> LENGTH: 130
<212> TYPE: PRT
<213> ORGANISM: Artificial Sequence
<220> FEATURE:
<223> OTHER INFORMATION: Description of Artificial Sequence: Synthetic
      Peptide

<400> SEQUENCE: 9

Met Arg Glu Tyr Lys Ile Val Val Leu Gly Ser Gly Gly Val Gly Lys
 1               5                  10                  15

Ser Ala Leu Thr Val Gln Phe Val Gln Gly Ile Phe Val Glu Lys Tyr
                20                  25                  30

Asp Pro Thr Ile Glu Asp Ser Tyr Arg Lys Gln Val Glu Val Asp Ala
            35                  40                  45

Gln Gln Cys Met Leu Glu Ile Leu Asp Thr Ala Gly Thr Glu Gln Phe
    50                  55                  60

Thr Ala Met Arg Asp Leu Tyr Met Lys Asn Gly Gln Gly Phe Ala Leu
65                  70                  75                  80

Val Tyr Ser Ile Thr Ala Gln Ser Thr Phe Asn Asp Leu Gln Asp Leu
                85                  90                  95

Arg Glu Gln Ile Leu Arg Val Lys Asp Thr Asp Asp Val Pro Met Ile
            100                 105                 110

Leu Val Gly Asn Lys Pro Gly Lys Ala Arg Lys Lys Ser Ser Cys Gln
        115                 120                 125

Leu Leu
    130

<210> SEQ ID NO 10
<211> LENGTH: 130
<212> TYPE: PRT
```

-continued

```
<213> ORGANISM: Artificial Sequence
<220> FEATURE:
<223> OTHER INFORMATION: Description of Artificial Sequence:  Synthetic
      Peptide

<400> SEQUENCE: 10

Ile Arg Asp Tyr Arg Val Val Val Gly Thr Ala Gly Val Gly Lys
 1               5                  10                  15

Ser Thr Leu Leu His Lys Trp Ala Ser Gly Asn Phe Arg His Glu Tyr
            20                  25                  30

Leu Pro Thr Ile Glu Asn Thr Tyr Cys Gln Leu Leu Ala Ala Ala Thr
            35                  40                  45

Val Cys Phe Pro Cys Thr Ile Ser Pro Thr Ala Arg Val Ala Thr Ala
 50                  55                  60

Thr Ala Leu Gln Arg His Val Ile Ala Arg Gly His Ala Phe Val Leu
 65                  70                  75                  80

Val Tyr Ser Val Thr Lys Lys Glu Thr Leu Glu Glu Leu Lys Ala Phe
                85                  90                  95

Tyr Glu Leu Ile Cys Lys Ile Lys Asn Leu His Lys Phe Pro Ile Val
               100                 105                 110

Leu Val Gly Asn Lys Asn Thr Thr Glu Lys Leu Leu Asp Lys Cys Ile
           115                 120                 125

Ile Met
130
```

NOEY2 GENE COMPOSITIONS AND METHODS OF USE

The present application is a continuing application of U.S. Provisional Application Ser. No. 60/071,263 filed Jan. 13, 1998, which is a continuing application of U.S. Provisional Application Ser. No. 60/041,580 filed Mar. 21, 1997; the entire contents of each being specifically incorporated herein by reference in its entirety.

The United States government has rights in the present invention pursuant to Grant Number CA39930 from the National Cancer Institute.

1.0 BACKGROUND OF THE INVENTION

1.1 Field of the Invention

The present invention relates generally to the fields of oncology and molecular biology. More particularly, it concerns nucleic acid segments isolated from human chromosome 1p31, which encode a novel tumor suppressor protein, designated NOEY2. Various methods for making and using NOEY2 DNA segments, DNA segments encoding synthetically-modified NOEY2 proteins, and native and synthetic tumor suppressor proteins are disclosed, such as, for example, the use of DNA segments as diagnostic probes and templates for protein production, and the use of proteins, fusion protein carriers and peptides in various immunological and diagnostic applications. Also disclosed are methods for identifying NOEY2-related tumor suppressor polynucleotides and polypeptides, and methods for treating tumors, and in particular, ovarian and breast-related cancers.

1.2 Description of Related Art

Oncogenesis was described by Foulds (1958) as a multistep biological process, which is presently known to occur by the accumulation of genetic damage. On a molecular level, the multistep process of tumorigenesis involves the disruption of both positive and negative regulatory effectors (Weinberg, 1989). Defects leading to the development of retinoblastoma have been linked to a tumor suppressor gene (Lee et al., 1987), and a variety of oncogenes and other tumor suppressors have been identified in a host of malignancies. Unfortunately, there remains an inadequate number of treatable cancers, and the effects of cancer are catastrophic—over half a million deaths per year in the United States alone.

1.2.1 Tumor Suppressors

Tumor suppressor proteins function to negatively regulate cell cycle processes, preventing the uncontrolled growth exhibited by cancerous cells. Tumor suppressor proteins function by transcriptional regulation of key genes involved in cellular growth and division. Unlike protooncogenes, for which activation is required for the initiation of cancerous growth, inactivation of tumor suppressors leads to cancer. In normal diploid cells, two copies of the gene encoding a particular tumor suppressor protein are present. The "two hit" hypothesis states that mutation or inactivation of both individual copies of the gene is required for the onset of cancerous growth. Mutations may include deletions, alterations to transcription levels, single or multiple coding changes, and truncations. Inherited mutations in a single tumor suppressor gene typically leads to a recessive heterozygous phenotype. Cells remain phenotypically normal until mutation of the second, wild type copy of the gene. Familial inheritance of a mutant copy of a tumor suppressor gene does render the individual more prone to cancer, as inactivation of the single normal gene is sufficient to initiate cancer. The two most heavily studied tumor suppressor genes are the retinoblastoma gene Rb and the p53 gene.

The retinoblastoma gene Rb was the first discovered tumor suppressor gene. The Rb protein is a 110 kDa nuclear phosphoprotein that reduces the growth rate of cells, and mutations in this protein have been found in breast, prostate, and small cell lung carcinomas. The Rb protein binds to DNA, but without any sequence specificity. Rb effects its regulatory function through the formation of complexes with transcription factors. Rb has been shown to interact with transcription factor E2F, which binds to the promoters of cellular genes such as DNA polymerase α and ribonucleotide reductase. Heterozygous individuals inherit one defective and one normal copy of the Rb gene. Upon inactivation of the second, functional copy of the gene, cancerous growth initiates. A wide range of mutations including deletions, duplications, and point mutations have been found to lead to inactivation of the Rb protein.

The p53 tumor suppressor has been found to be mutated in about 60% of human cancerous growths, making p53 the most commonly mutated gene in human cancers. Wild type p53 protein binds to DNA and is believed to function as a transcriptional regulator. The p53 protein also binds to the mdm2 protein, commonly expressed at high levels in tumors. Levels of wild type p53 protein increases upon subjecting a cell to radiation or chemical agents which damage DNA. The p53 protein has been implicated in DNA repair mechanisms that prevent the duplication of damaged or altered DNA. It has been further speculated that p53 protein prevents the cell from entering S phase until the complete repair of damaged DNA has been achieved. The p53 protein is normally found at low, often undetectable levels in cells, and has a short cellular half life. Mutant p53 proteins often are more resistant to degradation, and are present at immunohistochemically detectable levels in cancerous cells. Most p53 gene mutations occur in four highly conserved regions. Mutant p53 proteins are dominant inactivators, by their ability to bind to and inactivate wild type p53 protein.

1.2.2 Ovarian Cancer

The ovary is the fifth most common site of cancer among American women and ovarian neoplasms constitute the fourth leading cause of cancer death. Ovarian cancer affects 22,000 women in the United States each year and causes some 14,000 deaths annually. Approximately 90% of ovarian cancers arise from epithelial cells that cover the ovarian surface or that line inclusion cysts. Ovarian cancers exhibit a distinctive pattern of metastasis. Like other epithelial neoplasms, ovarian cancer can metastasize to pelvic and retroperitoneal lymph nodes and can spread hematogenously to distant sites. More frequently, however, ovarian cancer cells spread over the surface of the peritoneal cavity, forming multiple nodules on the parietal and visceral peritoneum. Blockade of diaphragmatic lymphatics and increased transudation of fluid produce accumulation of ascites fluid that contains varying numbers of tumor cells. Abdominal distention by malignant ascites is a frequent mode of clinical presentation. Early stage ovarian cancer rarely produces symptoms and at present there is no proven strategy for early detection. In more than 75% of cases, tumor cells have metastasized beyond the ovaries at presentation. Initial clinical management generally involves cytoreductive surgery and drainage of ascites, providing large amounts of tissue for study. Following removal of as much tumor as possible, cytotoxic chemotherapy is generally administered. Introduction of platinum based compounds and the taxane derivatives has improved median survival of patients with advanced disease, but the five year survival rate is still only 28% for all stages and has not improved in the last several decades. Disease frequently persists and recurs within the peritoneal cavity, producing intestinal obstruction. Therapeutic strategies that prevent such progression and that treat disease regionally by intraperitoneal infusion continue to hold promise. Identification of genes whose aberrant function can be demonstrated in ovarian carcinomas may have important diagnostic and therapeutic applications.

1.2.3 Breast Cancer

Breast cancer is the most common form of cancer among women, affecting about one in eight women. Approximately 185,700 new cases are diagnosed in the U.S. annually, and breast cancer is responsible for about 44,560 deaths in the U.S. per year. While predominantly observed in women, 1,400 cases of breast cancer are diagnosed annually in men, and 260 men die of breast cancer per year. Breast cancer first manifests itself as a painless lump, detectable by self-examination and clinical breast exams including mammograms. Commonly, growth initiates in the lining of the ducts or in the lobules of the breast. Current clinical treatments include mastectomy (removal of the entire breast) or lumpectomy (removal of the tumor and surrounding tissue) for localized tumors. Chemotherapy, radiotherapy, or hormone-blocking therapy may be further used to control cancerous cells. Breast cancer cells can metastasize to the lymph nodes, skin, lungs, liver, brain, or bones. Metastasis may occur early or late in the disease progression, although typically metastasis occurs once the cancerous growth reaches a size of about 20 mm. Metastasis is achieved by cells breaking away from the parental mass and entering either the bloodstream or the lymphatic system.

Genetic inheritance appears to play a role in about 5–10% of breast cancer patients. Mutations in the BRCA1, BRCA2, and p53 tumor suppressor genes have been observed to confer high risks of breast and ovarian cancers. BRCA1 mutations are present at between 1 in 300 to 1 in 800 females. In the BRCA1 gene, over 200 different mutations have been discovered to date. The mutations observed are not localized to a single region, further complicating genetic analysis. Greater than 80% of the observed mutations result in a truncated form of the BRCA1 protein. Individuals with familial hereditary BRCA1 possess one normal and one mutant form of the gene, and are therefore much more likely to develop breast cancer. It is estimated that women with a hereditary BRCA1 mutation are about 76% likely to develop breast cancer by 70 years of age.

BRCA2 has been identified on chromosome 13q through linkage analysis of 15 breast cancer families that did not demonstrate BRCA1 linked breast cancer. Unlike BRCA1 mutations, BRCA2 does not substantially elevate the risk of ovarian cancers. The BRCA2 gene encodes a protein of 3,418 amino acids, many of which are acidic or basic. Most mutations observed involve base deletions that alter the reading frame, and result in a premature truncation of the protein. BRCA1 and BRCA2 account for about 45% of familial inherited breast cancers each, leaving 10% for one or more additional genes. Interestingly, all male breast cancers appear to be due to mutations in the BRCA2 gene.

Mutations found in breast tumor p53 genes are commonly single base pair changes which result in variants with increased cellular half lives. Altered p53 proteins have been observed in 20–25% of breast cancers.

1.3 Deficiencies in the Prior Art

There are relatively few tumor suppressor genes whose mutations have been shown to correlate with the presence of cancerous cells. Those that have been characterized typically have many possible types and positions of mutations, complicating genetic analyses and the prediction of cancer predisposition. Therefore, what is lacking in the prior art is the identification and characterization of novel tumor suppressor genes, and identification of the role of the proteins encoded by such genes in cancer diagnosis and treatment. Such genes, in combination with improved genetic testing, and improved correlation of specific genetic mutations with particular cancer susceptibility are needed to facilitate early and effective treatment of these proliferative diseases.

2.0 SUMMARY OF THE INVENTION

The present invention overcomes these and other limitations in the prior art by providing a novel tumor suppressor protein (designated NOEY2) (SEQ ID NO:2) and the gene which encodes it (designated NOEY2). This gene is expressed in normal ovarian surface epithelial cells, but consistently absent or down-regulated in ovarian cancer cells. The invention provides unique polynucleotide sequences which comprise the cDNA (SEQ ID NO:1) and the genomic DNA (SEQ ID NO:5) encoding this NOEY2 tumor suppressor. A further objective of the invention is to provide polynucleotide segments comprising all or parts of a gene encoding NOEY2. Polynucleotide probes and primers specific for these NOEY2 genes also represent important compositions provided by the invention. It is a further objective of the invention to provide antibodies specific for NOEY2, methods for identifying NOEY polypeptide and polynucleotide compositions, methods for producing such compositions, and methods for using these compositions in a variety of diagnostic and therapeutic regimens. The invention also provides methods and compositions for the detection of NOEY2 compositions in biological and clinical samples, and methods for regulating the proliferation of tumor cells in vitro and in vivo.

In one important embodiment, the invention provides an isolated and purified amino acid segment comprising a NOEY2 tumor suppressor protein (SEQ ID NO:2) comprising the amino acid sequence of SEQ ID NO:2. The coding region for the NOEY2 polypeptide is from nucleotide 150 to 833 of SEQ ID NO:1, (the cDNA for NOEY2). The genomic DNA sequence is presented in SEQ ID NO:5. The NOEY2 protein exhibits tumor suppressor activity which is related to cyclin D1 promoter inhibition. In related embodiments, methods for making and using this protein, derivatives and mutants thereof, and antibodies directed against these proteins are also disclosed.

In another important embodiment, the invention provides an isolated and purified nucleic acid segment comprising the NOEY2 gene which encodes the NOEY2 tumor suppressor protein disclosed herein. The nucleotide sequence of an exemplary NOEY2 gene is given from position 150 to position 833 of SEQ ID NO:1 (NOEY2 cDNA) and SEQ ID NO:5 (NOEY2 genomic). In related embodiments, methods for making, using, altering, mutagenizing, assaying, and quantitating these nucleic acid segments are also disclosed. Also disclosed are diagnostic methods and assay kits for the identification and detection of related NOEY2 gene sequences in a variety of in vitro and in vivo methodologies.

Another aspect of the present invention is an animal cell, such as a human or other animal cell, that comprises a NOEY2 polypeptide or polynucleotide. In a preferred embodiment, the cell is an ovarian surface epithelial cell that produces a tumor suppressor polypeptide of approximately 26-kDa, and that is identical to, or substantially homologous with, the NOEY2 polypeptide identified in SEQ ID NO:2.

A further aspect of the present invention is a vector (such as a plasmid, cosmid, virus, phagemid, or the like), that includes within its nucleotide sequence a nucleic acid segment that comprises one or more NOEY2 genes, or portions thereof. Preferably such a vector is comprised within a transformed host cell. The transformed host cell may be a bacterial, animal, fungal, or plant cell, and may be comprised within a transgenic animal, or may be comprised within a culture of bacteria, yeast, fungus, animal or plant cells.

In another embodiment, there is provided a monoclonal antibody that binds immunologically to a tumor suppressor designated as NOEY2. The antibody may be non-cross reactive with other human polypeptides, or it may bind to non-human NOEY2, but not to human NOEY2. The antibody may further comprise a detectable label, such as a fluorescent label, a chemiluminescent label, a radiolabel or an enzyme. Also encompassed are hybridoma cells and cell lines producing such antibodies.

In another embodiment, there is included a polyclonal antisera, antibodies of which bind immunologically to a tumor suppressor designated as NOEY2. The antisera may be derived from any animal, but preferably is from an animal other than a human. Preferred antigens for the preparation of such sera include a NOEY2 polypeptide isolated from a human, rat, goat, rabbit, pig, horse, cat, dog, hamster, monkey or other such animal cell line. Preferred hosts for the preparation of a polyclonal antisera specific for NOEY2 include animals such as rabbits, goats, and other such animals.

The invention also provides pharmaceutical compositions which comprise one or more of the NOEY2 compositions disclosed herein. Such compositions may include NOEY2 or NOEY2-derived polypeptides, polynucleotides, antibodies, antisera, antigens, peptide epitopes, protein fusions, peptides and the like.

In still yet another embodiment, there is provided a method of diagnosing a cancer comprising the steps of (a) obtaining a sample from a subject; and (b) determining the expression a functional NOEY2 tumor suppressor in cells of the sample. Preferably the cancer is ovarian or breast cancer, although the cancer may also be brain, lung, liver, splenic, renal, lymphatic, intestinal, pancreatic, leukemia, colon, stomach, endometrial, prostate, testicular, skin, head and neck, esophageal, bone marrow or blood cancer. In a preferred embodiment, the cancer is ovarian cancer or breast cancer. The sample is a cell, cell culture, tissue or fluid sample, and may be of clinical or non-clinical origin.

In one format, the method involves assaying for a nucleic acid from the sample. The method may further comprise subjecting the sample to conditions suitable to amplify the nucleic acid. Alternatively, the method may comprise contacting the sample with an antibody that binds immunologically to a NOEY2, for example, in an ELISA. The comparison, regardless of format, may include comparing the expression of NOEY2 with the expression of NOEY2 in non-cancer samples, for example in normal ovarian epithelial cells. The comparison may look at levels of NOEY2 expression. Alternatively, the comparison may involve evaluating the structure of the NOEY2 gene, protein or transcript. Such formats may include sequencing, wild-type oligonucleotide hybridization, mutant oligonucleotide hybridization, SSCP, PCR™ and/or RNase protection. Particular embodiments include evaluating wild-type or mutant oligonucleotide hybridization where the oligonucleotide is configured in an array, on a chip, on a wafer, or in a microtiter dish.

In another embodiment, there is provided a method for altering the phenotype of a tumor cell comprising the step of contacting the cell with a tumor suppressor designated NOEY2 under conditions permitting the uptake of the tumor suppressor by the tumor cell. The tumor cell may be derived from an animal organ or tissue such as brain, lung, liver, spleen, kidney, lymph node, small intestine, blood cells, pancreas, colon, stomach, breast, endometrium, prostate, testicle, ovary, skin, head and neck, esophagus, or bone marrow. Preferably the tumor cell is derived from an ovarian or breast cancer cell. The phenotype may be selected from proliferation, migration, contact inhibition, soft agar growth or cell cycling. The tumor suppressor polypeptide may be provided in a pharmaceutical formulation, encapsulated in a liposome, nanocapsule or other lipid particle, or may be carrier-free.

In another embodiment, there is provided a method for altering the phenotype of a tumor cell comprising the step of contacting the cell with a nucleic acid (a) encoding a NOEY2 tumor suppressor and (b) a promoter active in the tumor cell, wherein the promoter is operably linked to the region encoding the tumor suppressor, under conditions permitting the uptake of the nucleic acid by the tumor cell. The phenotype may be proliferation, migration, contact inhibition, soft agar growth or cell cycling. The tumor suppressor-encoding nucleic acid may be provided in a pharmaceutical formulation, encapsulated in a liposome, nanocapsule or other lipid particle, or may be carrier-free. If the nucleic acid is comprised within a viral vector such as retrovirus, adenovirus, adeno-associated virus, vaccinia virus and herpesvirus, it may also be encapsulated in a viral particle.

The invention further provides a method of inhibiting cellular proliferation, comprising providing to a cell a composition comprising a NOEY2 tumor suppressor polypeptide, or a NOEY2 polynucleotide which expresses a NOEY2 polypeptide in a pharmaceutically acceptable vehicle.

The present invention also provides a method of inhibiting tumor proliferation, comprising providing to a tumor cell a composition comprising a NOEY2 tumor suppressor polypeptide or a NOEY2 gene which expresses the NOEY2 protein in a pharmaceutically acceptable vehicle.

In a further embodiment, there is provided a method for treating cancer comprising the step of contacting a tumor cell within a subject with a tumor suppressor designated NOEY2 under conditions permitting the uptake of the tumor suppressor by the tumor cell. The method may involve a human subject.

In still a further embodiment, there is provided a method for treating cancer comprising the step of contacting a tumor cell within a subject with a nucleic acid (a) encoding a NOEY2 tumor suppressor and (b) a promoter active in the tumor cell, wherein the promoter is operatively linked to the region encoding the tumor suppressor, under conditions permitting the uptake of the nucleic acid by the tumor cell. The subject is preferably an animal, and most preferably a human.

In still yet a further embodiment, there is provided transgenic mammal in which both copies of the native NOEY2 gene are interrupted or replaced with another gene.

In an additional embodiment, there is provided a method of determining the stage of cancer comprising the steps of (a) obtaining a sample from a subject; and (b) determining the expression a functional NOEY2 polypeptide in cells of the sample. The cancer is preferably a breast cancer or ovarian cancer. The determining may comprise assaying for a NOEY2 nucleic acid or polypeptide in the sample.

In yet an additional example, there is provided a method of predicting tumor metastasis comprising the steps of (a) obtaining a sample from a subject; and (b) determining the expression a functional NOEY2 polypeptide in cells of the sample. The cancer may be distinguished as metastatic and non-metastatic. The determining may comprise assaying for a NOEY2 nucleic acid or NOEY2 polypeptide in the sample.

In still yet an additional embodiment, there is provided a method of screening a candidate substance for anti-tumor activity comprising the steps of (a) providing a cell lacking functional NOEY2 polypeptide; (b) contacting the cell with the candidate substance; and (c) determining the effect of the candidate substance on the cell. The cell may be a tumor cell, for example, a tumor cell having a mutation in the coding region of NOEY2. The mutation may be a deletion mutant, an insertion mutant, a frameshift mutant, a nonsense mutant, a missense mutant or splice mutant. The determining may comprise comparing one or more characteristics of the cell in the presence of the candidate substance with characteristics of a cell in the absence of the candidate substance. The characteristic may be NOEY2 expression, phosphatase activity, proliferation, metastasis, contact inhibition, soft agar growth, cell cycle regulation, tumor formation, tumor progression and tissue invasion. The candidate substance may be a chemotherapeutic or radiotherapeutic agent or be selected from a small molecule library. The cell may be contacted in vitro or in vivo.

The foregoing objects of the invention and others that are now readily apparent to those of skill in the art having the benefit of the present disclosure are described more fully in the sections which follow:

2.1 NOEY2 DNA Segments

In one embodiment, the present invention concerns DNA segments, that can be isolated from virtually any source, that are free from total genomic DNA and that encode the whole or a portion of the novel peptide disclosed herein. The NOEY2 gene (position 150 to position 833 of SEQ ID NO:1 and SEQ ID NO:5) encodes a NOEY2 polypeptide having the contiguous amino acid sequence shown in SEQ ID NO:2. The inventors contemplate a variety of NOEY2 DNA segments from the present invention will find particular utility. For example, those segments that encode all or portions of the NOEY2 polypeptide, or subunits, functional domains, and the like of NOEY2 and NOEY2-related polypeptides, or those segments that comprise one or more NOEY2 promoter or enhancer regions will be useful in a variety of diagnostic, and therapeutic regimens. Such DNA segments may be native DNA segments isolated using molecular biological methods, or alternatively, such segments may be mutagenized segments, or even segments which have been synthesized in vitro either partially or entirely, using chemical synthesis methods that are well-known to those of skill in the art.

As used herein, the term "DNA segment" refers to a DNA molecule that has been isolated free of total genomic DNA of a particular species. Therefore, a DNA segment encoding a tumor suppressor protein or peptide refers to a DNA segment that contains a NOEY2 polypeptide-coding sequence yet is isolated away from, or purified free from, total genomic DNA of the species from which the DNA segment is obtained. Included within the term "DNA segment", are DNA segments comprising entire NOEY2 genes and/or promoter regions, as well as all partial and smaller fragments and subfragments isolatable from such entire gene-comprising segments, and also recombinant vectors (such as plasmids, cosmids, phagemids, phage, viruses, and the like) which comprise one or more of the NOEY2-specific polynucleotide sequences of the invention. Likewise, the segments may comprise gene sequences which are identical to, or substantially homologous with, a contiguous nucleotide sequence from about position position 150 to about position 833 of SEQ ID NO:1 or SEQ ID NO:5, or gene sequences which encode polypeptides which are identical to, or substantially biologically-functionally equivalent to, the polypeptide disclosed in SEQ ID NO:2.

Similarly, a DNA segment comprising an isolated or purified tumor suppressor protein-encoding gene refers to a DNA segment which may include in addition to peptide encoding sequences, certain other elements such as, regulatory sequences, isolated substantially away from other naturally occurring genes or protein-encoding sequences. In this respect, the term "gene" is used for simplicity to refer to a functional protein-, polypeptide- or peptide-encoding unit. As will be understood by those in the art, this functional term includes not only genomic sequences, including extra-chromosomal DNA sequences, but also operon sequences and/or engineered gene segments that express, or may be adapted to express, proteins, polypeptides or peptides.

"Isolated substantially away from other coding sequences" means that the gene of interest, in this case, a NOEY2 tumor suppressor gene, forms the significant part of the coding region of the DNA segment, and that the DNA segment does not contain large portions of naturally-occurring coding DNA, such as large chromosomal fragments or other functional genes or operon coding regions. Of course, this refers to the DNA segment as originally isolated, and does not exclude genes, recombinant genes, synthetic linkers, or coding regions later added to the segment by the hand of man.

In particular embodiments, the invention concerns isolated DNA segments and recombinant vectors incorporating DNA sequences that encode a NOEY2 polypeptide that includes within its amino acid sequence an at least ten amino acid contiguous sequence from SEQ ID NO:2, and more preferably still, a polypeptide that includes within its amino acid sequence a sequence essentially as set forth in SEQ ID NO:2. In a preferred embodiment, such a DNA segment comprises a gene encoding the amino acid sequence of SEQ ID NO:2, and more preferably still, comprises a polynucleotide which is identical to, or substantially homologous with, the DNA sequence of SEQ ID NO:1 or SEQ ID NO:5.

The term "a sequence essentially as set forth in SEQ ID NO:2," means that the sequence substantially corresponds to a portion of the sequence of SEQ ID NO:2 and has relatively few amino acids that are not identical to, or a biologically functional equivalent of, the amino acids of any of these sequences. The term "biologically functional equivalent" is well understood in the art and is further defined in detail herein (e.g., see Illustrative Embodiments). Accordingly, sequences that have between about 70% and about 80%, or more preferably between about 81% and about 90%, or even more preferably between about 91% and about 99% amino acid sequence identity or functional equivalence to the amino acids of SEQ ID NO:2 will be sequences that are "essentially as set forth in SEQ ID NO:2."

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences that may, for example, include various non-coding sequences flanking either of the 5' or 3' portions of the coding region or may include various internal sequences, i.e., introns, which are known to occur within genes.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared that include a short contiguous stretch encoding the whole or a portion of the peptide sequence disclosed in SEQ ID NO:2, or that are identical to or complementary to DNA sequences which encode the peptide disclosed in SEQ ID NO:2, and particularly the DNA segment disclosed in either of SEQ ID NO:1 or SEQ ID NO:5. For example, DNA sequences such as about 14 nucleotides, and that are up to about 10,000, about 5,000, about 3,000, about 2,000, about 1,000, about 500, about 200, about 100, about 50, and about 14 base pairs in length (including all intermediate lengths) are also contemplated to be useful.

It will be readily understood that "intermediate lengths", in these contexts, means any length between the quoted ranges, such as 14, 15, 16, 17, 18, 19, 20, etc.; 21, 22, 23, etc.; 30, 31, 32, etc.; 50, 51, 52, 53, etc.; 100, 101, 102, 103, etc.; 150, 151, 152, 153, etc.; including all integers through the 200–500; 500–1,000; 1,000–2,000; 2,000–3,000; 3,000–5,000; and up to and including sequences of about 10,000 nucleotides and the like.

It will also be understood that this invention is not limited to the particular nucleic acid sequences which encode peptides of the present invention, or which encode the amino acid sequence of SEQ ID NO:2, including the DNA sequence which is particularly disclosed in SEQ ID NO:1 and SEQ ID NO:5. Recombinant vectors and isolated DNA segments may therefore variously include the peptide-coding regions themselves, coding regions bearing selected alterations or modifications in the basic coding region, or they may encode larger polypeptides that nevertheless include these peptide-coding regions or may encode biologically functional equivalent proteins or peptides that have variant amino acids sequences.

The DNA segments of the present invention encompass biologically-functional, equivalent peptides. Such sequences may arise as a consequence of codon redundancy and functional equivalency that are known to occur naturally within nucleic acid sequences and the proteins thus encoded. Alternatively, functionally-equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the protein or to test mutants in order to examine activity at the molecular level.

If desired, one may also prepare fusion proteins and peptides, e.g., where the peptide-coding regions are aligned within the same expression unit with other proteins or peptides having desired functions, such as for purification or immunodetection purposes (e.g., proteins that may be purified by affinity chromatography and enzyme label coding regions, respectively).

Recombinant vectors form further aspects of the present invention. Particularly useful vectors are contemplated to be those vectors in which the coding portion of the DNA segment, whether encoding a full length protein or smaller peptide, is positioned under the control of a promoter. The promoter may be in the form of the promoter that is naturally associated with a gene encoding peptides of the present invention, as may be obtained by isolating the 5' non-coding sequences located upstream of the coding segment or exon, for example, using recombinant cloning and/or PCR™ technology, in connection with the compositions disclosed herein.

2.2 DNA Segments as Hybridization Probes and Primers

In addition to their use in directing the expression of the gene product of the novel tumor suppressor gene of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least a 14 nucleotide long contiguous sequence that has the same sequence as, or is complementary to, a 14 nucleotide long contiguous DNA segment of SEQ ID NO:1 or SEQ ID NO:5 will find particular utility. Longer contiguous identical or complementary sequences, e.g., those of about 20, 30, 40, 50, 100, 200, 500, 1000, 2000, 5000, 10000 etc. (including all intermediate lengths and up to and including full-length sequences) will also be of use in certain embodiments.

The ability of such nucleic acid probes to specifically hybridize to tumor suppressor protein-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of 10–14, 15–20, 30, 50, or even of 100–200 nucleotides or so, identical or complementary to the DNA sequence of SEQ ID NO:1 or SEQ ID NO:5, are particularly contemplated as hybridization probes for use in, e.g., Southern and Northern blotting. Smaller fragments will generally find use in hybridization embodiments, wherein the length of the contiguous complementary region may be varied, such as between about 10–14 and about 100 or 200 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of 15 to 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as the PCR™ technology of U.S. Pat. Nos. 4,683,195 and 4,683,202 (each incorporated herein by reference), by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions tolerate little, if any, mismatch between the probe and the template or target strand, and would be particularly suitable for isolating tumor suppressor protein-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al., 1994; Segal 1976; Prokop, 1991; and Kuby, 1991, are particularly relevant.

Of course, for some applications, for example, where one desires to prepare mutants employing a mutant primer strand hybridized to an underlying template or where one seeks to isolate tumor suppressor protein-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

2.3 NOEY2 Polypeptide Compositions

The invention also discloses and claims a composition comprising a NOEY2 tumor suppressor protein. The composition may comprises one or more host cells which express a NOEY2 tumor suppressor protein, recombinant host cells expresses the protein, cell suspensions, extracts, inclusion bodies, or tissue cultures or culture extracts which contain the NOEY2 protein, culture supernatant, disrupted cells, cell extracts, lysates, homogenates, and the like. The compositions may be in aqueous form, or alternatively, in dry, semi-wet, or similar forms such as cell paste, cell pellets, or alternatively freeze dried, powdered, lyophilized, evaporated, or otherwise similarly prepared in dry form. Such means for preparing tumor suppressor proteins are well-known to those of skill in the art of protein isolation and purification. In certain embodiments, the tumor suppressor proteins may be purified, concentrated, admixed with other reagents, or processed to a desired final form. Preferably, the composition will comprise from about 1% to about 90% by weight of the tumor suppressor protein, and more preferably from about 5% to about 50% by weight.

In a preferred embodiment, the tumor suppressor protein compositions of the invention may be prepared by a process which comprises the steps of culturing a host cell which expresses a NOEY2 tumor suppressor protein under conditions effective to produce such a protein, and then obtaining the protein from the cell. The obtaining of such a tumor suppressor protein may further include purifying, concentrating, processing, or admixing the protein with one or more reagents. Preferably, the NOEY2 tumor suppressor protein is obtained in an amount of from between about 1% to about 90% by weight, and more preferably from about 5% to about 70% by weight, and even more preferably from about 10% to about 20% to about 30%, or even to about 40% or 50% by weight.

The invention also relates to a method of preparing a tumor suppressor protein composition. Such a method generally involves the steps of culturing a host cell which expresses a NOEY2 tumor suppressor protein under conditions effective to produce the protein, and then obtaining the protein so produced. In a preferred embodiment the cell is an NIH3T3 cell, or any recombinant host cell which contains a NOEY2-encoding DNA segment. Alternatively, the recombinant plasmid vectors of the invention may be used to transform other suitable bacterial or eukaryotic cells to produce the tumor suppressor protein of the invention. Eukaryotic host cells including NIH3T3, COS7, and CAOV3, as well as yeast cells are contemplated to be particularly useful in the preparation of the NOEY2 protein.

Likewise, prokaryotic host cells including Gram-negative cells such as *E. coli, Pseudomonas* spp. and related *Enterobacteraceae* and the like are all contemplated to be useful in the preparation of the tumor suppressor proteins of the invention.

In such embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding a tumor suppressor protein or peptide in its natural environment. Such promoters may include promoters normally associated with other genes, and/or promoters isolated from any bacterial, viral, or eukaryotic cell. Preferred eukaryotic cells are animal cells, with mammalian cells, particularly human cells, being most preferred. Naturally, it will be important to employ a promoter that effectively directs the expression of the DNA segment in the cell type, tissue, organism, animal, or recombinant host cell chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the *Pichia* expression vector system (Pharmacia LKB Biotechnology).

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of tumor suppressor peptides or epitopic core regions, such as may be used to generate anti-tumor suppressor protein antibodies, also falls within the scope of the invention. DNA segments that encode peptide antigens from about 8 to about 50 amino acids in length, or more preferably, from about 8 to about 30 amino acids in length, or even more preferably, from about 8 to about 20 amino acids in length are contemplated to be particularly useful. Such peptide epitopes may be amino acid sequences which comprise contiguous amino acid sequences from SEQ ID NO:2.

2.4 NOEY2 Transgenes and Transformed Host Cells Expressing NOEY2

In yet another aspect, the present invention provides methods for producing a transgenic cell, and in particular a plant or animal cell which expresses a nucleic acid segment encoding the novel NOEY2 tumor suppressor protein of the present invention. The process of producing transgenic cells is well-known in the art. In general, the method comprises transforming a suitable host cell with a DNA segment which contains a promoter operatively linked to a coding region that encodes a NOEY2 tumor suppressor protein. Such a coding region is generally operatively linked to a transcription-terminating region, whereby the promoter is capable of driving the transcription of the coding region in the cell, and hence providing the cell the ability to produce the recombinant protein in vivo. Alternatively, in instances where it is desirable to control, regulate, or decrease the amount of a particular recombinant tumor suppressor protein expressed in a particular transgenic cell, the invention also provides for the expression of tumor suppressor protein antisense mRNA. The use of antisense mRNA as a means of controlling or decreasing the amount of a given protein of interest in a cell is well-known in the art.

In a preferred embodiment, the invention encompasses an animal cell which has been transformed with a nucleic acid segment of the invention, and which expresses a gene or gene segment encoding one or more of the novel polypeptide compositions disclosed herein. As used herein, the term "transgenic host cell" is intended to refer to a host cell, either prokaryotic or eukaryotic, that has incorporated DNA sequences, including but not limited to genes which are perhaps not normally present, DNA sequences not normally transcribed into RNA or translated into a protein ("expressed"), or any other genes or DNA sequences which one desires to introduce into the non-transformed host cell, such as genes which may normally be present in the non-transformed cell but which one desires to either genetically engineer or to have altered expression.

It is contemplated that in some instances the genome of a transgenic host cell of the present invention will have been augmented through the stable introduction of a NOEY2 transgene, either native NOEY2, or synthetically modified or mutated NOEY2. In some instances, more than one transgene will be incorporated into the genome of the transformed host cell. Such is the case when more than one tumor suppressor protein-encoding DNA segment is incorporated into the genome of such a cell. In certain situations, it may be desirable to have one, two, three, four, or even more NOEY2 tumor suppressor proteins (either native or recombinantly-engineered) incorporated and stably expressed in the transformed transgenic host cell. In preferred embodiments, the introduction of the transgene into the genome of the host cell results in a stable integration wherein the progeny of such cells also contain a copy of the transgene in their genome.

A preferred gene which may be introduced includes, for example, a tumor suppressor protein-encoding a DNA sequence, and particularly one or more of the NOEY2 or NOEY2-like tumor suppressor proteins disclosed herein. Highly preferred nucleic acid sequences are those which have the nucleic acid sequence of SEQ ID NO:1 or SEQ ID NO:5, or biologically-functional equivalents thereof, sequences which hybridize to the sequence of SEQ ID NO:1 or SEQ ID NO:5, or sequences which encode the amino acid sequence of SEQ ID NO:2, or sequences which encode a biologically functional equivalent protein of SEQ ID NO:2, or any of those sequences which have been genetically engineered to alter, modify, change, decrease or increase the suppressor activity or specificity of the tumor suppressor protein in such a transformed host cell.

Means for transforming a host cell and the preparation of a transgenic cell line are well-known in the art (as exemplified in U.S. Pat. Nos. 5,550,318; 5,508,468; 5,482,852; 5,384,253; 5,276,269; and 5,225,341, all specifically incorporated herein by reference), and are briefly discussed herein. Vectors, including plasmids, cosmids, phage, phagemids, BACs (bacterial artificial chromosomes), YACs (yeast artificial chromosomes), and DNA segments for use in transforming such cells will, of course, generally comprise either the operons, genes, or gene-derived sequences of the present invention, either native, or synthetically-derived, and particularly those encoding the disclosed tumor suppressor proteins. These DNA constructs can further include structures such as promoters, enhancers, polylinkers, or even gene sequences which have positively- or negatively-regulating activity upon the particular genes of interest as desired. The DNA segment or gene may encode either a native or modified tumor suppressor protein, which will be expressed in the resultant recombinant cells, and/or which will impart a desired phenotype to the transformed host cell.

2.6 Compositions and Methods for Producing NOEY2-Specific Antibodies

In particular embodiments, the inventors contemplate the use of antibodies, either monoclonal or polyclonal which specifically bind to one or more of the NOEY2 polypeptides disclosed herein. Means for preparing and characterizing antibodies are well known in the art (See, e.g., Harlow and Lane, 1988; incorporated herein by reference). The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyl-N-hydroxysuccinimide ester, carbodiimide and bis-biazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycobacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified tumor suppressor protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986, pp. 60–61), but mice are preferred, with the BALB/c mouse being most preferred as this is most routinely used and generally gives a higher percentage of stable fusions.

Following immunization, somatic cells with the potential for producing antibodies, specifically B lymphocytes (B cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, pp. 65–66, 1986; Campbell, pp. 75–83, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, (Gefter et al., 1977). The use of electrically induced fusion methods is also appropriate (Goding, 1986, pp. 71–74).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two wk. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three wk) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

2.7 NOEY2 Polypeptide Screening Methods and Immunodetection Kits

The present invention also provides compositions, methods and kits for screening samples suspected of containing a NOEY2 polypeptide or a NOEY2 polynucleotide that encodes such a tumor suppressor protein. Alternatively, the invention provides compositions, methods and kits for screening samples suspected of containing tumor suppressor proteins or genes encoding tumor suppressor proteins which are functionally equivalent to, or substantially homologous to, the NOEY2 tumor suppressor protein disclosed herein. Such screening may be performed on samples such as transformed host cells, clinical or laboratory samples suspected of containing or producing such a polypeptide or nucleic acid segment. A kit can contain a novel nucleic acid segment or an antibody of the present invention. The kit can contain reagents for detecting an interaction between a sample and a nucleic acid or an antibody of the present invention. The provided reagent can be radio-, fluorescently- or enzymatically-labeled. The kit can contain a known radiolabeled agent capable of binding or interacting with a nucleic acid or antibody of the present invention.

The reagent of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media, a test plate having a plurality of wells, or a microscope slide. When the reagent provided is a dry powder, the powder can be reconstituted by the addition of a suitable solvent, that may be provided.

In still further embodiments, the present invention concerns immunodetection methods and associated kits. It is proposed that the tumor suppressor proteins or peptides of the present invention may be employed to detect antibodies having reactivity therewith, or, alternatively, antibodies prepared in accordance with the present invention, may be employed to detect tumor suppressor proteins or tumor suppressor protein-related epitope-containing peptides. In general, these methods will include first obtaining a sample suspected of containing such a protein, peptide or antibody, contacting the sample with an antibody or peptide in accordance with the present invention, as the case may be, under conditions effective to allow the formation of an immunocomplex, and then detecting the presence of the immunocomplex.

In general, the detection of immunocomplex formation is quite well known in the art and may be achieved through the application of numerous approaches. For example, the present invention contemplates the application of ELISA, RIA, immunoblot (e.g., dot blot), indirect immunofluorescence techniques and the like. Generally, immunocomplex formation will be detected through the use of a label, such as a radiolabel or an enzyme tag (such as alkaline phosphatase, horseradish peroxidase, or the like). Of course, one may find additional advantages through the use of a secondary binding ligand such as a second antibody or a biotin/avidin ligand binding arrangement, as is known in the art.

For assaying purposes, it is proposed that virtually any sample suspected of comprising either a tumor suppressor protein or peptide or a tumor suppressor protein-related peptide or antibody sought to be detected, as the case may be, may be employed. It is contemplated that such embodiments may have application in the titering of antigen or antibody samples, in the selection of hybridomas, and the like. In related embodiments, the present invention contemplates the preparation of kits that may be employed to detect the presence of tumor suppressor proteins or related peptides and/or antibodies in a sample. Samples may include cells, cell supernatants, cell suspensions, cell extracts, enzyme fractions, protein extracts, or other cell-free compositions suspected of containing tumor suppressor proteins or peptides. Generally speaking, kits in accordance with the present invention will include a suitable tumor suppressor protein, peptide or an antibody directed against such a protein or peptide, together with an immunodetection reagent and a means for containing the antibody or antigen and reagent. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, as noted above, a number of exemplary labels are known in the art and all such labels may be employed in connection with the present invention.

The container will generally include a vial into which the antibody, antigen or detection reagent may be placed, and preferably suitably aliquotted. The kits of the present invention will also typically include a means for containing the antibody, antigen, and reagent containers in close confinement for commercial sale. Such containers may include injection or blow-molded plastic containers into which the desired vials are retained.

2.8 NOEY2-Derived Epitopic Sequences

The present invention is also directed to NOEY2 protein or peptide compositions, free from total cells and other peptides, which comprise a purified NOEY2 protein or peptide which incorporates an epitope that is immunologically cross-reactive with one or more anti-tumor suppressor protein antibodies. In particular, the invention concerns epitopic core sequences derived from NOEY2 and NOEY2-derived proteins or peptides.

As used herein, the term "incorporating an epitope(s) that is immunologically cross-reactive with one or more anti-tumor suppressor protein antibodies" is intended to refer to a peptide or protein antigen which includes a primary, secondary or tertiary structure similar to an epitope located within a tumor suppressor protein or polypeptide. The level of similarity will generally be to such a degree that monoclonal or polyclonal antibodies directed against the tumor suppressor protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of NOEY2 immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, e.g., Jameson and Wolf, 1988; Wolf et al., 1988; U.S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic tumor suppressor protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to tumor suppressor proteins, and in particular NOEY2 and NOEY2-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the tumor suppressor protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquotted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

3.0 BRIEF DESCRIPTION OF THE DRAWINGS

The following drawings form part of the present specification and are included to further demonstrate certain aspects of the present invention. The invention may be better understood by reference to one or more of these drawings in combination with the detailed description of specific embodiments presented herein.

FIG. 1A. Complete NOEY2 cDNA nucleotide sequence (SEQ ID NO:1) and the deduced amino acid sequence (SEQ ID NO:2) of the NOEY2 protein. An asterisk indicates the stop codon.

FIG. 1B. Continuation of sequence of Complete NOEY2 cDNA nucleotide sequence (SEQ ID NO:1) and the deduced amino acid sequence (SEQ ID NO:2) of the NOEY2 protein.

FIG. 2. The pairwise amino acid sequence comparisons of NOEY2 with Ras and Rap family members. Four GDP/GTP binding domains and the CAAX motif are indicated by underlining. The bold type indicates residues conserved in nearly all GTPases.

FIG. 3A. Northern blot analysis of NOEY2 in cells and tissues. NOEY2 cDNA probe was labeled with $^{32}$P-dCTP by random primer. Fifteen micrograms of total cellular RNA was separated in 1.2% formaldehyde-agarose gels and immobilized on a Hybond-N$^+$ membrane (Amersham) by standard capillary transfer and UV crosslinking, and then prehybridized and hybridized to NOEY2 probe in 50% formamide, 1×SSC, 10× Denhardt's solution, 10 mM EDTA, 0.1% SDS and 300 µg/ml denatured salmon sperm DNA at 42° C. for 24 h. Hybridization of the same blot to a probe for 18S-rRNA indicates an equal amount of RNA in all lanes. OSE cells (lane 1 to 3) and ovarian cancer cell lines (lane 4 to 9). The primary normal OSE cells culture were obtained by gently scraping the surface of the ovaries which were from the patients undergoing surgery for nonmalignant gynecological diseases. The scraped epithelial cells were cultured in OSE medium (MCDB105/199 medium supplemented with 15% fetal calf serum and 10 ng/ml Epidermal Growth Factor). OSE cells were stained by antibody against cytokeratins. Ovarian cancer cell lines culture was as described before (Kruk et al., 1990).

Figure 3B:
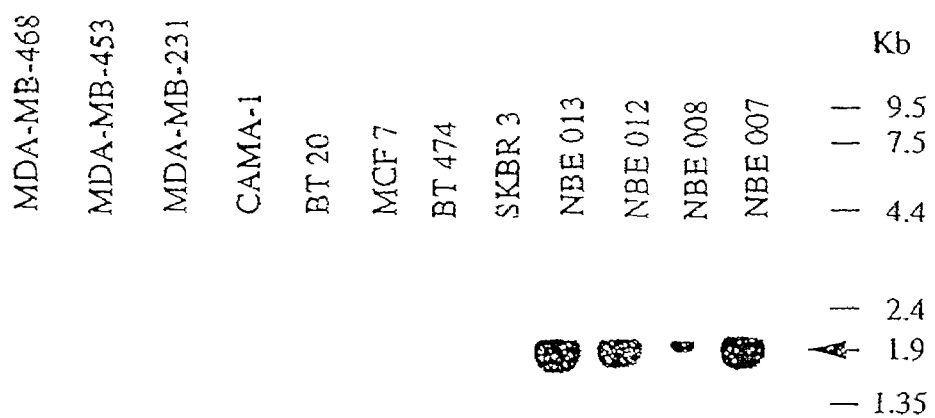

FIG. 3B. Normal breast epithelial cells (NBE) cancer cell lines (lanes 1 to 4) and breast cancer cell lines (lanes 5 to 12).

Figure 3C:
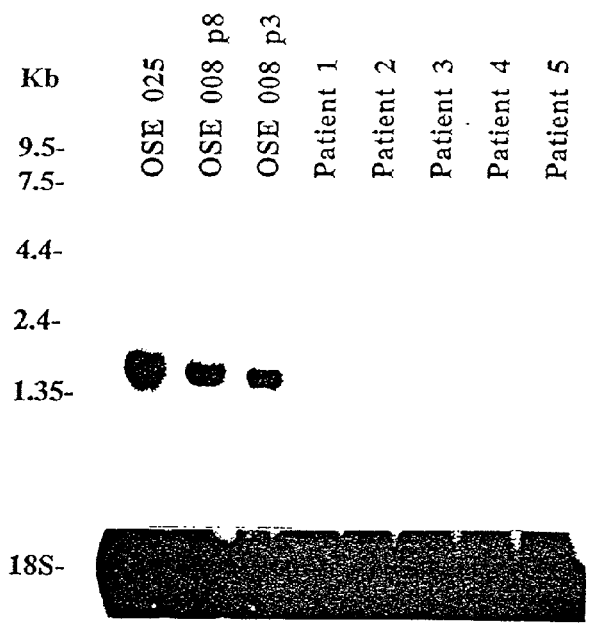

FIG. 3C. OSE cells (lane 1 to 3) and ovarian cancer patients' ascites cells (lane 4 to 9). Ovarian cancer cells primary cultures were obtained by separating tumor cells from ovarian cancer patients' ascites. Patients' ascites cells were thawed, centrifuged and resuspended in 2 ml stock Iso-osmotic Percoll (SIP) and placed in 15 ml tubes, then using Pasteur pipettes, 2 ml each of five different diluted SIP (the densities were 1.070, 1.058, 1.047, 1.035 and 1.023) were carefully layered to form a gradient. Gradients were centrifuged at 1500 rpm for 20 min using a swinging bucket centrifuge. Most ascites samples contain tumor cells that fraction near the second and third interfaces of the percoll gradient. H & E stains were performed to check the composition of the fractions. After processing ascites by percoll density gradient, further purification was obtained using magnetic beads coated with CD45. The purified cancer cells were stained by five monoclonal antibodies which specifically reacted with ovarian cancer antigens.

Figure 3D:
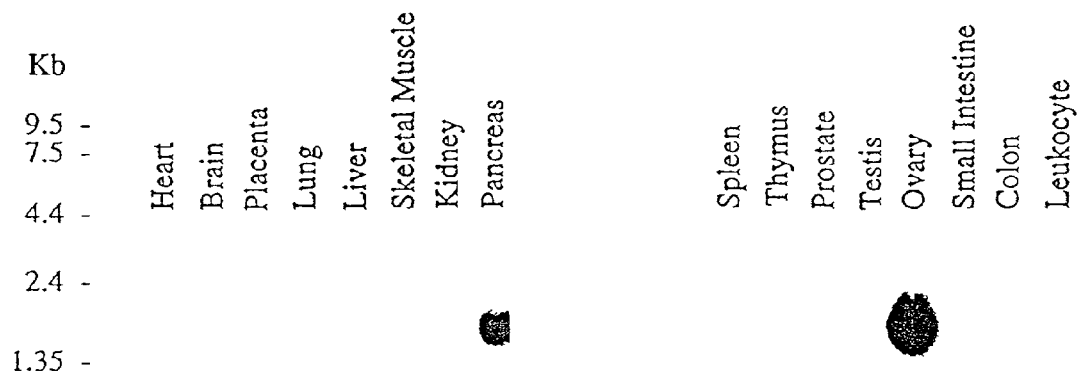

FIG. 3D. Multiple human tissues (Clonetech). 2 µg poly-RNA each line. Hybridization was done according to the methods of the manufacturer.

Figure 3E:
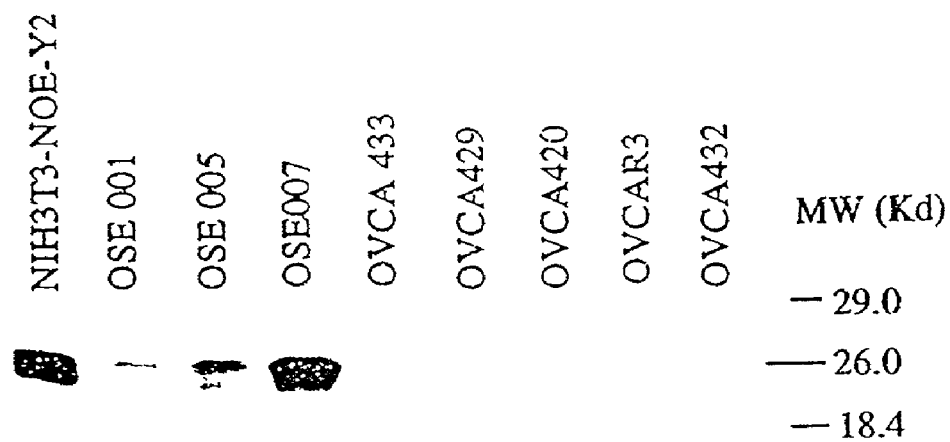

FIG. 3E. Western blot of 26-kDa protein, NIH3T3-NOEY2 (positive control (lane 1), OSE (lanes 2 to 4), ovarian cancer cell lines (lanes 5 to 9).

FIG. 4A. NOEY2-induced growth inhibition of ovarian and breast cancer cell lines. Colony formation after NOEY2 cDNA transfection. (a. Carrier DNA only; b. pcDNA3 vector only; c. pcDNA3 vector with NOEY2 in the antisense orientation; d. pcDNA3 vector with NOEY2 in the sense orientation).

FIG. 4B. NOEY2-induced growth inhibition of ovarian and breast cancer cell lines. Inhibition of cyclin D1 promoter activity in Saos-2, NIH3T3, SKBr3 and Hey cells. NOEY2 sense and antisense constructs were co-transfected with a luciferase reporter under the control of the human cyclin D1 promoter (Albanese et al., 1995). Luciferase activity measured in cells transfected with the sense construct was expressed as a percentage of activity measured in cells transfected with the antisense. The results were from representative studies performed in triplicate.

Figure 5A:
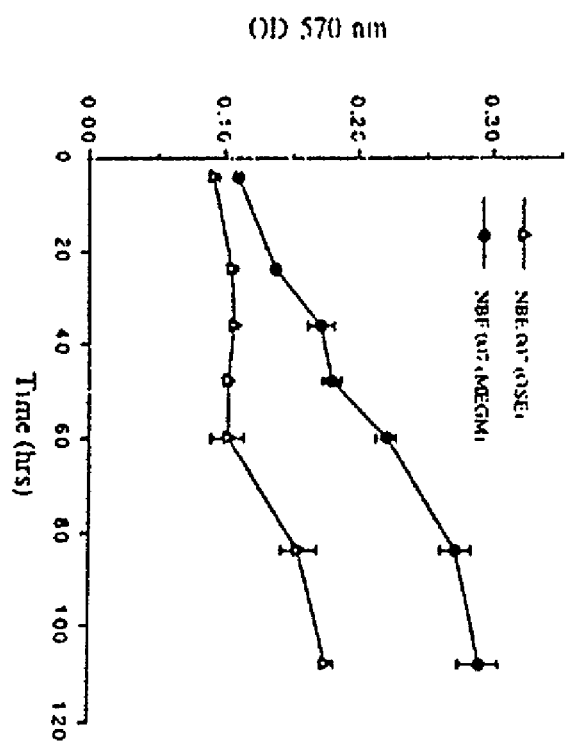

FIG. 5A. NBE 007 cell proliferation as measured by MTT (Ferrari et al., 1990). Primary cultures of NBE 007 were grown under two conditions: OSE medium or MEGM medium (Clonetics) which contains EGF, insulin, hydrocortisone and BPE.

Figure 5B:
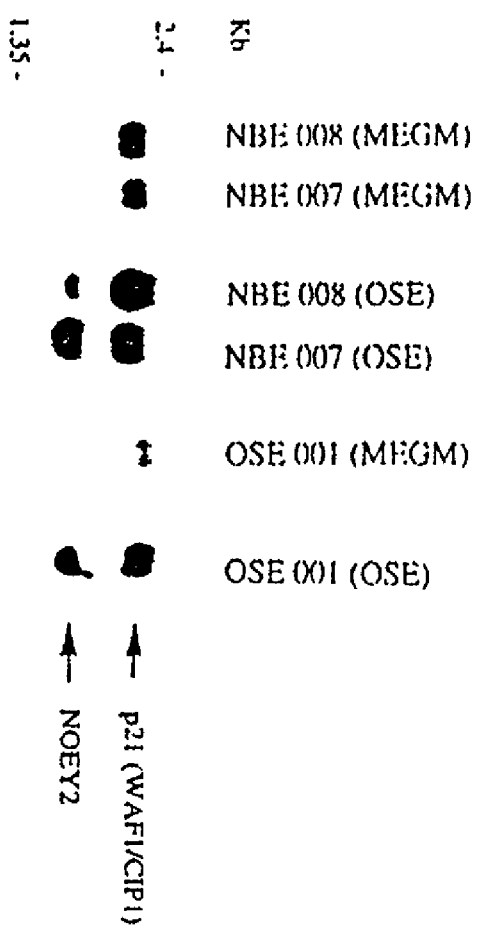

FIG. 5B. Expression of NOEY2 and p21$^{WAF1/CIP1}$ in OSE and NBE cultures as assessed by Northern analysis.

FIG. 6A. Induction of p$_{21}$$^{WAF1/CIP1}$ expression by HA-NOEY2.

FIG. 6B. Induction of p$_{21}$$^{WAF1/CIP1}$ expression by HA-NOEY2. HA-NOEY2 transfectants.

FIG. 6C. HA-Erk2 transfectants. P21$^{WAF1/CIP1}$ indicated in green (FITC).

FIG. 6D. HA indicated in red (rhodamine).

Figure 7:
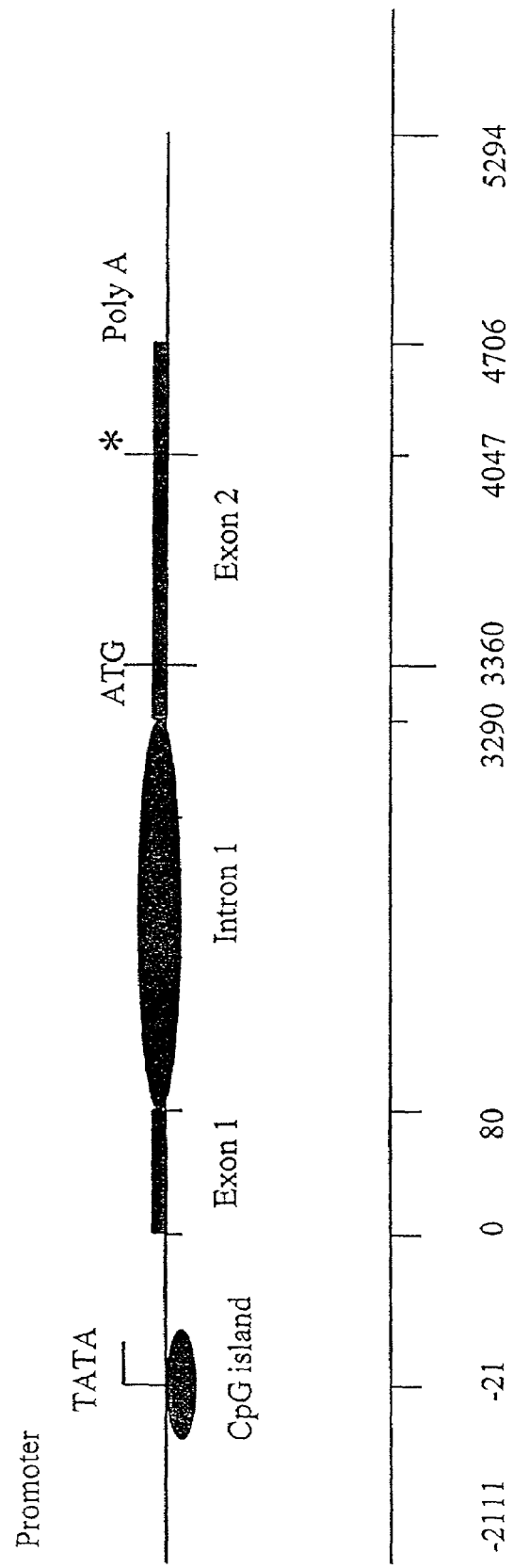

FIG. 7. Map of the genomic structure of NOEY2. Exons 1 and 2 are show as well as the large intron 1. Nucleotide residue numbers are shown below.

Figure 8:
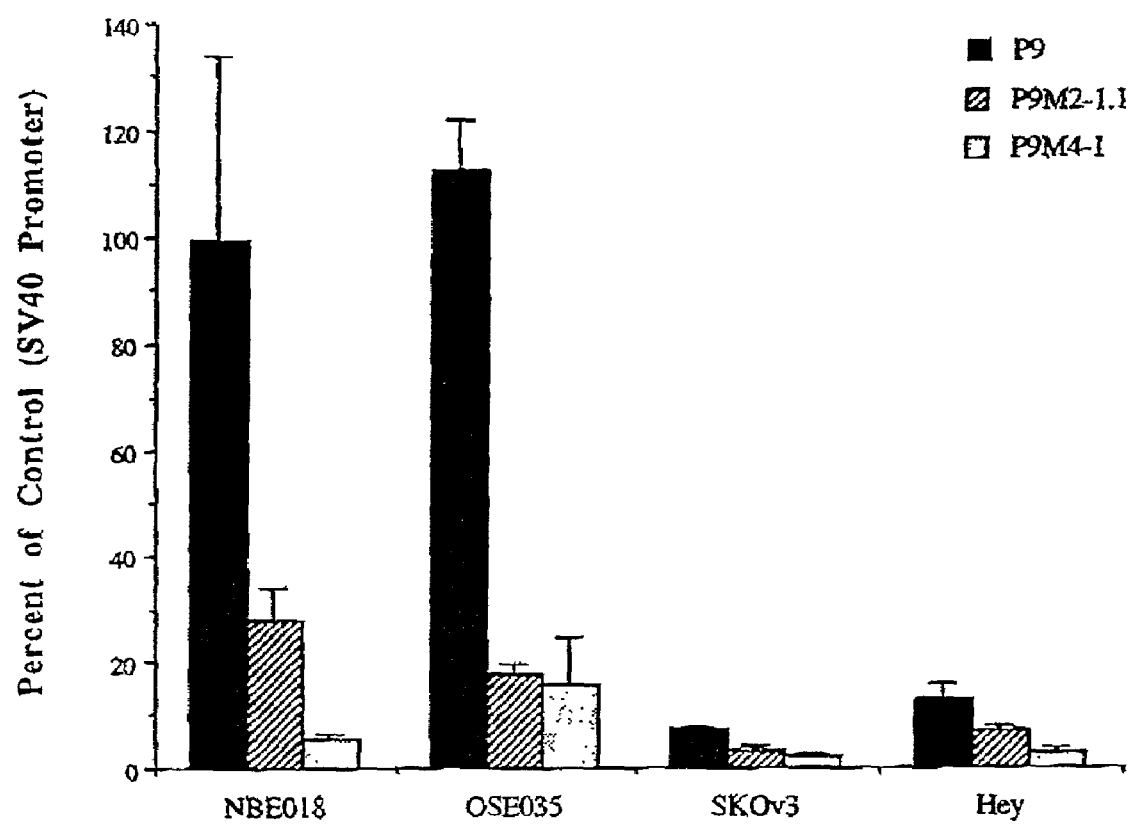

FIG. 8. Expression in OSE.NBE and ovarian cancer cell lines (SKOv3 and Hey) of the wild type NOEY2 promoter linked to a luciferase reporter (p9) and the NOEY2 promoter with an A to G mutation at −750 (p9m 2-1.1 and p9m 4-1. An A to G mutation was introduced into the wild type NOEY2 promoter by site directed mutagenesis. The results are from representative studies performed in triplicate.

4.0 DESCRIPTION OF ILLUSTRATIVE EMBODIMENTS

4.1 Molecular Alterations in Epithelial Ovarian Cancer

Studies from the inventors' group (Jacobs et al., 1992) and others (Mok et al., 1992; Li et al., 1993) have demonstrated that more than 90% of epithelial ovarian cancers are clonal based on the similarity of X-chromosome inactivation, p53 mutation and loss of heterozygosity in the primary tumor and different metastases. If this is the case, multiple mutations must occur within a single epithelial cell to produce malignant transformation. Mutations can be carried in the germ line or occur somatically. Germline mutation of several genes has recently been implicated in familial ovarian cancer including BRCA1 (Miki et al., 1994), BRCA2 (Wooster et al., 1994) mismatch repair genes (Lynch et al., 1996) and, on rare occasions, p53 (Malkin et al., 1990). For more than a decade the inventors' laboratory has focused on defining the somatic changes that distinguish malignant from benign ovarian epithelium (Bast et al., 1992). With Larry Feig and Geoff Cooper, the inventors had found a mutant Ki-Ras gene in ovarian cancer cells, but not in benign mesothelial cells from the same patient's ascites (Feig et al., 1984), demonstrating somatic mutation of Ras in a human tumor. Subsequent studies have found mutated or amplified Ki-, Ha- or N-Ras in less than 15% of ovarian cancers, most notably in mucinous or borderline lesions. Interestingly, as described below, Ras is constitutively activated in a significant fraction of ovarian cancer cell lines in the absence of mutation or amplification. In such cancers, signaling can be documented through the MAP kinase pathway and the ets-2 transcription factor, possibly accounting for the larger fraction of ovarian cancers that overexpress c-myc and other Ras-responsive genes such as urokinase plasminogen activator and matrix metalloproteinases that are important for invasion.

Physiologic activation of Ras implies that receptors and/or transducing molecules upstream are activated. A number of autocrine and paracrine growth regulatory pathways have been identified that appear to be altered in epithelial ovarian cancers when compared to normal ovarian epithelium. The EGFR family (EGFR, HER-2, HER-3, HER-4) of tyrosine kinase growth factor receptors may be particularly important in ovarian cancer. Normal ovarian surface epithelium expresses EGFR and can be stimulated to proliferate with exogenous EGF or TGF-(Rodriguez et al., 1991). Ovarian carcinomas retain EGFR in 70% of cases (Berchuck et al., 1991) and can secrete EGF and TGF-. Evidence for autocrine growth regulation has been obtained by inhibiting proliferation of ovarian cancer cell lines with anti-TGF- antibodies both in vitro and in vivo (Stromberg et al., 1992; Morishige et al., 1991). The inventors have demonstrated that loss of EGFR expression by tumor cells is associated with a slight, but statistically significant improvement in survival (Berchuck et al., 1991), consistent with loss of autocrine growth stimulation. Overexpression of HER-2 (c-erbB2) has been observed in 30% of cases of ovarian cancer. In stage III disease, overexpression of HER-2 is associated with a significantly shortened survival (Berchuck et al., 1990), although the significance of this marker in early stage disease is less certain (Rubin et al., 1993; Kacinski et al., 1992). Expression of HER-3 is increased in some borderline and early invasive ovarian tumors. Little has been reported regarding HER-4 in clinical material. Studies in cell culture suggest that the ligands heregulin and neu differentiating factor (NDF) signal through homodimers of HER-4 or heterodimers containing of HER-2/HER-3 or HER-2/HER-4. Cross-talk between the EGFR family members has been described. The inventors' own studies suggest that the ratio of HER-2/HER-3 may be particularly important in determining whether growth of tumor cells is stimulated or inhibited by heregulin. Counterintuitively, heregulin and NDF can inhibit, rather than stimulate clonogenic growth of ovarian and breast cancer cells that overexpress HER-2 in the presence of modest levels of HER-3 or HER-4 (Xu et al., 1996). Although tumor cells that overexpress HER-2 are growth inhibited by these ligands or by agonistic antibodies that bind only to HER-2, both ligands and antibodies can stimulate the ability of ovarian or breast cancer cells to invade matrigel membranes, associated with increased expression of matrix metalloproteinase 9 (MMP9) (Xu et al., 1994). Consequently, overexpression of HER-2 may potentiate the ability of tumor cells to invade and metastasize rather than to proliferate.

Other tyrosine kinase growth factor receptors have been identified in ovarian cancers that can signal through Ras and other pathways. Normal ovarian surface epithelium expresses little, if any of the fms tyrosine kinase growth factor receptor and secretes low levels of its ligand macrophage colony stimulating factor (M-CSF or CSF-1) (Lidor et al., 1993). Approximately 50% of ovarian cancers express fms (Kacinski, 1995) and 70% secrete substantial levels of M-CSF (Xu et al., 1991), consistent with possible autocrine growth stimulation through the Ras pathway. In addition, M-CSF is a potent chemoattractant for macrophages (Dorsch et al., 1993) which release a number of cytokines with growth regulatory activity for normal and transformed ovarian epithelium including tumor necrosis factor alpha (TNF-α), IL-1 and IL-6 (Wu et al., 1992). In the context of this P01, Dr. Mills (Project 4) is studying OCAF, a novel lysophospholipid growth factor that is present in ascites fluid from a majority of ovarian cancer patients and stimulates tumor growth in more than 90% of cases. OCAF activates the MAP kinase pathway through a cascade involving Ras and tyrosine kinases. Dr. Skinner (Project 1) is evaluating the role of several peptide factors including KGF, HGF and kit ligand that activate receptors which can also impinge on the Ras pathway.

Growth inhibition of ovarian surface epithelium is mediated by TGF-(Berchuck et al., 1992) and other factors elaborated by the underlying stroma (Karlan et al., 1995). The inventors' group has shown that TGF-1 and 2 can be expressed by and activated in normal ovarian epithelial cells consistent with autocrine as well as paracrine growth inhibition (Berchuck et al., 1992). Different ovarian cancer cell lines have lost the ability to express, activate or respond to TGF-(Berchuck et al., 1992), but more than 90% ovarian cancer ascites tumor specimens can inhibited by TGF-and a fraction undergo apoptosis (Hurteau et al., 1994). By contrast, normal epithelial cells can be growth inhibited but do not undergo apoptosis in response to TGF-(Havrilesky et al., 1995). Consequently, TGF- may provide a primitive surveillance mechanism for eliminating epithelial cells as they transform. Expression of TGF- is lost in up to 40% of ovarian cancer specimens that presumably would have lost autocrine growth inhibition, but paracrine growth inhibition and induction of apoptosis could be obtained from TGF- secreted by the underlying stroma.

Other candidates for negative growth regulation of ovarian epithelial cells include the protein tyrosine phosphatases (PTPs) that can deactivate or reverse the effects of certain tyrosine kinases. PTPs can, however, stimulate as well as inhibit growth of cells in different lineages. The inventors' group has cloned fragments of 13 PTPs from ovarian cancers (Wiener et al., 1996). PTP-1C and PTP-2A were regularly expressed in normal epithelial cells, but not expressed in a fraction of tumors, whereas PTP-1B, PTP- and PTP-H are upregulated in response to transfection of HER-2 (Wiener et al., 1996). Evidence is mounting for the potential role of PTP-1C as a tumor suppressor in several different cell lineages (Shultz et al, 1993) and the inventors' own data indicate that expression of PTP-1C inhibits growth of ovarian cancer cells. In clinical material a correlation has been observed between expression of PTP-1B and that of EGFR, HER-2 and fms (Wiener et al., 1994). In experimental systems PTP-1B can suppress transformation induced by expression of mutant HER-2 (Brown-Shiner et al., 1992). Overexpression of PTP-1B may reflect an inadequate homeostatic mechanism in ovarian carcinomas that have persistent or increased expression of tyrosine kinases such as EGFR, HER-2 and fms. Alternatively, the PTP-1B promoter may contain response elements for signaling pathways activated by tyrosine kinase receptors.

4.2 Tumor Suppressor Genes in Epithelial Ovarian Cancer

As in cancers that arise at other sites, the tumor suppressor gene best studied in ovarian cancer is p53 which is mutated in approximately 50% of metastatic tumors, but in only 15% of lesions in stage IA or IB (Berchuck et al., 1994). The gene is rarely affected in benign or borderline lesions. As the inventors had shown with Drs. Matt Kohler and Andrew Berchuck, the pattern of p53 mutation is most consistent with spontaneous deamination during normal replication rather than formation of adducts with exogenous carcinogens (Kohler et al., 1993). Loss of heterozygosity at RB has been observed in a fraction of ovarian cancers, but functional RB protein is generally present.

Aside from p53 and RB, little is known about the role of many of the previously identified tumor suppressor genes in ovarian cancer. Moreover, no suppressor gene specific to ovarian cancer has been isolated. Although a number of approaches have been used to identify putative tumor suppressor genes, the inventors have utilized differential display of mRNA by means of the polymerase chain reaction (DDPCR™) to isolate NOEY2, a novel Ras-related gene, that may serve as a tumor suppressor gene in ovarian cancer. A substantial literature has addressed the possibility that Ras-related genes might inhibit Ras function directly or indirectly.

4.3 RAS and RAP Families

A large superfamily (>50 members) of monomeric GTP-binding proteins structurally related to the Ras oncogene proteins has been described in the past few years. The model of action of Ras has recently been intensively investigated, and one of its direct downstream target molecules has been identified to be c-raf-1, which induces the activation of the MAP kinase/ERK through MEK. The Rap family consists of several highly homologous members—Rap1A, Rap1B, and Rap2—that belong to the Ras superfamily of small GTP-binding proteins (Pizon et al., 1988). Rap1A and/or Rap1B have been shown to antagonize the Ras Functions, such as the Ki-Ras-induced transformation of NIH 3T3 cells (Kitayama et al., 1989), the Ha-Ras-induced germinal vesicle breakdown in *Xenopus* oocytes (Campa et al., 1991), the N-Ras-inhibited muscarinic K$^+$ channel activity (Yatani et al., 1991), the Ki-Ras-induced activation of the c-fos promoter/enhancer in NIH 3T3 cells (Sakoda et al., 1992), the proliferation of middle T antigen-transformed Rat-2 cells (Jelinek and Hassell, 1992), and the Ha-Ras-induced activation of the c-Raf-1 protein kinase-dependent Map kinase cascade in Rat-1 cells (Cook et al., 1993). Rap1A and/or Rap1B have been shown to be phosphorylated by protein kinase A in both intact cells and cell-free systems (Quilliam et al., 1991), by Ca$^{2+}$/calmodulin-dependent protein kinase Gr in a cell-free system (Sahyoun et al., 1991), and by protein kinase G in a cell-free system (Miura et al., 1992). The protein kinase A-catalyzed phosphorylation sites of Rap1A and Rap1B are Ser 180 and Ser 179, respectively, in their C-terminal regions (Quilliam et al., 1991; Hata et al., 1991). This phosphorylation of Rap1B lowers its membrane binding activity and induces its translocation from the membrane to the cytosol (Hata et al., 1991). The phosphorylation of Rap1B makes it sensitive to the action of 5 mg GDS to stimulate its GDP/GTP exchange reaction (Hata et al., 1991). These observations suggest that Rap1 has multiple functions, but the mode of action of Rap1 at a molecular level remains to be clarified. Of particular interest is the possibility that Rap family members may not only antagonize Ras, but also signal independent of the Ras pathway.

The GTP binding site of Ras proteins consists of four non-contiguous regions encountered in all the proteins of the Ras superfamily. Among these regions six amino acids: DTAGQE, in positions 57 to 62 of the K-Ras protein, seemed to be a hallmark of all the Ras and Ras-related proteins. It is known that single amino acid substitution in p21Ras at aa12 (glycine), 13 (glycine) and 61 (glutamine) significantly reduce the intrinsic GTPase activity of Ras proteins and prevent Ras-GAP from accelerating the rate of GTP hydrolysis. Therefore, it appears that this domain plays an essential role in the control of the biological properties of the Ras proteins. Random mutagenesis studies also shown that amino acid substitutions at positions 59 and 63 can activate Ras transforming potential.

4.4 Loss of Heterozygosity in Ovarian Cancers

Based upon the paradigm of the RB gene, LOH has been observed within cancers at the site of deleted tumor suppressor genes. Numerous studies of loss of heterozygosity (LOH) in ovarian carcinoma have been published since 1989 and are all largely based on techniques using normal-tumor pairs. Sites of LOH have been reported on 1p, 3p, 4p, 6p, 7p, 8q, 11p, 13q, 17p, 17q, 18q and 22. Studies have detected LOH at sites distal to BRCA1 on chromosome 17q (Hacibs et al., 1993) and at the BRCA2 site on chromosome 13q. The short arm of chromosome 1 is frequently affected by rearrangements in a variety of human malignancies. Genetic alterations, predominantly deletions, which are indicative of the presence of a putative tumor suppressor gene at chromosome 1p, are observed in ovarian and breast cancer. Dr. Gray (Project 3) has detected LOH at 1p31 in ovarian cancer, as has Drs. John Lancaster and Andrew Berchuck. In breast cancer LOH is found at 1p31 (Stromberg et al., 1992) in 28% to 50% of cases (Nagai et al., 1995; Loupart et al., 1995; Hoggard et al., 1995). In addition to NOEY2, several other genes map to chromosome 1p31-32 that could suppress growth, including VCAM-1 which functions as an adhesion molecule and p18 which inhibits the cyclin D-CDK6 complex.

4.5 Protein Isolation and Purification

In certain embodiments it may be desirable to purify NOEY2 polypeptides, NOEY2 epitopes, NOEY2-derived peptide fragments, or variants thereof. Protein purification techniques are well known to those of skill in the art. These techniques involve, at one level, the crude fractionation of the cellular milieu to polypeptide and non-polypeptide fractions. Having separated the polypeptide from other proteins, the polypeptide of interest may be further purified using chromatographic and electrophoretic techniques to achieve partial or complete purification (or purification to homogeneity). Analytical methods particularly suited to the preparation of a pure peptide are ion-exchange chromatography, exclusion chromatography; polyacrylamide gel electrophoresis; isoelectric focusing. A particularly efficient method of purifying peptides is fast protein liquid chromatography or even HPLC.

Certain aspects of the present invention concern the purification, and in particular embodiments, the substantial purification, of an encoded protein or peptide. The term "purified protein or peptide" as used herein, is intended to refer to a composition, isolatable from other components, wherein the protein or peptide is purified to any degree relative to its naturally-obtainable state. A purified protein or peptide therefore also refers to a protein or peptide, free from the environment in which it may naturally occur.

Generally, "purified" will refer to a protein or peptide composition that has been subjected to fractionation to remove various other components, and which composition substantially retains its expressed biological activity. Where the term "substantially purified" is used, this designation will refer to a composition in which the protein or peptide forms the major component of the composition, such as constituting about 50%, about 60%, about 70%, about 80%, about 90%, about 95% or more of the proteins in the composition.

Various methods for quantifying the degree of purification of the protein or peptide will be known to those of skill in the art in light of the present disclosure. These include, for example, determining the specific activity of an active fraction, or assessing the amount of polypeptides within a fraction by SDS/PAGE analysis. A preferred method for assessing the purity of a fraction is to calculate the specific activity of the fraction, to compare it to the specific activity of the initial extract, and to thus calculate the degree of purity, herein assessed by a "-fold purification number." The actual units used to represent the amount of activity will, of course, be dependent upon the particular assay technique chosen to follow the purification and whether or not the expressed protein or peptide exhibits a detectable activity.

Various techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite and affinity chromatography; isoelectric focusing; gel electrophoresis; and combinations of such and other techniques. As is generally known in the art, it is believed that the order of conducting the various purification steps may be changed, or that certain steps may be omitted, and still result in a suitable method for the preparation of a substantially purified protein or peptide.

There is no general requirement that the protein or peptide always be provided in their most purified state. Indeed, it is contemplated that less substantially purified products will have utility in certain embodiments. Partial purification may be accomplished by using fewer purification steps in combination, or by utilizing different forms of the same general purification scheme. For example, it is appreciated that a cation-exchange column chromatography performed utilizing an HPLC apparatus will generally result in a greater "-fold" purification than the same technique utilizing a low pressure chromatography system. Methods exhibiting a lower degree of relative purification may have advantages in total recovery of protein product, or in maintaining the activity of an expressed protein.

It is known that the migration of a polypeptide can vary, sometimes significantly, with different conditions of SDS/PAGE (Capaldi et al., 1973; Capaldi et al., 1974; Capaldi et al., 1977). It will therefore be appreciated that under differing electrophoresis conditions, the apparent molecular weights of purified or partially purified expression products may vary.

High performance liquid chromatography (HPLC) is characterized by a very rapid separation with extraordinary resolution of peaks. This is achieved by the use of very fine particles and high pressure to maintain an adequate flow rate. Separation can be accomplished in a matter of min, or at most an h. Moreover, only a very small volume of the sample is needed because the particles are so small and close-packed that the void volume is a very small fraction of the bed volume. Also, the concentration of the sample need not be very great because the bands are so narrow that there is very little dilution of the sample.

Gel chromatography, or molecular sieve chromatography, is a special type of partition chromatography that is based on molecular size. The theory behind gel chromatography is that the column, which is prepared with tiny particles of an inert substance that contain small pores, separates larger molecules from smaller molecules as they pass through or around the pores, depending on their size. As long as the material of which the particles are made does not adsorb the molecules, the sole factor determining rate of flow is the size. Hence, molecules are eluted from the column in decreasing size, so long as the shape is relatively constant. Gel chromatography is unsurpassed for separating molecules of different size because separation is independent of all other factors such as pH, ionic strength, temperature, etc. There also is virtually no adsorption, less zone spreading and the elution volume is related in a simple matter to molecular weight.

Affinity chromatography is a chromatographic procedure that relies on the specific affinity between a substance to be isolated and a molecule that it can specifically bind to. This is a receptor-ligand type interaction. The column material is synthesized by covalently coupling one of the binding partners to an insoluble matrix. The column material is then able to specifically adsorb the substance from the solution. Elution occurs by changing the conditions to those in which binding will not occur (alter pH, ionic strength, temperature, etc.).

A particular type of affinity chromatography useful in the purification of carbohydrate containing compounds is lectin affinity chromatography. Lectins are a class of substances that bind to a variety of polysaccharides and glycoproteins. Lectins are usually coupled to agarose by cyanogen bromide. Conconavalin A coupled to Sepharose was the first material of this sort to be used and has been widely used in the isolation of polysaccharides and glycoproteins other lectins that have been include lentil lectin, wheat germ agglutinin which has been useful in the purification of N-acetyl glucosaminyl residues and *Helix pomatia* lectin. Lectins themselves are purified using affinity chromatography with carbohydrate ligands. Lactose has been used to purify lectins from castor bean and peanuts; maltose has been useful in extracting lectins from lentils and jack bean; N-acetyl-D-galactosamine is used for purifying lectins from soybean; N-acetylglucosamine binds to lectins from wheat germ; D-galactosamine has been used in obtaining lectins from clams and L-fucose will bind to lectins from lotus.

The matrix should be a substance that itself does not adsorb molecules to any significant extent and that has a broad range of chemical, physical and thermal stability. The ligand should be coupled in such a way as to not affect its binding properties. The ligand should also provide relatively tight binding. And it should be possible to elute the substance without destroying the sample or the ligand. One of the most common forms of affinity chromatography is immunoaffinity chromatography. The generation of antibodies that would be suitable for use in accord with the present invention is discussed below.

4.6 Synthetic NOEY2 and NOEY2-Derived Peptides

To achieve certain objectives of the invention, it is desirable to prepare NOEY2-derived peptides and polypeptide fragments for use in various diagnostic and therapeutic applications. Because of their relatively small size, the peptides of the invention can also be synthesized in solution or on a solid support in accordance with conventional techniques. Various automatic synthesizers are commercially available and can be used in accordance with known protocols. See, for example, Stewart and Young, (1966); Voss et al., (1983); Merrifield, (1986); and Barany and Merrifield (1979), each incorporated herein by reference. Short peptide sequences, or libraries of overlapping peptides, usually from about 6 or so amino acids, and up to and including about 35 to 50 or so amino acids, which correspond to the selected regions described herein, can be readily synthesized and then screened in screening assays designed to identify reactive peptides. Alternatively, recombinant DNA technology may be employed wherein a nucleotide sequence which encodes a peptide of the invention is inserted into an expression vector, transformed or transfected into an appropriate host cell and cultivated under conditions suitable for expression.

4.7 NOEY2-Derived Antigen Compositions

The present invention also provides for the use of NOEY2 proteins or peptides as antigens for the immunization of animals relating to the production of antibodies. It is envisioned that either NOEY2, or portions thereof, will be coupled, bonded, bound, conjugated or chemically-linked to one or more agents via linkers, polylinkers or derivatized amino acids. This may be performed such that a bispecific or multivalent composition or vaccine is produced. It is further envisioned that the methods used in the preparation of these compositions will be familiar to those of skill in the art and should be suitable for administration to animals, i.e., pharmaceutically acceptable. Preferred agents are the carriers are keyhole limpet hemocyannin (KLH) or bovine serum albumin (BSA).

4.8 Antisense Constructs

In some cases, mutant tumor suppressors may not be non-functional. Rather, they may have aberrant functions that cannot be overcome by replacement gene therapy, even where the "wild-type" molecule is expressed in amounts in excess of the mutant polypeptide. Therefore, an important aspect of the invention concerns the preparation and use of NOEY2 antisense constructs. Such antisense technology may be used to "knock-out" or reduce the function or expression of NOEY2 in a cell, or may ablate the function of NOEY2 in the development of cell line or in a transgenic mouse or other animal used in research, or diagnostic and/or screening methods.

The methodology for antisense techniques is well-known to molecular biologists. In a general sense, antisense methods take advantage of the fact that nucleic acids tend to pair with "complementary" sequences. By complementary, it is meant that polynucleotides are those which are capable of base-pairing according to the standard Watson-Crick complementarity rules. That is, the larger purines will base pair with the smaller pyrimidines to form combinations of guanine paired with cytosine (G:C) and adenine paired with either thymine (A:T) in the case of DNA, or adenine paired with uracil (A:U) in the case of RNA. Inclusion of less common bases such as inosine, 5-methylcytosine, 6-methyladenine, hypoxanthine and others in hybridizing sequences does not interfere with pairing.

Targeting double-stranded (ds) DNA with polynucleotides leads to triple-helix formation; targeting RNA will lead to double-helix formation. Antisense polynucleotides, when introduced into a target cell, specifically bind to their target polynucleotide and interfere with transcription, RNA processing, transport, translation and/or stability. Antisense RNA constructs, or DNA encoding such antisense RNA's, may be employed to inhibit gene transcription or translation or both within a host cell, either in vitro or in vivo, such as within a host animal, including a human subject.

Antisense constructs may be designed to bind to the promoter and other control regions, exons, introns or even exon-intron boundaries of a gene. It is contemplated that the most effective antisense constructs will include regions complementary to intron/exon splice junctions. Thus, it is proposed that a preferred embodiment includes an antisense construct with complementarity to regions within 50–200 bases of an intron-exon splice junction. It has been observed that some exon sequences can be included in the construct without seriously affecting the target selectivity thereof. The amount of exonic material included will vary depending on the particular exon and intron sequences used. One can readily test whether too much exon DNA is included simply by testing the constructs in vitro to determine whether normal cellular function is affected or whether the expression of related genes having complementary sequences is affected.

As stated above, "complementary" or "antisense" means polynucleotide sequences that are substantially complementary over their entire length and have very few base mismatches. For example, sequences of fifteen bases in length may be termed complementary when they have complementary nucleotides at thirteen or fourteen positions. Naturally, sequences which are completely complementary will be sequences which are entirely complementary throughout their entire length and have no base mismatches. Other sequences with lower degrees of homology also are contemplated. For example, an antisense construct which has limited regions of high homology as well as non-homologous regions (e.g., ribozyme) could be designed. These molecules, though having less than 50% homology, would bind to target sequences under appropriate conditions. The preparation and use of such ribozymes are described in detail in the following section.

In some circumstances, it may be advantageous to combine portions of genomic DNA with cDNA or synthetic sequences to generate specific constructs. For example, where an intron is desired in the ultimate construct, a genomic clone will need to be used. The cDNA or a synthesized polynucleotide may provide more convenient restriction sites for the remaining portion of the construct and, therefore, would be used for the rest of the sequence.

4.9 Ribozymes

Another approach for addressing the "dominant negative" mutant tumor suppressor is through the use of ribozymes. Although proteins traditionally have been used for catalysis of nucleic acids, another class of macromolecules has emerged as useful in this endeavor. Ribozymes are RNA-protein complexes that cleave nucleic acids in a site-specific fashion. Ribozymes have specific catalytic domains that possess endonuclease activity (Kim and Cech, 1987; Gerlach et al., 1987; Forster and Symons, 1987). For example, a large number of ribozymes accelerate phosphoester transfer reactions with a high degree of specificity, often cleaving only one of several phosphoesters in an oligonucleotide substrate (Cech et al., 1981; Michel and Westhof, 1990; Reinhold-Hurek and Shub, 1992). This specificity has been attributed to the requirement that the substrate bind via specific base-pairing interactions to the internal guide sequence ("IGS") of the ribozyme prior to chemical reaction.

Ribozyme catalysis has primarily been observed as part of sequence-specific cleavage/ligation reactions involving nucleic acids (Joyce, 1989; Cech et al., 1981). For example, U.S. Pat. No. 5,354,855 (specifically incorporated herein by reference) reports that certain ribozymes can act as endonucleases with a sequence specificity greater than that of known ribonucleases and approaching that of the DNA restriction enzymes. Thus, sequence-specific ribozyme-mediated inhibition of gene expression may be particularly suited to therapeutic applications (Scanlon et al., 1991;

Sarver et al., 1990). Recently, it was reported that ribozymes elicited genetic changes in some cells lines to which they were applied; the altered genes included the oncogenes H-ras, c-fos and genes of HIV. Most of this work involved the modification of a target mRNA, based on a specific mutant codon that is cleaved by a specific ribozyme.

Six basic varieties of naturally-occurring enzymatic RNAs are known presently. Each can catalyze the hydrolysis of RNA phosphodiester bonds in trans (and thus can cleave other RNA molecules) under physiological conditions. In general, enzymatic nucleic acids act by first binding to a target RNA. Such binding occurs through the target binding portion of a enzymatic nucleic acid which is held in close proximity to an enzymatic portion of the molecule that acts to cleave the target RNA. Thus, the enzymatic nucleic acid first recognizes and then binds a target RNA through complementary base-pairing, and once bound to the correct site, acts enzymatically to cut the target RNA. Strategic cleavage of such a target RNA will destroy its ability to direct synthesis of an encoded protein. After an enzymatic nucleic acid has bound and cleaved its RNA target, it is released from that RNA to search for another target and can repeatedly bind and cleave new targets.

The enzymatic nature of a ribozyme is advantageous over many technologies, such as antisense technology (where a nucleic acid molecule simply binds to a nucleic acid target to block its translation) since the concentration of ribozyme necessary to affect a therapeutic treatment is lower than that of an antisense oligonucleotide. This advantage reflects the ability of the ribozyme to act enzymatically. Thus, a single ribozyme molecule is able to cleave many molecules of target RNA. In addition, the ribozyme is a highly specific inhibitor, with the specificity of inhibition depending not only on the base pairing mechanism of binding to the target RNA, but also on the mechanism of target RNA cleavage. Single mismatches, or base-substitutions, near the site of cleavage can completely eliminate catalytic activity of a ribozyme. Similar mismatches in antisense molecules do not prevent their action (Woolf et al., 1992). Thus, the specificity of action of a ribozyme is greater than that of an antisense oligonucleotide binding the same RNA site.

The enzymatic nucleic acid molecule may be formed in a hammerhead, hairpin, a hepatitis δ virus, group I intron or RNaseP RNA (in association with an RNA guide sequence) or *Neurospora* VS RNA motif. Examples of hammerhead motifs are described by Rossi et al. (1992). Examples of hairpin motifs are described by Hampel et al. (Eur. Pat. Appl. Publ. No. EP 0360257), Hampel and Tritz (1989), Hampel et al. (1990) and U.S. Pat. No. 5,631,359 (specifically incorporated herein by reference). An example of the hepatitis δ virus motif is described by Perrotta and Been (1992); an example of the RNaseP motif is described by Guerrier-Takada et al. (1983); *Neurospora* VS RNA ribozyme motif is described by Collins (Saville and Collins, 1990; Saville and Collins, 1991; Collins and Olive, 1993); and an example of the Group I intron is described in (U.S. Pat. No. 4,987,071, specifically incorporated herein by reference). All that is important in an enzymatic nucleic acid molecule of this invention is that it has a specific substrate binding site which is complementary to one or more of the target gene RNA regions, and that it have nucleotide sequences within or surrounding that substrate binding site which impart an RNA cleaving activity to the molecule. Thus the ribozyme constructs need not be limited to specific motifs mentioned herein.

In certain embodiments, it may be important to produce enzymatic cleaving agents which exhibit a high degree of specificity for the RNA of a desired target, such as one of the sequences disclosed herein. The enzymatic nucleic acid molecule is preferably targeted to a highly conserved sequence region of a target mRNA. Such enzymatic nucleic acid molecules can be delivered exogenously to specific cells as required. Alternatively, the ribozymes can be expressed from DNA or RNA vectors that are delivered to specific cells.

Small enzymatic nucleic acid motifs (e.g., of the hammerhead or the hairpin structure) may also be used for exogenous delivery. The simple structure of these molecules increases the ability of the enzymatic nucleic acid to invade targeted regions of the mRNA structure. Alternatively, catalytic RNA molecules can be expressed within cells from eukaryotic promoters (e.g., Scanlon et al., 1991; Kashani-Sabet et al., 1992; Dropulic et al., 1992; Weerasinghe et al., 1991; Ojwang et al., 1992; Chen et al., 1992; Sarver et al., 1990). Those skilled in the art realize that any ribozyme can be expressed in eukaryotic cells from the appropriate DNA vector. The activity of such ribozymes can be augmented by their release from the primary transcript by a second ribozyme (Int. Pat. Appl. Publ. No. WO 93/23569, and Int. Pat. Appl. Publ. No. WO 94/02595, both hereby incorporated by reference; Ohkawa et al., 1992; Taira et al., 1991; and Ventura et al., 1993).

Ribozymes may be added directly, or can be complexed with cationic lipids, lipid complexes, packaged within liposomes, or otherwise delivered to target cells. The RNA or RNA complexes can be locally administered to relevant tissues ex vivo, or in vivo through injection, aerosol inhalation, infusion pump or stent, with or without their incorporation in biopolymers.

Ribozymes may be designed as described in Int. Pat. Appl. Publ. No. WO 93/23569 and Int. Pat. Appl. Publ. No. WO 94/02595, each specifically incorporated herein by reference) and synthesized to be tested in vitro and in vivo, as described. Such ribozymes can also be optimized for delivery. While specific examples are provided, those in the art will recognize that equivalent RNA targets in other species can be utilized when necessary.

Hammerhead or hairpin ribozymes may be individually analyzed by computer folding (Jaeger et al., 1989) to assess whether the ribozyme sequences fold into the appropriate secondary structure. Those ribozymes with unfavorable intramolecular interactions between the binding arms and the catalytic core are eliminated from consideration. Varying binding arm lengths can be chosen to optimize activity. Generally, at least 5 or so bases on each arm are able to bind to, or otherwise interact with, the target RNA.

Ribozymes of the hammerhead or hairpin motif may be designed to anneal to various sites in the mRNA message, and can be chemically synthesized. The method of synthesis used follows the procedure for normal RNA synthesis as described in Usman et al. (1987) and in Scaringe et al. (1990) and makes use of common nucleic acid protecting and coupling groups, such as dimethoxytrityl at the 5'-end, and phosphoramidites at the 3'-end. Average stepwise coupling yields are typically >98%. Hairpin ribozymes may be synthesized in two parts and annealed to reconstruct an active ribozyme (Chowrira and Burke, 1992). Ribozymes may be modified extensively to enhance stability by modification with nuclease resistant groups, for example, 2'-amino, 2'-C-allyl, 2'-flouro, 2'-o-methyl, 2'-H (for a review see e.g., Usman and Cedergren, 1992). Ribozymes may be purified by gel electrophoresis using general methods or by high pressure liquid chromatography and resuspended in water.

Ribozyme activity can be optimized by altering the length of the ribozyme binding arms, or chemically synthesizing ribozymes with modifications that prevent their degradation by serum ribonucleases (see e.g., Int. Pat. Appl. Publ. No. WO 92/07065; Perrault et al, 1990; Pieken et al., 1991; Usman and Cedergren, 1992; Int. Pat. Appl. Publ. No. WO 93/15187; Int. Pat. Appl. Publ. No. WO 91/03162; Eur. Pat. Appl. Publ. No. 92110298.4; U.S. Pat. No. 5,334,711; and Int. Pat. Appl. Publ. No. WO 94/13688, which describe various chemical modifications that can be made to the sugar moieties of enzymatic RNA molecules), modifications which enhance their efficacy in cells, and removal of stem II bases to shorten RNA synthesis times and reduce chemical requirements.

Sullivan et al. (Int. Pat. Appl. Publ. No. WO 94/02595) describes the general methods for delivery of enzymatic RNA molecules. Ribozymes may be administered to cells by a variety of methods known to those familiar to the art, including, but not restricted to, encapsulation in liposomes, by iontophoresis, or by incorporation into other vehicles, such as hydrogels, cyclodextrins, biodegradable nanocapsules, and bioadhesive microspheres. For some indications, ribozymes may be directly delivered ex vivo to cells or tissues with or without the aforementioned vehicles. Alternatively, the RNA/vehicle combination may be locally delivered by direct inhalation, by direct injection or by use of a catheter, infusion pump or stent. Other routes of delivery include, but are not limited to, intravascular, intramuscular, subcutaneous or joint injection, aerosol inhalation, oral (tablet or pill form), topical, systemic, ocular, intraperitoneal and/or intrathecal delivery. More detailed descriptions of ribozyme delivery and administration are provided in Int. Pat. Appl. Publ. No. WO 94/02595 and Int. Pat. Appl. Publ. No. WO 93/23569, each specifically incorporated herein by reference.

Another means of accumulating high concentrations of a ribozyme(s) within cells is to incorporate the ribozyme-encoding sequences into a DNA expression vector. Transcription of the ribozyme sequences are driven from a promoter for eukaryotic RNA polymerase I (pol I), RNA polymerase II (pol II), or RNA polymerase III (pol III). Transcripts from pol II or pol III promoters will be expressed at high levels in all cells; the levels of a given pol II promoter in a given cell type will depend on the nature of the gene regulatory sequences (enhancers, silencers, etc.) present nearby. Prokaryotic RNA polymerase promoters may also be used, providing that the prokaryotic RNA polymerase enzyme is expressed in the appropriate cells (Elroy-Stein and Moss, 1990; Gao and Huang, 1993; Lieber et al., 1993; Zhou et al., 1990). Ribozymes expressed from such promoters can function in mammalian cells (e.g. Kashani-Saber et al., 1992; Ojwang et al., 1992; Chen et al., 1992; Yu et al., 1993; L'Huillier et al., 1992; Lisziewicz et al., 1993). Such transcription units can be incorporated into a variety of vectors for introduction into mammalian cells, including but not restricted to, plasmid DNA vectors, viral DNA vectors (such as adenovirus or adeno-associated vectors), or viral RNA vectors (such as retroviral, semliki forest virus, sindbis virus vectors).

Ribozymes of this invention may be used as diagnostic tools to examine genetic drift and mutations within diseased cells. They can also be used to assess levels of the target RNA molecule. The close relationship between ribozyme activity and the structure of the target RNA allows the detection of mutations in any region of the molecule which alters the base-pairing and three-dimensional structure of the target RNA. By using multiple ribozymes described in this invention, one may map nucleotide changes which are important to RNA structure and function in vitro, as well as in cells and tissues. Cleavage of target RNAs with ribozymes may be used to inhibit gene expression and define the role (essentially) of specified gene products in the progression of disease. In this manner, other genetic targets may be defined as important mediators of the disease. These studies will lead to better treatment of the disease progression by affording the possibility of combinational therapies (e.g., multiple ribozymes targeted to different genes, ribozymes coupled with known small molecule inhibitors, or intermittent treatment with combinations of ribozymes and/or other chemical or biological molecules). Other in vitro uses of ribozymes of this invention are well known in the art, and include detection of the presence of mRNA associated with an IL-5 related condition. Such RNA is detected by determining the presence of a cleavage product after treatment with a ribozyme using standard methodology.

4.10 Vectors for Cloning, Gene Transfer and Expression

In certain embodiments of the invention, expression vectors are employed to express a NOEY2 or NOEY2-derived polypeptide product, which can then be purified and, for example, be used to vaccinate animals, or to generate antisera or monoclonal antibodies which may be used in a variety of diagnostic and therapeutic applications. In other embodiments, an expression vector comprising a NOEY2 or NOEY2-derived polynucleotide may be used in gene therapy.

Expression requires that appropriate signals be provided in the vectors, and which include various regulatory elements, such as enhancers/promoters from both viral and mammalian sources that drive expression of the genes of interest in host cells. Elements designed to optimize messenger RNA stability and translatability in host cells also are defined. The conditions for the use of a number of dominant drug selection markers for establishing permanent, stable cell clones expressing the products are also provided, as is an element that links expression of the drug selection markers to expression of the polypeptide.

4.10.1 Regulatory Elements

Throughout this application, the term "expression construct" is meant to include any type of genetic construct containing a nucleic acid coding for a gene product in which part or all of the nucleic acid encoding sequence is capable of being transcribed. Preferably, such a sequence encodes all or part of a gene which encodes a NOEY2 polypeptide. The transcript may be translated into a protein, but it need not be. In certain embodiments, expression includes both transcription of a gene and translation of mRNA into a gene product. In other embodiments, expression only includes transcription of the nucleic acid encoding a gene of interest.

In preferred embodiments, the nucleic acid encoding a gene product is under transcriptional control of a promoter. A "promoter" refers to a DNA sequence recognized by the synthetic machinery of the cell, or introduced synthetic machinery, required to initiate the specific transcription of a gene. The phrase "under transcriptional control" means that the promoter is in the correct location and orientation in relation to the nucleic acid to control RNA polymerase initiation and expression of the gene.

The term promoter will be used here to refer to a group of transcriptional control modules that are clustered around the initiation site for RNA polymerase II. Much of the thinking about how promoters are organized derives from analyses of several viral promoters, including those for the HSV thymidine kinase (tk) and SV40 early transcription units. These studies, augmented by more recent work, have shown that promoters are composed of discrete functional modules, each consisting of approximately 7–20 bp of DNA, and containing one or more recognition sites for transcriptional activator or repressor proteins.

At least one module in each promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have recently been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter employed to control the expression of a nucleic acid sequence of interest is not believed to be important, so long as it is capable of direction the expression of the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In various embodiments, the human cytomegalovirus (CMV) immediate early gene promoter, the SV40 early promoter, the Rous sarcoma virus long terminal repeat, rat insulin promoter and glyceraldehyde-3-phosphate dehydrogenase can be used to obtain high-level expression of the coding sequence of interest. The use of other viral or mammalian cellular or bacterial phage promoters which are well-known in the art to achieve expression of a coding sequence of interest is contemplated as well, provided that the levels of expression are sufficient for a given purpose.

By employing a promoter with well-known properties, the level and pattern of expression of the protein of interest following transfection or transformation can be optimized. Further, selection of a promoter that is regulated in response to specific physiologic signals can permit inducible expression of the gene product. Tables 2 and 3 list several elements/promoters which may be employed, in the context of the present invention, to regulate the expression of the gene of interest. This list is not intended to be exhaustive of all the possible elements involved in the promotion of gene expression but, merely, to be exemplary thereof.

Enhancers are genetic elements that increase transcription from a promoter located at a distant position on the same molecule of DNA. Enhancers are organized much like promoters. That is, they are composed of many individual elements, each of which binds to one or more transcriptional proteins.

The basic distinction between enhancers and promoters is operational. An enhancer region as a whole must be able to stimulate transcription at a distance; this need not be true of a promoter region or its component elements. On the other hand, a promoter must have one or more elements that direct initiation of RNA synthesis at a particular site and in a particular orientation, whereas enhancers lack these specificities. Promoters and enhancers are often overlapping and contiguous, often seeming to have a very similar modular organization.

Where a cDNA insert is employed, one will typically desire to include a polyadenylation signal to effect proper polyadenylation of the gene transcript. The nature of the polyadenylation signal is not believed to be crucial to the successful practice of the invention, and any such sequence may be employed such as human growth hormone and SV40 polyadenylation signals. Also contemplated as an element of the expression cassette is a terminator. These elements can serve to enhance message levels and to minimize read through from the cassette into other sequences.

4.10.2 Selectable Markers

In certain embodiments of the invention, a host cell transformed with one or more NOEY2 nucleic acid segments may be identified in vitro or in vivo by including a "marker" or "reporter" gene in the expression construct and/or vector which comprises the NOEY2 polynucleotide. Such reporter or marker would confer an identifiable change to the cell permitting easy identification of cells containing the expression construct. For example, the inclusion of a drug selection marker aids in cloning and in the selection of transformants. Genes that confer resistance to neomycin, puromycin, hygromycin, DHFR, GPT, zeocin and histidinol are often employed as selectable markers. Alternatively, enzymes such as herpes simplex virus thymidine kinase (tk) or chloramphenicol acetyltransferase (CAT) may also be employed, as well as one or more immunologic markers.

The selectable marker employed is not believed to be important, so long as it is capable of being expressed simultaneously with the nucleic acid encoding a gene product. Further examples of selectable markers are well known to one of skill in the art.

4.10.3 Multigene Constructs and IRES

In certain embodiments of the invention, the use of internal ribosome binding sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message.

Any heterologous open reading frame can be linked to IRES elements. This includes genes for secreted proteins, multi-subunit proteins, encoded by independent genes, intracellular or membrane-bound proteins and selectable markers. In this way, expression of several proteins can be simultaneously engineered into a cell with a single construct and a single selectable marker.

4.10.4 Delivery of Expression Vectors

There are a number of ways in which expression vectors may introduced into cells. In certain embodiments of the invention, the expression construct comprises a virus or engineered construct derived from a viral genome. The ability of certain viruses to enter cells via receptor-mediated endocytosis, to integrate into host cell genome and express viral genes stably and efficiently have made them attractive candidates for the transfer of foreign genes into mammalian cells (Ridgeway, 1988; Nicolas and Rubenstein, 1988; Baichwal and Sugden, 1986; Temin, 1986). The first viruses used as gene vectors were DNA viruses including the papovaviruses (simian virus 40, bovine papilloma virus, and polyoma) (Ridgeway, 1988; Baichwal and Sugden, 1986) and adenoviruses (Ridgeway, 1988; Baichwal and Sugden, 1986). These have a relatively low capacity for foreign DNA sequences and have a restricted host spectrum. Furthermore, their oncogenic potential and cytopathic effects in permissive cells raise safety concerns. They can accommodate only up to 8 kb of foreign genetic material but can be readily introduced in a variety of cell lines and laboratory animals (Nicolas and Rubenstein, 1988; Temin, 1986).

One of the preferred methods for in vivo delivery involves the use of an adenovirus expression vector. "Adenovirus expression vector" is meant to include those constructs containing adenovirus sequences sufficient to (a) support packaging of the construct and (b) to express an antisense polynucleotide that has been cloned therein. In this context, expression does not require that the gene product be synthesized.

The expression vector comprises a genetically engineered form of adenovirus. Knowledge of the genetic organization of adenovirus, a 36 kb, linear, double-stranded DNA virus, allows substitution of large pieces of adenoviral DNA with foreign sequences up to 7 kb (Grunhaus and Horwitz, 1992). In contrast to retrovirus, the adenoviral infection of host cells does not result in chromosomal integration because adenoviral DNA can replicate in an episomal manner without potential genotoxicity. Also, adenoviruses are structurally stable, and no genome rearrangement has been detected after extensive amplification. Adenovirus can infect virtually all epithelial cells regardless of their cell cycle stage. So far, adenoviral infection appears to be linked only to mild disease such as acute respiratory disease in humans.

Adenovirus is particularly suitable for use as a gene transfer vector because of its mid-sized genome, ease of manipulation, high titer, wide target cell range and high infectivity. Generation and propagation of adenovirus vectors, which are replication deficient, depend on a unique helper cell line, designated 293, which was transformed from human embryonic kidney cells by Ad5 DNA fragments and constitutively expresses E1 proteins (Graham et al., 1977). Since the E3 region is dispensable from the adenovirus genome (Jones and Shenk, 1978), the current adenovirus vectors, with the help of 293 cells, carry foreign DNA in either the E1, the D3 or both regions (Graham and Prevec, 1991). In nature, adenovirus can package approximately 105% of the wild-type genome (Ghosh-Choudhury et al., 1987), providing capacity for about 2 extra kb of DNA. Combined with the approximately 5.5 kb of DNA that is replaceable in the E1 and E3 regions, the maximum capacity of the current adenovirus vector is under 7.5 kb, or about 15% of the total length of the vector. More than 80% of the adenovirus viral genome remains in the vector backbone and is the source of vector-borne cytotoxicity. Also, the replication deficiency of the E1-deleted virus is incomplete. For example, leakage of viral gene expression has been observed with the currently available vectors at high multiplicities of infection (MOI) (Rich et al. 1993).

Helper cell lines may be derived from human cells such as human embryonic kidney cells, muscle cells, hematopoietic cells or other human embryonic mesenchymal or epithelial cells. Alternatively, the helper cells may be derived from the cells of other mammalian species that are permissive for human adenovirus. Such cells include, e.g., Vero cells or other monkey embryonic mesenchymal or epithelial cells. As stated above, the preferred helper cell line is 293.

Methods for culturing 293 cells and propagating adenovirus have been described. In one format, natural cell aggregates are grown by inoculating individual cells into 1 liter siliconized spinner flasks (Techne, Cambridge, UK) containing 100–200 ml of medium. Following stirring at 40 rpm, the cell viability is estimated with trypan blue. In another format, Fibra-Cel microcarriers (Bibby Sterlin, Stone, UK) (5 g/l) is employed as follows. A cell inoculum, resuspended in 5 ml of medium, is added to the carrier (50 ml) in a 250 ml Erlenmeyer flask and left stationary, with occasional agitation, for 1 to 4 h. The medium is then replaced with 50 ml of fresh medium and shaking initiated. For virus production, cells are allowed to grow to about 80% confluence, after which time the medium is replaced (to 25% of the final volume) and adenovirus added at an MOI of 0.05. Cultures are left stationary overnight, following which the volume is increased to 100% and shaking commenced for another 72 h.

Adenovirus is easy to grow and manipulate and exhibits broad host range in vitro and in vivo. This group of viruses can be obtained in high titers, e.g., $10^9$–$10^{11}$ plaque-forming units per ml, and they are highly infective. The life cycle of adenovirus does not require integration into the host cell genome. The foreign genes delivered by adenovirus vectors are episomal and, therefore, have low genotoxicity to host cells. No side effects have been reported in studies of vaccination with wild-type adenovirus (Couch et al., 1963; Top et al., 1971), demonstrating their safety and therapeutic potential as in vivo gene transfer vectors.

Adenovirus vectors have been used in eukaryotic gene expression (Levrero et al., 1991; Gomez-Foix et al., 1992) and vaccine development (Grunhaus and Horwitz, 1992; Graham and Prevec, 1992). Recently, animal studies suggested that recombinant adenovirus could be used for gene therapy (Stratford-Perricaudet and Perricaudet, 1991; Stratford-Perricaudet et al., 1990; Rich et al., 1993). Studies in administering recombinant adenovirus to different tissues include trachea instillation (Rosenfeld et al., 1991; Rosenfeld et al., 1992), muscle injection (Ragot et al., 1993), peripheral intravenous injections (Herz and Gerard, 1993) and stereotactic inoculation into the brain (Le Gal La Salle et al., 1993).

The retroviruses are a group of single-stranded RNA viruses characterized by an ability to convert their RNA to double-stranded DNA in infected cells by a process of reverse-transcription (Coffin, 1990). The resulting DNA then stably integrates into cellular chromosomes as a provirus and directs synthesis of viral proteins. The integration results in the retention of the viral gene sequences in the recipient cell and its descendants. The retroviral genome contains three genes, gag, pol, and env that code for capsid proteins, polymerase enzyme, and envelope components, respectively. A sequence found upstream from the gag gene contains a signal for packaging of the genome into virions. Two long terminal repeat (LTR) sequences are present at the 5' and 3' ends of the viral genome. These contain strong promoter and enhancer sequences and are also required for integration in the host cell genome (Coffin, 1990).

In order to construct a retroviral vector, a nucleic acid encoding a gene of interest is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into this cell line (by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975). A novel approach designed to allow specific targeting of retrovirus vectors was recently developed based on the chemical modification of a retrovirus by the chemical addition of lactose residues to the viral envelope. This modification could permit the specific infection of hepatocytes via sialoglycoprotein receptors.

A different approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

There are certain limitations to the use of retrovirus vectors in all aspects of the present invention. For example, retrovirus vectors usually integrate into random sites in the cell genome. This can lead to insertional mutagenesis through the interruption of host genes or through the insertion of viral regulatory sequences that can interfere with the function of flanking genes (Varmus et al., 1981). Another concern with the use of defective retrovirus vectors is the potential appearance of wild-type replication-competent virus in the packaging cells. This can result from recombination events in which the intact- sequence from the recombinant virus inserts upstream from the gag, pol, env sequence integrated in the host cell genome. However, new packaging cell lines are now available that should greatly decrease the likelihood of recombination (Markowitz et al., 1988; Hersdorffer et al., 1990).

Other viral vectors may be employed as expression constructs in the present invention. Vectors derived from viruses such as vaccinia virus (Ridgeway, 1988; Baichwal and Sugden, 1986; Coupar et al., 1988) adeno-associated virus (AAV) (Ridgeway, 1988; Baichwal and Sugden, 1986; Hermonat and Muzycska, 1984) and herpesviruses may be employed. They offer several attractive features for various mammalian cells (Friedmann, 1989; Ridgeway, 1988; Baichwal and Sugden, 1986; Coupar et al., 1988; Horwich et al., 1990).

With the recent recognition of defective hepatitis B viruses, new insight was gained into the structure-function relationship of different viral sequences. In vitro studies showed that the virus could retain the ability for helper-dependent packaging and reverse transcription despite the deletion of up to 80% of its genome (Horwich et al., 1990). This suggested that large portions of the genome could be replaced with foreign genetic material. The hepatotropism and persistence (integration) were particularly attractive properties for liver-directed gene transfer. Chang et al., recently introduced the chloramphenicol acetyltransferase (CAT) gene into duck hepatitis B virus genome in the place of the polymerase, surface, and pre-surface coding sequences. It was co-transfected with wild-type virus into an avian hepatoma cell line. Culture media containing high titers of the recombinant virus were used to infect primary duckling hepatocytes. Stable CAT gene expression was detected for at least 24 days after transfection (Chang et al., 1991).

In order to effect expression of sense or antisense gene constructs, the expression construct must be delivered into a cell. This delivery may be accomplished in vitro, as in laboratory procedures for transforming cells lines, or in vivo or ex vivo, as in the treatment of certain disease states. One mechanism for delivery is via viral infection where the expression construct is encapsidated in an infectious viral particle.

Several non-viral methods for the transfer of expression constructs into cultured mammalian cells also are contemplated by the present invention. These include calcium phosphate precipitation (Graham and Van Der Eb, 1973; Chen and Okayama, 1987; Rippe et al., 1990) DEAE-dextran (Gopal, 1985), electroporation (Tur-Kaspa et al., 1986; Potter et al., 1984), direct microinjection (Harland and Weintraub, 1985), DNA-loaded liposomes (Nicolau and Sene, 1982; Fraley et al., 1979) and lipofectamine-DNA complexes, cell sonication (Fechheimer et al., 1987), gene bombardment using high velocity microprojectiles (Yang et al., 1990), and receptor-mediated transfection (Wu and Wu, 1987; Wu and Wu, 1988). Some of these techniques may be successfully adapted for in vivo or ex vivo use.

Once the expression construct has been delivered into the cell the nucleic acid encoding the gene of interest may be positioned and expressed at different sites. In certain embodiments, the nucleic acid encoding the gene may be stably integrated into the genome of the cell. This integration may be in the cognate location and orientation via homologous recombination (gene replacement) or it may be integrated in a random, non-specific location (gene augmentation). In yet further embodiments, the nucleic acid may be stably maintained in the cell as a separate, episomal segment of DNA. Such nucleic acid segments or "episomes" encode sequences sufficient to permit maintenance and replication independent of or in synchronization with the host cell cycle. How the expression construct is delivered to a cell and where in the cell the nucleic acid remains is dependent on the type of expression construct employed.

In yet another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro but it may be applied to in vivo use as well. Dubensky et al. (1984) successfully injected polyomavirus DNA in the form of calcium phosphate precipitates into liver and spleen of adult and newborn mice demonstrating active viral replication and acute infection. Benvenisty and Neshif (1986) also demonstrated that direct intraperitoneal injection of calcium phosphate-precipitated plasmids results in expression of the transfected genes. It is envisioned that DNA encoding a gene of interest may also be transferred in a similar manner in vivo and express the gene product.

In still another embodiment of the invention for transferring a naked DNA expression construct into cells may involve particle bombardment. This method depends on the ability to accelerate DNA-coated microprojectiles to a high velocity allowing them to pierce cell membranes and enter cells without killing them (Klein et al., 1987). Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold beads.

Selected organs including the liver, skin, and muscle tissue of rats and mice have been bombarded in vivo (Yang et al., 1990; Zelenin et al., 1991). This may require surgical exposure of the tissue or cells, to eliminate any intervening tissue between the gun and the target organ, i.e., ex vivo treatment. Again, DNA encoding a particular gene may be delivered via this method and still be incorporated by the present invention.

In one embodiment, such expression constructs may be entrapped in a liposome, lipid complex, nanocapsule, or other formulation using one or more of the methods disclosed in Section 4.8. Also contemplated are lipofectamine-DNA complexes. For example, liposome-mediated nucleic acid delivery and expression of foreign DNA in vitro has been very successful. Wong et al. (1980) demonstrated the feasibility of liposome-mediated delivery and expression of foreign DNA in cultured chick embryo, HeLa and hepatoma cells. Nicolau et al. (1987) accomplished successful liposome-mediated gene transfer in rats after intravenous injection.

In certain embodiments of the invention, the liposome may be complexed with a hemagglutinating virus (HVJ). This has been shown to facilitate fusion with the cell membrane and promote cell entry of liposome-encapsulated DNA (Kaneda et al., 1989). In other embodiments, the liposome may be complexed or employed in conjunction with nuclear non-histone chromosomal proteins (HMG-1) (Kato et al., 1991). In yet further embodiments, the liposome may be complexed or employed in conjunction with both HVJ and HMG-1. In that such expression constructs have been successfully employed in transfer and expression of nucleic acid in vitro and in vivo, then they are applicable for the present invention. Where a bacterial promoter is employed in the DNA construct, it also will be desirable to include within the liposome an appropriate bacterial polymerase.

Other expression constructs which can be employed to deliver a nucleic acid encoding a particular gene into cells are receptor-mediated delivery vehicles. These take advantage of the selective uptake of macromolecules by receptor-mediated endocytosis in almost all eukaryotic cells. Because of the cell type-specific distribution of various receptors, the delivery can be highly specific (Wu and Wu, 1993).

Receptor-mediated gene targeting vehicles generally consist of two components: a cell receptor-specific ligand and a DNA-binding agent. Several ligands have been used for receptor-mediated gene transfer. The most extensively characterized ligands are asialoorosomucoid (ASOR) (Wu and Wu, 1987) and transferrin (Wagner et al., 1990). Recently, a synthetic neoglycoprotein, which recognizes the same receptor as ASOR, has been used as a gene delivery vehicle (Ferkol et al., 1993; Perales et al., 1994) and epidermal growth factor (EGF) has also been used to deliver genes to squamous carcinoma cells (Eur. Pat. Appl. Publ. No. EP 0360257, specifically incorporated herein by reference).

In other embodiments, the delivery vehicle may comprise a ligand and a liposome. For example, Nicolau et al., (1987) employed lactosyl-ceramide, a galactose-terminal asialganglioside, incorporated into liposomes and observed an increase in the uptake of the insulin gene by hepatocytes. Thus, it is feasible that a nucleic acid encoding a particular gene also may be specifically delivered into a cell type such as lung, epithelial or tumor cells, by any number of receptor-ligand systems with or without liposomes. For example, epidermal growth factor (EGF) may be used as the receptor for mediated delivery of a nucleic acid encoding a gene in many tumor cells that exhibit upregulation of EGF receptor. Mannose can be used to target the mannose receptor on liver cells. Also, antibodies to CD5 (CLL), CD22 (lymphoma), CD25 (T-cell leukemia) and MAA (melanoma) can similarly be used as targeting moieties.

In certain embodiments, gene transfer may more easily be performed under ex vivo conditions. Ex vivo gene therapy refers to the isolation of cells from an animal, the delivery of a nucleic acid into the cells in vitro, and then the return of the modified cells back into an animal. This may involve the surgical removal of tissue/organs from an animal or the primary culture of cells and tissues.

Primary mammalian cell cultures may be prepared in various ways. In order for the cells to be kept viable while in vitro and in contact with the expression construct, it is necessary to ensure that the cells maintain contact with the correct ratio of oxygen and carbon dioxide and nutrients but are protected from microbial contamination. Cell culture techniques are well documented and are disclosed herein by reference (Freshner, 1992).

One embodiment of the foregoing involves the use of gene transfer to immortalize cells for the production of proteins. The gene for the protein of interest may be transferred as described above into appropriate host cells followed by culture of cells under the appropriate conditions. The gene for virtually any polypeptide may be employed in this manner. The generation of recombinant expression vectors, and the elements included therein, are discussed above. Alternatively, the protein to be produced may be an endogenous protein normally synthesized by the cell in question.

Examples of useful mammalian host cell lines are Vero and HeLa cells and cell lines of Chinese hamster ovary, W138, BHK, COS-7, 293, HepG2, NIH3T3, RIN and MDCK cells. In addition, a host cell strain may be chosen that modulates the expression of the inserted sequences, or modifies and process the gene product in the manner desired. Such modifications (e.g., glycosylation) and processing (e.g., cleavage) of protein products may be important for the function of the protein. Different host cells have characteristic and specific mechanisms for the post-translational processing and modification of proteins. Appropriate cell lines or host systems can be chosen to insure the correct modification and processing of the foreign protein expressed.

A number of selection systems may be used including, but not limited to, HSV thymidine kinase, hypoxanthine-guanine phosphoribosyltransferase and adenine phosphoribosyltransferase genes, in tk-, hgprt- or aprt- cells, respectively. Also, anti-metabolite resistance can be used as the basis of selection for dhfr, that confers resistance to; gpt, that confers resistance to mycophenolic acid; neo, that confers resistance to the aminoglycoside G418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e. a monolayer type of cell growth).

Non-anchorage dependent or suspension cultures from continuous established cell lines are the most widely used means of large scale production of cells and cell products.

However, suspension cultured cells have limitations, such as tumorigenic potential and lower protein production than adherent T-cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcomer section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

4.11 Liposomes and Nanocapsules

In certain embodiments, the inventors contemplate the use of liposomes and/or nanocapsules for the introduction of a NOEY2 composition into a host cell. Such formulations may be preferred for the introduction of pharmaceutically-acceptable formulations of the polypeptides, pharmaceuticals, and/or antibodies disclosed herein. The formation and use of liposomes is generally known to those of skill in the art (see for example, Couvreur et al., 1977 which describes the use of liposomes and nanocapsules in the targeted antibiotic therapy of intracellular bacterial infections and diseases). More recently, liposomes were developed with improved serum stability and circulation half-times (Gabizon and Papahadjopoulos, 1988; Allen and Choun, 1987).

In one instance, the disclosed composition may be entrapped in a liposome. Liposomes are vesicular structures characterized by a phospholipid bilayer membrane and an inner aqueous medium. Multilamellar liposomes have multiple lipid layers separated by aqueous medium. The term "liposome" is intended to mean a composition arising spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991).

Nanocapsules can generally entrap compounds in a stable and reproducible way (Henry-Michelland et al., 1987). To avoid side effects due to intracellular polymeric overloading, such ultrafine particles (sized around 0.1 µm) should be designed using polymers able to be degraded in vivo. Biodegradable polyalkyl-cyano-acrylate nanoparticles that meet these requirements are contemplated for use in the present invention, and such particles may be are easily made, as described (Couvreur et al., 1977; 1988). Methods of preparing polyalkyl-cyano-acrylate nanoparticles containing biologically active substances and their use are described in U.S. Pat. No. 4,329,332, U.S. Pat. No. 4,489,055, and U.S. Pat. No. 4,913,908.

Pharmaceutical compositions containing nanocapsules for the oral delivery of active agents are described in U.S. Pat. No. 5,500,224 and U.S. Pat. No. 5,620,708. U.S. Pat. No. 5,500,224 describes a pharmaceutical composition in the form of a colloidal suspension of nanocapsules comprising an oily phase consisting essentially of an oil containing dissolved therein a surfactant and suspended therein a plurality of nanocapsules having a diameter of less than 500 nanometers. U.S. Pat. No. 5,620,708 describes compositions and methods for the oral administration of drugs and other active agents. The compositions comprise an active agent carrier particle attached to a binding moiety which binds specifically to a target molecule present on the surface of a mammalian enterocyte. The binding moiety binds to the target molecule with a binding affinity or avidity sufficient to initiate endocytosis or phagocytosis of the particulate active agent carrier so that the carrier will be absorbed by the enterocyte. The active agent will then be released from the carrier to the host's systemic circulation. In this way, degradation of degradation-sensitive drugs, such as polypeptides, in the intestines can be avoided while absorption of proteins and polypeptides form the intestinal tract is increased.

U.S. Pat. No. 5,641,515 and U.S. Pat. No. 5,698,515 describe the use of nanocapsules for the oral administration of a polypeptide, specifically, insulin and are incorporated herein by reference. U.S. Pat. No. 5,698,515 described insulin containing nanocapsules intended for oral administration of insulin which comprises a hydrophilic polymer modified with an inhibitor of proteolytic enzyme, insulin and water, wherein the inhibitor of proteolytic enzymes is ovomucoid isolated from duck or turkey egg whites. U.S. Pat. No. 5,556,617 describes the use of nanoparticles as pharmaceutical treatment of the upper epidermal layers by topical application on the skin.

Poly(alkyl cyanoacrylate) nanocapsules have been used as biodegradable polymeric drug carriers for subcutaneous and peroral delivery of octreotide, a long-acting somatostatin analogue. The nanocapsules, prepared by interfacial emulsion polymerization of isobutyl cyanoacrylate, were 216 nm in diameter and incorporated 60% of octreotide. Nanocapsules were administered subcutaneously and the octreotide-loaded nanocapsules (20 mg/kg) suppressed the insulinaemia peak induced by intravenous glucose overload and depressed insulin secretion over 48 h. When administered perorally to oestrogen-treated rats, octreotide loaded nanocapsules (200 and 100 mg/kg) significantly improved the reduction of prolactin secretion and slightly increased plasma octreotide levels (Damge et al., 1997).

The negative surface charge of nanocapsules makes them particularly susceptible to lysozyme (LZM), a positively-charged enzyme that is highly concentrated in mucosas. This interaction causes destabilization of the nanocapsule by LZM; however, it was observed that the destabilizing effects caused by the adsorption of LZM onto the nanocapsules can be prevented by previous adsorption of the cationic poly (amino acid) poly-L-lysine (Calvo et al., 1997).

Calvo et al., 1996 describe the use of poly-epsilon-caprolactone (PECL) microparticles for the ocular bioavailability of drugs. Their study showed that PECL nanoparticles and nanocapsules as well as submicron emulsions are shown to be novel corneal drug carriers, and represent a useful approach for increasing the ocular bioavailability of drugs.

An excellent review of nanoparticles and nanocapsular carriers is provided by Arshady 1996. Arshady notes that one of the major obstacles to the targeted delivery of colloidal carriers, or nanocapsules, is the body's own defense mechanism in capturing foreign particles by the reticuloendothelial system (RES). This means that following intravenous administration, practically all nanometer size particles are captured by the RES (mainly the liver). The review describes recent initiatives on the design of macromolecular homing devices which seem to disguise nanoparticles from the RES and, hence, are of potential interest to the targeted delivery of nanocapsular carriers. The idea is based on a graft copolymer model embodying a link site for attachment to the carrier, a floating pad for maintaining the particles afloat in the blood stream, an affinity ligand for site-specific delivery and a structural tune for balancing the overall structure of the homing device.

Yu and Chang, 1996 describe the use of nanocapsules containing hemoglobin as potential blood substitutes. They use different polymers including polylactic acid and polyisobutyl-cyanoacrylate and modify the surface of the nanocapsules with polyethylene glycol (PEG) or with PEG 2000 PE. The surface modified nanocapsules containing hemoglobin survive longer in the circulation.

U.S. Pat. No. 5,451,410 describes the use of modified amino acid for the encapsulation of active agents. Modified amino acids and methods for the preparation and used as oral delivery systems for pharmaceutical agents are described. The modified amino acids are preparable by reacting single amino acids or mixtures of two or more kinds of amino acids with an amino modifying agent such as benzene sulfonyl chloride, benzoyl chloride, and hippuryl chloride. The modified amino acids form encapsulating microspheres in the presence of the active agent under sphere-forming conditions. Alternatively, the modified amino acids may be used as a carrier by simply mixing the amino acids with the active agent. The modified amino acids are particularly useful in delivering peptides, e.g., insulin or calmodulin, or other agents which are sensitive to the denaturing conditions of the gastrointestinal tract.

4.12 Diagnosing Cancers Involving NOEY2

The present inventors have determined that alterations in NOEY2 are associated with malignancy. Therefore, a NOEY2 polypeptide or a NOEY2 gene may be employed as a diagnostic or prognostic indicator of cancer. More specifically, point mutations, deletions, insertions or regulatory perturbations relating to NOEY2 may cause cancer or promote cancer development, cause or promoter tumor progression at a primary site, and/or cause or promote metastasis. Other phenomena associated with malignancy that may be affected by NOEY2 expression include angiogenesis and tissue invasion.

One embodiment of the instant invention comprises a method for detecting variation in the expression of NOEY2. This may comprises determining that level of NOEY2 or determining specific alterations in the expressed product. Obviously, this sort of assay has importance in the diagnosis of related cancers. Such cancer may involve cancers of the breast or ovaries, or alternatively, cancers involving the lung, liver, spleen, brain kidney, pancreas, small intestine, blood cells, lymph node, colon, endometrium, stomach, prostate, testicle, skin, head and neck, esophagus, bone marrow, blood or other tissue. In particular, the present invention relates to the diagnosis of breast and ovarian cancers.

The biological sample can be any tissue or fluid. Various embodiments include cells of the skin, muscle, facia, brain, prostate, breast, endometrium, lung, head & neck, pancreas, small intestine, blood cells, liver, testes, ovaries, colon, skin, stomach, esophagus, spleen, lymph node, bone marrow or kidney. Other embodiments include fluid samples such as peripheral blood, lymph fluid, ascites, serous fluid, pleural effusion, sputum, cerebrospinal fluid, lacrimal fluid, stool or urine.

Nucleic acid used is isolated from cells contained in the biological sample, according to standard methodologies (Sambrook et al., 1989). The nucleic acid may be genomic DNA or fractionated or whole cell RNA. Where RNA is used, it may be desired to convert the RNA to a complementary DNA. In one embodiment, the RNA is whole cell RNA; in another, it is poly-A RNA. Normally, the nucleic acid is amplified.

Depending on the format, the specific nucleic acid of interest is identified in the sample directly using amplification or with a second, known nucleic acid following amplification. Next, the identified product is detected. In certain applications, the detection may be performed by visual means (e.g., ethidium bromide staining of a gel). Alternatively, the detection may involve indirect identification of the product via chemiluminescence, radioactive scintigraphy of radiolabel or fluorescent label or even via a system using electrical or thermal impulse signals (Affymax Technology; Bellus, 1994).

Following detection, one may compare the results seen in a given patient with a statistically significant reference group of normal patients and patients that have NOEY2-related pathologies. In this way, it is possible to correlate the amount or kind of NOEY2 detected with various clinical states.

Various types of defects are to be identified. Thus, "alterations" should be read as including deletions, insertions, point mutations and duplications. Point mutations result in stop codons, frameshift mutations or amino acid substitutions. Somatic mutations are those occurring in non-germline tissues. Germ-line tissue can occur in any tissue and are inherited. Mutations in and outside the coding region also may affect the amount of NOEY2 produced, both by altering the transcription of the gene or in destabilizing or otherwise altering the processing of either the transcript (mRNA) or protein.

A variety of different assays are contemplated in this regard, including but not limited to, fluorescent in situ hybridization (FISH), direct DNA sequencing, PFGE analysis, Southern or Northern blotting, single-stranded conformation analysis (SSCA), RNAse protection assay, allele-specific oligonucleotide (ASO), dot blot analysis, denaturing gradient gel electrophoresis, RFLP and PCR-SSCP.

4.12.1 Primers and Probes

The term primer, as defined herein, is meant to encompass any nucleic acid that is capable of priming the synthesis of a nascent nucleic acid in a template-dependent process. Typically, primers are oligonucleotides from about ten to about fifteen base pairs in length or even longer sequences such as those from about twenty to about 30 base pairs or more in length, with even longer sequences be employed for certain applications. Primers may be provided in double-stranded or single-stranded form, although the single-stranded form is preferred. Probes are defined differently, although they may act as primers. Probes, while perhaps capable of priming, are designed to binding to the target DNA or RNA and need not be used in an amplification process.

In preferred embodiments, the probes or primers are labeled with radioactive species ($^{32}P$, $^{14}C$, $^{35}S$, $^{3}H$, or other label), with a fluorophore (rhodamine, fluorescein) or a chemiluminescent (luciferase).

4.12.2 Template Dependent Amplification Methods

A number of template dependent processes are available to amplify the marker sequences present in a given template sample. One of the best known amplification methods is the polymerase chain reaction (referred to as PCR™) which is described in detail in U.S. Pat. Nos. 4,683,195, 4,683,202 and 4,800,159, and in Innis et al., 1988, each of which is incorporated herein by reference in its entirety.

Briefly, in PCR™, two primer sequences are prepared that are complementary to regions on opposite complementary strands of the marker sequence. An excess of deoxynucleoside triphosphates are added to a reaction mixture along with a DNA polymerase, e.g., Taq polymerase. If the marker sequence is present in a sample, the primers will bind to the marker and the polymerase will cause the primers to be extended along the marker sequence by adding on nucleotides. By raising and lowering the temperature of the reaction mixture, the extended primers will dissociate from the marker to form reaction products, excess primers will bind to the marker and to the reaction products and the process is repeated.

A reverse transcriptase PCR™ amplification procedure (RT-PCR™) may be performed in order to quantify the amount of mRNA amplified. Methods of reverse transcribing RNA into cDNA are well known and described in Sambrook et al., 1989. Alternative methods for reverse transcription utilize thermostable, RNA-dependent DNA polymerases. These methods are described in WO 90/07641 filed Dec. 21, 1990. Polymerase chain reaction methodologies are well known in the art.

Another method for amplification is the ligase chain reaction ("LCR"), disclosed in EPO No. 320 308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750 describes a method similar to LCR for binding probe pairs to a target sequence.

Qbeta Replicase, described in PCT Application No. PCT/US87/00880, may also be used as still another amplification method in the present invention. In this method, a replicative sequence of RNA that has a region complementary to that of a target is added to a sample in the presence of an RNA polymerase. The polymerase will copy the replicative sequence that can then be detected.

An isothermal amplification method, in which restriction endonucleases and ligases are used to achieve the amplification of target molecules that contain nucleotide 5'-[α-thio]-triphosphates in one strand of a restriction site may also be useful in the amplification of nucleic acids in the present invention, Walker et al., (1992).

Strand Displacement Amplification (SDA) is another method of carrying out isothermal amplification of nucleic acids which involves multiple rounds of strand displacement and synthesis, i.e., nick translation. A similar method, called Repair Chain Reaction (RCR), involves annealing several probes throughout a region targeted for amplification, followed by a repair reaction in which only two of the four bases are present. The other two bases can be added as biotinylated derivatives for easy detection. A similar approach is used in SDA. Target specific sequences can also be detected using a cyclic probe reaction (CPR). In CPR, a probe having 3' and 5' sequences of non-specific DNA and a middle sequence of specific RNA is hybridized to DNA that is present in a sample. Upon hybridization, the reaction is treated with RNase H, and the products of the probe identified as distinctive products that are released after digestion. The original template is annealed to another cycling probe and the reaction is repeated.

Still another amplification methods described in GB Application No. 2,202,328, and in PCT Application No. PCT/US89/01025, each of which is incorporated herein by reference in its entirety, may be used in accordance with the present invention. In the former application, "modified" primers are used in a PCR-like, template- and enzyme-dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS), including nucleic acid sequence based amplification (NASBA) and 3SR (Kwoh et al., 1989; Int. Pat. Appl. Publ. No. WO 88/10315, incorporated herein by reference in their entirety). In NASBA, the nucleic acids can be prepared for amplification by standard phenol/chloroform extraction, heat denaturation of a clinical sample, treatment with lysis buffer and minispin columns for isolation of DNA and RNA or guanidinium chloride extraction of RNA. These amplification techniques involve annealing a primer which has target specific sequences. Following polymerization, DNA/RNA hybrids are digested with RNase H while double stranded DNA molecules are heat denatured again. In either case the single stranded DNA is made fully double stranded by addition of second target specific primer, followed by polymerization. The double-stranded DNA molecules are then multiply transcribed by an RNA polymerase such as T7 or SP6. In an isothermal cyclic reaction, the RNA's are reverse transcribed into single stranded DNA, which is then converted to double stranded DNA, and then transcribed once again with an RNA polymerase such as T7 or SP6. The resulting products, whether truncated or complete, indicate target specific sequences.

Eur. Pat. Appl. Publ. No. EP 329,822 (incorporated herein by reference in its entirety) disclose a nucleic acid amplification process involving cyclically synthesizing single-stranded RNA ("ssRNA"), ssDNA, and double-stranded DNA (dsDNA), which may be used in accordance with the present invention. The ssRNA is a template for a first primer oligonucleotide, which is elongated by reverse transcriptase (RNA-dependent DNA polymerase). The RNA is then removed from the resulting DNA:RNA duplex by the action of ribonuclease H(RNase H, an RNase specific for RNA in duplex with either DNA or RNA). The resultant ssDNA is a template for a second primer, which also includes the sequences of an RNA polymerase promoter (exemplified by T7 RNA polymerase) 5' to its homology to the template. This primer is then extended by DNA polymerase (exemplified by the large "Klenow" fragment of E. coli DNA polymerase I), resulting in a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

Miller et al., PCT Application WO 89/06700 (incorporated herein by reference in its entirety) disclose a nucleic acid sequence amplification scheme based on the hybridization of a promoter/primer sequence to a target single-stranded DNA ("ssDNA") followed by transcription of many RNA copies of the sequence. This scheme is not cyclic, i.e., new templates are not produced from the resultant RNA transcripts. Other amplification methods include "RACE" and "one-sided PCR™" (Frohman, 1990; Ohara et al., 1989; each herein incorporated by reference in their entirety).

Methods based on ligation of two (or more) oligonucleotides in the presence of nucleic acid having the sequence of the resulting "di-oligonucleotide", thereby amplifying the di-oligonucleotide, may also be used in the amplification step of the present invention. Wu and Wang, (1989), incorporated herein by reference in its entirety.

4.12.3 Southern/Northern Blotting

Blotting techniques are well known to those of skill in the art. Southern blotting involves the use of DNA as a target, whereas Northern blotting involves the use of RNA as a target. Each provide different types of information, although cDNA blotting is analogous, in many aspects, to blotting or RNA species.

Briefly, a probe is used to target a DNA or RNA species that has been immobilized on a suitable matrix, often a filter of nitrocellulose. The different species should be spatially separated to facilitate analysis. This often is accomplished by gel electrophoresis of nucleic acid species followed by "blotting" on to the filter.

Subsequently, the blotted target is incubated with a probe (usually labeled) under conditions that promote denaturation and rehybridization. Because the probe is designed to base pair with the target, the probe will binding a portion of the target sequence under renaturing conditions. Unbound probe is then removed, and detection is accomplished as described above.

4.12.4 Separation Methods

It normally is desirable, at one stage or another, to separate the amplification product from the template and the excess primer for the purpose of determining whether specific amplification has occurred. In one embodiment, amplification products are separated by agarose, agarose-acrylamide or polyacrylamide gel electrophoresis using standard methods. See Sambrook et al., 1989. Alternatively, chromatographic techniques may be employed to effect separation. There are many kinds of chromatography which may be used in the present invention: adsorption, partition, ion-exchange and molecular sieve, and many specialized techniques for using them including column, paper, thin-layer and gas chromatography (Freifelder et al., 1968a, Freifelder et al., 1968b; Freifelder, 1982).

4.12.5 Detection Methods

Products may be visualized in order to confirm amplification of the marker sequences. One typical visualization method involves staining of a gel with ethidium bromide and visualization under UV light. Alternatively, if the amplification products are integrally labeled with radio- or fluorometrically-labeled nucleotides, the amplification products can then be exposed to x-ray film or visualized under the appropriate stimulating spectra, following separation.

In one embodiment, visualization is achieved indirectly. Following separation of amplification products, a labeled nucleic acid probe is brought into contact with the amplified marker sequence. The probe preferably is conjugated to a chromophore but may be radiolabeled. In another embodiment, the probe is conjugated to a binding partner, such as an antibody or biotin, and the other member of the binding pair carries a detectable moiety.

In one embodiment, detection is by a labeled probe. The techniques involved are well known to those of skill in the art and can be found in many standard books on molecular protocols (see Sambrook et al., 1989). For example, chromophore or radiolabel probes or primers identify the target during or following amplification. One example of the foregoing is described in U.S. Pat. No. 5,279,721, incorporated by reference herein, which discloses an apparatus and method for the automated electrophoresis and transfer of nucleic acids. The apparatus permits electrophoresis and blotting without external manipulation of the gel and is ideally suited to carrying out methods according to the present invention.

In addition, the amplification products described above may be subjected to sequence analysis to identify specific kinds of variations using standard sequence analysis techniques. Within certain methods, exhaustive analysis of genes is carried out by sequence analysis using primer sets designed for optimal sequencing (Pignon et al, 1994). The present invention provides methods by which any or all of these types of analyses may be used. Using the sequences disclosed herein, oligonucleotide primers may be designed to permit the amplification of sequences throughout the NOEY2 gene that may then be analyzed by direct sequencing.

4.12.6 Kit Components

All the essential materials and reagents required for detecting and sequencing NOEY2 and variants thereof may be assembled together in a kit. This generally will comprise preselected primers and probes. Also included may be enzymes suitable for amplifying nucleic acids including various polymerases (RT, Taq, Sequenase™, etc.), deoxynucleotides and buffers to provide the necessary reaction mixture for amplification. Such kits also generally will comprise, in suitable means, distinct containers for each individual reagent and enzyme as well as for each primer or probe.

4.12.7 Relative Quantitative RT-PCR™

Reverse transcription (RT) of RNA to cDNA followed by relative quantitative PCR™ (RT-PCR™) can be used to determine the relative concentrations of specific mRNA species isolated from patients. By determining that the concentration of a specific mRNA species varies, it is shown that the gene encoding the specific mRNA species is differentially expressed.

In PCR™, the number of molecules of the amplified target DNA increase by a factor approaching two with every cycle of the reaction until some reagent becomes limiting. Thereafter, the rate of amplification becomes increasingly diminished until there is no increase in the amplified target between cycles. If a graph is plotted in which the cycle number is on the X axis and the log of the concentration of the amplified target DNA is on the Y axis, a curved line of characteristic shape is formed by connecting the plotted points. Beginning with the first cycle, the slope of the line is positive and constant. This is said to be the linear portion of the curve. After a reagent becomes limiting, the slope of the line begins to decrease and eventually becomes zero. At this point the concentration of the amplified target DNA becomes asymptotic to some fixed value. This is said to be the plateau portion of the curve.

The concentration of the target DNA in the linear portion of the PCR™ amplification is directly proportional to the starting concentration of the target before the reaction began. By determining the concentration of the amplified products of the target DNA in PCR™ reactions that have completed the same number of cycles and are in their linear ranges, it is possible to determine the relative concentrations of the specific target sequence in the original DNA mixture. If the DNA mixtures are cDNAs synthesized from RNAs isolated from different tissues or cells, the relative abundance of the specific mRNA from which the target sequence was derived can be determined for the respective tissues or cells. This direct proportionality between the concentration of the PCR™ products and the relative mRNA abundance is only true in the linear range of the PCR™ reaction.

The final concentration of the target DNA in the plateau portion of the curve is determined by the availability of reagents in the reaction mix and is independent of the original concentration of target DNA. Therefore, the first condition that must be met before the relative abundance of a mRNA species can be determined by RT-PCR™ for a collection of RNA populations is that the concentrations of the amplified PCR™ products must be sampled when the PCR™ reactions are in the linear portion of their curves.

The second condition that must be met for an RT-PCR™ experiment to successfully determine the relative abundance of a particular mRNA species is that relative concentrations of the amplifiable cDNAs must be normalized to some independent standard. The goal of an RT-PCR™ experiment is to determine the abundance of a particular mRNA species relative to the average abundance of all mRNA species in the sample. In the studies described below, mRNAs for β-actin, asparagine synthetase and lipocortin II were used as external and internal standards to which the relative abundance of other mRNAs are compared.

Most protocols for competitive PCR™ utilize internal PCR™ standards that are approximately as abundant as the target. These strategies are effective if the products of the PCR™ amplifications are sampled during their linear phases. If the products are sampled when the reactions are approaching the plateau phase, then the less abundant product becomes relatively over represented. Comparisons of relative abundance made for many different RNA samples, such as is the case when examining RNA samples for differential expression, become distorted in such a way as to make differences in relative abundance of RNAs appear less than they actually are. This is not a significant problem if the internal standard is much more abundant than the target. If the internal standard is more abundant than the target, then direct linear comparisons can be made between RNA samples.

The above discussion describes theoretical considerations for an RT-PCR™ assay for clinically derived materials. The problems inherent in clinical samples are that they are of variable quantity (making normalization problematic), and that they are of variable quality (necessitating the co-amplification of a reliable internal control, preferably of larger size than the target). Both of these problems are overcome if the RT-PCR™ is performed as a relative quantitative RT-PCR™ with an internal standard in which the internal standard is an amplifiable cDNA fragment that is larger than the target cDNA fragment and in which the abundance of the mRNA encoding the internal standard is roughly 5–100 fold higher than the mRNA encoding the target. This assay measures relative abundance, not absolute abundance of the respective mRNA species.

Other studies may be performed using a more conventional relative quantitative RT-PCR™ assay with an external standard protocol. These assays sample the PCR™ products in the linear portion of their amplification curves. The number of PCR™ cycles that are optimal for sampling must be empirically determined for each target cDNA fragment. In addition, the reverse transcriptase products of each RNA population isolated from the various tissue samples must be carefully normalized for equal concentrations of amplifiable cDNAs. This consideration is very important since the assay measures absolute mRNA abundance. Absolute mRNA abundance can be used as a measure of differential gene expression only in normalized samples. While empirical determination of the linear range of the amplification curve and normalization of cDNA preparations are tedious and time consuming processes, the resulting RT-PCR™ assays can be superior to those derived from the relative quantitative RT-PCR™ assay with an internal standard.

One reason for this advantage is that without the internal standard/competitor, all of the reagents can be converted into a single PCR™ product in the linear range of the amplification curve, thus increasing the sensitivity of the assay. Another reason is that with only one PCR™ product, display of the product on an electrophoretic gel or another display method becomes less complex, has less background and is easier to interpret.

4.12.8 Chip Technologies

Specifically contemplated by the present inventors are chip-based DNA technologies such as those described by Hacia et al. (1996) and Shoemaker et al. (1996). Briefly, these techniques involve quantitative methods for analyzing large numbers of genes rapidly and accurately. By tagging genes with oligonucleotides or using fixed probe arrays, one can employ chip technology to segregate target molecules as high density arrays and screen these molecules on the basis of hybridization. See also Pease et al. (1994); Fodor et al. (1991).

4.13 Methods for Screening Active Compounds

The present invention also contemplates the use of NOEY2 and active fragments, and NOEY2 nucleic acids, in the screening of compounds for activity in either stimulating NOEY2 activity, overcoming the lack of NOEY2, or blocking the effect of a mutant NOEY2 molecule. These assays may make use of a variety of different formats and may depend on the kind of "activity" for which the screen is being conducted. Contemplated functional "read-outs" include binding to a compound, inhibition of binding to a substrate, ligand, receptor or other binding partner by a compound, phosphatase activity, anti-phosphatase activity, phosphorylation of NOEY2, dephosphorylation of NOEY2, inhibition or stimulation of cell-to-cell signaling, growth, metastasis, cell division, cell migration, soft agar colony formation, contact inhibition, invasiveness, angiogenesis, apoptosis, tumor progression or other malignant phenotype.

4.13.1 In Vitro Assays

In one embodiment, the invention is to be applied for the screening of compounds that bind to the NOEY2 molecule or fragment thereof. The polypeptide or fragment may be either free in solution, fixed to a support, expressed in or on the surface of a cell. Either the polypeptide or the compound may be labeled, thereby permitting determining of binding.

In another embodiment, the assay may measure the inhibition of binding of NOEY2 to a natural or artificial substrate or binding partner. Competitive binding assays can be performed in which one of the agents (NOEY2, binding partner or compound) is labeled. Usually, the polypeptide will be the labeled species. One may measure the amount of free label versus bound label to determine binding or inhibition of binding.

Another technique for high throughput screening of compounds is described in WO 84/03564. Large numbers of small peptide test compounds are synthesized on a solid substrate, such as plastic pins or some other surface. The peptide test compounds are reacted with NOEY2 and washed. Bound polypeptide is detected by various methods.

Purified NOEY2 can be coated directly onto plates for use in the aforementioned drug screening techniques. However, non-neutralizing antibodies to the polypeptide can be used to immobilize the polypeptide to a solid phase. Also, fusion proteins containing a reactive region (preferably a terminal region) may be used to link the NOEY2 active region to a solid phase.

Various cell lines containing wild-type or natural or engineered mutations in NOEY2 can be used to study various functional attributes of NOEY2 and how a candidate compound affects these attributes. Methods for engineering mutations are described elsewhere in this document, as are naturally-occurring mutations in NOEY2 that lead to, contribute to and/or otherwise cause malignancy. In such assays, the compound would be formulated appropriately, given its biochemical nature, and contacted with a target cell. Depending on the assay, culture may be required. The cell may then be examined by virtue of a number of different physiologic assays. Alternatively, molecular analysis may be performed in which the function of NOEY2, or related pathways, may be explored. This may involve assays such as those for protein expression, enzyme function, substrate utilization, phosphorylation states of various molecules including NOEY2, cAMP levels, mRNA expression (including differential display of whole cell or polyA RNA) and others.

4.13.2 In Vivo Assays

The present invention also encompasses the use of various animal models. Here, the identity seen between human and mouse NOEY2 provides an excellent opportunity to examine the function of NOEY2 in a whole animal system where it is normally expressed. By developing or isolating mutant cells lines that fail to express normal NOEY2, one can generate cancer models in mice that will be highly predictive of cancers in humans and other mammals. These models may employ the orthotopic or systemic administration of tumor cells to mimic primary and/or metastatic cancers. Alternatively, one may induce cancers in animals by providing agents known to be responsible for certain events associated with malignant transformation and/or tumor progression. Finally, transgenic animals (discussed below) that lack a wild-type NOEY2 may be utilized as models for cancer development and treatment.

Treatment of animals with test compounds will involve the administration of the compound, in an appropriate form, to the animal. Administration will be by any route the could be utilized for clinical or non-clinical purposes, including but not limited to oral, nasal, buccal, rectal, vaginal or topical. Alternatively, administration may be by intratracheal instillation, bronchial instillation, intradermal, subcutaneous, intramuscular, intraperitoneal or intravenous injection. Specifically contemplated are systemic intravenous injection, regional administration via blood or lymph supply and intratumoral injection.

Determining the effectiveness of a compound in vivo may involve a variety of different criteria. Such criteria include, but are not limited to, survival, reduction of tumor burden or mass, arrest or slowing of tumor progression, elimination of tumors, inhibition or prevention of metastasis, increased activity level, improvement in immune effector function and improved food intake.

4.13.3 Rational Drug Design

The goal of rational drug design is to produce structural analogs of biologically active polypeptides or compounds with which they interact (agonists, antagonists, inhibitors, binding partners, etc.). By creating such analogs, it is possible to fashion drugs which are more active or stable than the natural molecules, which have different susceptibility to alteration or which may affect the function of various other molecules. In one approach, one would generate a three-dimensional structure for NOEY2 or a fragment thereof. This could be accomplished by x-ray crystallography, computer modeling or by a combination of both approaches. An alternative approach, "alanine scan," involves the random replacement of residues throughout molecule with alanine, and the resulting affect on function determined.

It also is possible to isolate a NOEY2-specific antibody, selected by a functional assay, and then solve its crystal structure. In principle, this approach yields a pharmacore upon which subsequent drug design can be based. It is possible to bypass protein crystallography altogether by generating anti-idiotypic antibodies to a functional, pharmacologically active antibody. As a mirror image of a mirror image, the binding site of anti-idiotype would be expected to be an analog of the original antigen. The anti-idiotype could then be used to identify and isolate peptides from banks of chemically- or biologically-produced peptides. Selected peptides would then serve as the pharmacore. Anti-idiotypes may be generated using the methods described herein for producing antibodies, using an antibody as the antigen.

Thus, one may design drugs which have improved NOEY2 activity or which act as stimulators, inhibitors, agonists, antagonists or NOEY2 or molecules affected by NOEY2 function. By virtue of the availability of cloned 1p31 sequences described herein, sufficient amounts of NOEY2 can be produced to perform crystallographic studies. In addition, knowledge of the polypeptide sequences permits computer employed predictions of structure-function relationships.

4.14 Pharmaceutical Compositions and Formulations

Where clinical applications involving NOEY2 compositions are contemplated, it is often necessary to prepare pharmaceutical compositions (comprising e.g., expression vectors, virus stocks, polypeptides, polynucleotides, antibodies and/or drugs) in a form appropriate for the intended application. Generally, this will entail preparing compositions that are essentially free of pyrogens, as well as other impurities that could be harmful to humans or animals.

One will generally desire to employ appropriate salts and buffers to render delivery vectors stable and allow for uptake by target cells. Buffers also will be employed when recombinant cells are introduced into a human or a non-human animal. Aqueous compositions of the present invention comprise an effective amount of the vector to cells, dissolved or dispersed in a pharmaceutically acceptable carrier or aqueous medium. Such compositions also are referred to as inocula. The phrase "pharmaceutically or pharmacologically acceptable" refer to molecular entities and compositions that do not produce adverse, allergic, or other untoward reactions when administered to an animal or a human. As used herein, "pharmaceutically acceptable carrier" includes any and all solvents, dispersion media, coatings, antibacterial and antifungal agents, isotonic and absorption delaying agents and the like. The use of such media and agents for pharmaceutically active substances is well know in the art. Except insofar as any conventional media or agent is incompatible with the vectors or cells of the present invention, its use in therapeutic compositions is contemplated. Supplementary active ingredients also can be incorporated into the compositions.

The active compositions of the present invention may include classic pharmaceutical preparations. Administration of these compositions according to the present invention will be via any common route so long as the target tissue is available via that route. This includes oral, nasal, buccal, rectal, vaginal or topical. Alternatively, administration may be by orthotopic, intradermal, subcutaneous, intramuscular, intraperitoneal or intravenous injection. Such compositions would normally be administered as pharmaceutically acceptable compositions, described supra.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial an antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral administration the polypeptides of the present invention may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The compositions of the present invention may be formulated in a neutral or salt form. Pharmaceutically-acceptable salts include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like. For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.15 Transgenic Animals

In one embodiment of the invention, a transgenic animal is produced which contains one or more functional transgenes that encode a functional NOEY2 polypeptide or a variant thereof. Transgenic animals expressing NOEY2 transgenes, recombinant cell lines derived from such animals and transgenic embryos may be useful in methods for screening for and identifying agents that induce or repress function of NOEY2. Transgenic animals of the present invention may also be used as models for studying indications such as cancers.

In one embodiment of the invention, a NOEY2 transgene is introduced into a non-human host to produce a transgenic animal expressing a NOEY2 gene. The transgenic animal is produced by the integration of the transgene into the genome in a manner that permits the expression of the transgene. Methods for producing transgenic animals are generally described by Wagner and Hoppe (U.S. Pat. No. 4,873,191; which is incorporated herein by reference), Brinster et al. 1985; which is incorporated herein by reference in its entirety) and in "Manipulating the Mouse Embryo; A Laboratory Manual" 2nd edition (eds., Hogan, Beddington, Costantimi and Long, Cold Spring Harbor Laboratory Press, 1994; which is incorporated herein by reference in its entirety). Exemplary non-human animals include mice, rats, monkeys, hamsters, pigs, dogs, cats, goats, rabbits, horses, sheep, or virtually any other animal for which methods have been developed for introducing a stable transgene into its germline.

It may be desirable to replace the endogenous NOEY2 gene(s) by homologous recombination between the transgene and the endogenous gene; or the endogenous gene may be eliminated by deletion as in the preparation of "knockout" animals. Typically, a NOEY2 gene flanked by genomic sequences is transferred by microinjection into a fertilized egg. The microinjected eggs are implanted into a host female, and the progeny are screened for the expression of the transgene. Transgenic animals may be produced from the fertilized eggs from a number of animals including, but not limited to reptiles, amphibians, birds, mammals, and fish. Within a particularly preferred embodiment, transgenic mice are generated which overexpress NOEY2 or express a mutant form of the polypeptide. Alternatively, the absence of NOEY2 in "knock-out" mice permits the study of the effects that loss of NOEY2 protein has on a cell in vivo. Knock-out mice also provide a model for the development of NOEY2-related cancers, and particularly ovarian and breast cancers.

As noted above, transgenic animals and cell lines derived from such animals may find use in certain testing studies. In this regard, transgenic animals and cell lines capable of expressing wild-type or mutant NOEY2 may be exposed to test substances. These test substances can be screened for the ability to enhance wild-type NOEY2 expression and or function or impair the expression or function of mutant NOEY2.

4.16 Mutagenesis Methods

In certain aspects of the invention, it is desirable to introduce one or more mutations, insertions, or deletions into a polynucleotide encoding a NOEY2 or NOEY2-like polypeptide. The means for mutagenizing nucleic acid segments are well-known to those of skill in the art. Modifications to such promoter regions may be made by random, or site-specific mutagenesis procedures. The promoter region may be modified by altering its structure through the addition or deletion of one or more nucleotides from the sequence which encodes the corresponding un-modified promoter region.

Mutagenesis may be performed in accordance with any of the techniques known in the art such as and not limited to synthesizing an oligonucleotide having one or more mutations within the sequence of a particular promoter region. In particular, site-specific mutagenesis is a technique useful in the preparation of promoter mutants, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to about 75 nucleotides or more in length is preferred, with about 10 to about 25 or more residues on both sides of the junction of the sequence being altered.

The technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired promoter region or peptide. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform or transfect appropriate cells, such as *E. coli* cells, and clones are selected which include recombinant vectors bearing the mutated sequence arrangement. A genetic selection scheme was devised by Kunkel et al. (1987) to enrich for clones incorporating the mutagenic oligonucleotide. Alternatively, the use of PCR™ with commercially available thermostable enzymes such as Taq polymerase may be used to incorporate a mutagenic oligonucleotide primer into an amplified DNA fragment that can then be cloned into an appropriate cloning or expression vector. The PCR™-mediated mutagenesis procedures of Tomic et al. (1990) and Upender et al. (1995) provide two examples of such protocols. A PCR™ employing a thermostable ligase in addition to a thermostable polymerase may also be used to incorporate a phosphorylated mutagenic oligonucleotide into an amplified DNA fragment that may then be cloned into an appropriate cloning or expression vector. The mutagenesis procedure described by Michael (1994) provides an example of one such protocol.

The preparation of sequence variants of the selected promoter-encoding DNA segments using site-directed mutagenesis is provided as a means of producing potentially useful species and is not meant to be limiting as there are other ways in which sequence variants of DNA sequences may be obtained. For example, recombinant vectors encoding the desired promoter sequence may be treated with mutagenic agents, such as hydroxylamine, to obtain sequence variants.

As used herein, the term "oligonucleotide directed mutagenesis procedure" refers to template-dependent processes and vector-mediated propagation which result in an increase in the concentration of a specific nucleic acid molecule relative to its initial concentration, or in an increase in the concentration of a detectable signal, such as amplification. As used herein, the term "oligonucleotide directed mutagenesis procedure" also is intended to refer to a process that involves the template-dependent extension of a primer molecule. The term template-dependent process refers to nucleic acid synthesis of an RNA or a DNA molecule wherein the sequence of the newly synthesized strand of nucleic acid is dictated by the well-known rules of complementary base pairing (see, for example, Watson, 1987). Typically, vector mediated methodologies involve the introduction of the nucleic acid fragment into a DNA or RNA vector, the clonal amplification of the vector, and the recovery of the amplified nucleic acid fragment. Examples of such methodologies are provided by U.S. Pat. No. 4,237,224, specifically incorporated herein by reference in its entirety.

A number of template dependent processes are available to amplify the target sequences of interest present in a sample. One of the best known amplification methods is the polymerase chain reaction (PCR™) which is described in detail in U.S. Pat. Nos. 4,683,195, 4,683,202 and 4,800,159, each of which is incorporated herein by reference in its entirety. Briefly, in PCR™, two primer sequences are prepared which are complementary to regions on opposite complementary strands of the target sequence. An excess of deoxynucleoside triphosphates are added to a reaction mixture along with a DNA polymerase (e.g., Taq polymerase). If the target sequence is present in a sample, the primers will bind to the target and the polymerase will cause the primers to be extended along the target sequence by adding on nucleotides. By raising and lowering the temperature of the reaction mixture, the extended primers will dissociate from the target to form reaction products, excess primers will bind to the target and to the reaction products and the process is repeated. Preferably a reverse transcriptase PCR™ amplification procedure may be performed in order to quantify the amount of mRNA amplified. Polymerase chain reaction methodologies are well known in the art.

Another method for amplification is the ligase chain reaction (referred to as LCR), disclosed in Eur. Pat. Appl. Publ. No. 320,308, incorporated herein by reference in its entirety. In LCR, two complementary probe pairs are prepared, and in the presence of the target sequence, each pair will bind to opposite complementary strands of the target such that they abut. In the presence of a ligase, the two probe pairs will link to form a single unit. By temperature cycling, as in PCR™, bound ligated units dissociate from the target and then serve as "target sequences" for ligation of excess probe pairs. U.S. Pat. No. 4,883,750, incorporated herein by reference in its entirety, describes an alternative method of amplification similar to LCR for binding probe pairs to a target sequence.

Qbeta Replicase, described in PCT Intl. Pat. Appl. Publ. No. PCT/US87/00880, incorporated herein by reference in its entirety, may also be used as still another amplification method in the present invention. In this method, a replicative sequence of RNA which has a region complementary to that of a target is added to a sample in the presence of an RNA polymerase. The polymerase will copy the replicative sequence which can then be detected.

An isothermal amplification method, in which restriction endonucleases and ligases are used to achieve the amplification of target molecules that contain nucleotide 5'-[α-thio] triphosphates in one strand of a restriction site (Walker et al., 1992, incorporated herein by reference in its entirety), may also be useful in the amplification of nucleic acids in the present invention.

Strand Displacement Amplification (SDA) is another method of carrying out isothermal amplification of nucleic acids which involves multiple rounds of strand displacement and synthesis, e.g., nick translation. A similar method, called Repair Chain Reaction (RCR) is another method of amplification which may be useful in the present invention and is involves annealing several probes throughout a region targeted for amplification, followed by a repair reaction in which only two of the four bases are present. The other two bases can be added as biotinylated derivatives for easy detection. A similar approach is used in SDA.

Still other amplification methods described in Great Britain Pat. Appl. No. 2,202,328, and in PCT Intl. Pat. Appl. Publ. No. PCT/US89/01025, each of which is incorporated herein by reference in its entirety, may be used in accordance with the present invention. In the former application, "modified" primers are used in a PCR like, template and enzyme dependent synthesis. The primers may be modified by labeling with a capture moiety (e.g., biotin) and/or a detector moiety (e.g., enzyme). In the latter application, an excess of labeled probes are added to a sample. In the presence of the target sequence, the probe binds and is cleaved catalytically. After cleavage, the target sequence is released intact to be bound by excess probe. Cleavage of the labeled probe signals the presence of the target sequence.

Other nucleic acid amplification procedures include transcription-based amplification systems (TAS) (Kwoh et al., 1989; PCT Intl. Pat. Appl. Publ. No. WO 88/10315, incorporated herein by reference in its entirety), including nucleic acid sequence based amplification (NASBA) and 3SR. In NASBA, the nucleic acids can be prepared for amplification by standard phenol/chloroform extraction, heat denaturation of a sample, treatment with lysis buffer and minispin columns for isolation of DNA and RNA or guanidinium chloride extraction of RNA. These amplification techniques involve annealing a primer which has crystal protein-specific sequences. Following polymerization, DNA/RNA hybrids are digested with RNase H while double stranded DNA molecules are heat denatured again. In either case the single stranded DNA is made fully double stranded by addition of second crystal protein-specific primer, followed by polymerization. The double stranded DNA molecules are then multiply transcribed by a polymerase such as T7 or SP6. In an isothermal cyclic reaction, the RNAs are reverse transcribed into double stranded DNA, and transcribed once against with a polymerase such as T7 or SP6. The resulting products, whether truncated or complete, indicate crystal protein-specific sequences.

Eur. Pat. Appl. Publ. No. 329,822, incorporated herein by reference in its entirety, disclose a nucleic acid amplification process involving cyclically synthesizing single-stranded RNA ("ssRNA"), ssDNA, and double-stranded DNA (dsDNA), which may be used in accordance with the present invention. The ssRNA is a first template for a first primer oligonucleotide, which is elongated by reverse transcriptase (RNA-dependent DNA polymerase). The RNA is then removed from resulting DNA:RNA duplex by the action of ribonuclease H(RNase H, an RNase specific for RNA in a duplex with either DNA or RNA). The resultant ssDNA is a second template for a second primer, which also includes the sequences of an RNA polymerase promoter (exemplified by T7 RNA polymerase) 5' to its homology to its template. This primer is then extended by DNA polymerase (exemplified by the large "Klenow" fragment of *E. coli* DNA polymerase I), resulting as a double-stranded DNA ("dsDNA") molecule, having a sequence identical to that of the original RNA between the primers and having additionally, at one end, a promoter sequence. This promoter sequence can be used by the appropriate RNA polymerase to make many RNA copies of the DNA. These copies can then re-enter the cycle leading to very swift amplification. With proper choice of enzymes, this amplification can be done isothermally without addition of enzymes at each cycle. Because of the cyclical nature of this process, the starting sequence can be chosen to be in the form of either DNA or RNA.

PCT Intl. Pat. Appl. Publ. No. WO 89/06700, incorporated herein by reference in its entirety, disclose a nucleic acid sequence amplification scheme based on the hybridization of a promoter/primer sequence to a target single-stranded DNA ("ssDNA") followed by transcription of many RNA copies of the sequence. This scheme is not cyclic; i.e. new templates are not produced from the resultant RNA transcripts. Other amplification methods include "RACE" (Frohman, 1990), and "one-sided PCR" (Ohara, 1989) which are well-known to those of skill in the art.

Methods based on ligation of two (or more) oligonucleotides in the presence of nucleic acid having the sequence of the resulting "di-oligonucleotide", thereby amplifying the di-oligonucleotide (Wu and Dean, 1996, incorporated herein by reference in its entirety), may also be used in the amplification of DNA sequences of the present invention.

4.17 Biological Functional Equivalents

In certain embodiments of the invention, one may desire to mutagenize a NOEY2 polypeptide or polynucleotide to make a modification and/or change in the structure of the NOEY2 proteins or DNA segments which encode them and still obtain a functional molecule that encodes a protein or peptide with desirable characteristics. The following is a discussion based upon changing the amino acids of a protein to create an equivalent, or even an improved, second-generation molecule. The amino acid changes may be achieved by changing the codons of the DNA sequence, according to the codons given in Table 1.

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

TABLE 1

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic Acid | Asp | D | GAC | GAU | | |
| Glutamic Acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |
| Leucine | Leu | L | UUA | UUG | CUA | CUC | CUG | CUU |
| Methionine | Met | M | AUG | | | |
| Asparagine | Asn | N | AAC | AAU | | |
| Proline | Pro | P | CCA | CCC | CCG | CCU |
| Glutamine | Gln | Q | CAA | CAG | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU |
| Valine | Val | V | GUA | GUC | GUG | GUU |
| Tryptophan | Trp | W | UGG | | | |
| Tyrosine | Tyr | Y | UAC | UAU | | |

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.18 Methods for Treating NOEY2 Related Malignancies

The present invention also involves, in another embodiment, the treatment of cancer. The types of cancer that may be treated, according to the present invention, is limited only by the involvement of NOEY2. By involvement, it is not even a requirement that NOEY2 be mutated or abnormal—the overexpression of this tumor suppressor may actually overcome other lesions within the cell. Thus, it is contemplated that a wide variety of tumors may be treated using NOEY2 therapy, particularly those of the breast and ovaries, but also cancers of the lung, liver, spleen, brain kidney, lymph node, pancreas, small intestine, blood cells, colon, stomach, endometrium, prostate, testicle, skin, head and neck, esophagus, bone marrow, blood or other tissue.

In many contexts, it is not necessary that the tumor cell be killed or induced to undergo normal cell death or "apoptosis." Rather, to accomplish a meaningful treatment, all that is required is that the tumor growth be slowed to some degree. It may be that the tumor growth is completely blocked, however, or that some tumor regression is achieved. Clinical terminology such as "remission" and "reduction of tumor" burden also are contemplated given their normal usage.

4.18.1 Gene Therapy

One of the therapeutic embodiments contemplated by the present inventors is the intervention, at the molecular level, in the events involved in the tumorigenesis of some cancers. Specifically, the present inventors intend to provide, to a cancer cell, an expression construct capable of providing NOEY2 to that cell. Because NOEY2 transcripts have been identified not only in humans, but also in rat, mouse, monkey, and hamster, any of these nucleic acids could be used in human or animal therapy, as could any of the gene sequence variants discussed above which would encode the same, or a biologically equivalent polypeptide. The development and use of such genes for treatment of cancers using a "gene therapy" approach are well known to those of skill in the art. Particularly preferred expression vectors are viral vectors such as adenovirus, adeno-associated virus, herpesvirus, vaccinia virus and retrovirus. Also preferred is an expression vector that is contained within, or formulating using encapsulation within a lipid vesicle, lipid particle, liposome, or liposome-derived composition.

Those of skill in the art are well aware of how to apply gene delivery to in vivo and ex vivo situations. For viral vectors, one generally will prepare a viral vector stock. Depending on the kind of virus and the titer attainable, one may deliver anywhere on the order of from about $1\times10^4$ to about $1\times10^6$ infectious particles to the patient. Alternatively, one may deliver higher concentrations of infectious particles to the patient, on the order of from about $1\times10^9$ to about $1\times10^{12}$ or higher, depending upon the particular formulation, application, or cancer to be treated. Similar figures may be extrapolated for liposomal or other non-viral formulations by comparing relative uptake efficiencies. Formulation as a pharmaceutically acceptable composition is known in the art, as discussed supra.

Various routes are contemplated for various tumor types. The section below on routes contains an extensive list of possible routes. For practically any tumor, systemic delivery is contemplated. This will prove especially important for attacking microscopic or metastatic cancer. Where discrete tumor mass may be identified, a variety of direct, local and regional approaches may be taken. For example, the tumor may be directly injected with the expression vector. A tumor bed may be treated prior to, during or after resection. Following resection, one generally will deliver the vector by a catheter left in place following surgery. One may utilize the tumor vasculature to introduce the vector into the tumor by injecting a supporting vein or artery. A more distal blood supply route also may be utilized.

In a different embodiment, ex vivo gene therapy is contemplated. This approach is particularly suited, although not limited, to treatment of bone marrow associated cancers. In an ex vivo embodiment, cells from the patient are removed and maintained outside the body for at least some period of time. During this period, a therapy is delivered, after which the cells are reintroduced into the patient; hopefully, any tumor cells in the sample have been killed.

Autologous bone marrow transplant (ABMT) is an example of ex vivo gene therapy. Basically, the notion behind ABMT is that the patient will serve as his or her own bone marrow donor. Thus, a normally lethal dose of irradiation or chemotherapeutic may be delivered to the patient to kill tumor cells, and the bone marrow repopulated with the patients own cells that have been maintained (and perhaps expanded) ex vivo. Because, bone marrow often is contaminated with tumor cells, it is desirable to purge the bone marrow of these cells. Use of gene therapy to accomplish this goal is yet another way NOEY2 may be utilized according to the present invention.

4.18.2 Immunotherapy

Immunotherapeutics, generally, rely on the use of immune effector cells and molecules to target and destroy cancer cells. The immune effector may be, for example, an antibody specific for some marker on the surface of a tumor cell. The antibody alone may serve as an effector of therapy or it may recruit other cells to actually effect cell killing. The antibody also may be conjugated to a drug or toxin (chemotherapeutic, radionuclide, ricin A chain, cholera toxin, pertussis toxin, etc.) and serve merely as a targeting agent. Alternatively, the effector may be a lymphocyte carrying a surface molecule that interacts, either directly or indirectly, with a tumor cell target. Various effector cells include cytotoxic T cells and NK cells.

According to the present invention, it is unlikely that NOEY2 could serve as a target for an immune effector given that (a) it is unlikely to be expressed on the surface of the cell and (b) that the presence, not absence, of NOEY2 is associated with the normal state. However, it is possible that particular mutant forms of NOEY2 may be targeted by immunotherapy, either using antibodies, antibody conjugates or immune effector cells.

A more likely scenario is that immunotherapy could be used as part of a combined therapy, in conjunction with NOEY2-targeted gene therapy. The general approach for combined therapy is discussed below. Generally, the tumor cell must bear some marker that is amenable to targeting, i.e., is not present on the majority of other cells. Many tumor marker exist and any of these may be suitable for targeting in the context of the present invention. Common tumor markers include carcinoembryonic antigen, prostate specific antigen, urinary tumor associated antigen, fetal antigen, tyrosinase (p97), gp68, TAG-72, HMFG, Sialyl Lewis Antigen, MucA, MucB, PLAP, estrogen receptor, laminin receptor, erb B and p155.

4.18.3 Protein Therapy

Another therapy approach is the provision, to a subject, of NOEY2 polypeptide, active fragments, synthetic peptides, mimetics or other analogs thereof. The protein may be produced by recombinant expression means or, if small enough, generated by an automated peptide synthesizer. Formulations would be selected based on the route of administration and purpose including, but not limited to, liposomal formulations and classic pharmaceutical preparations.

4.18.4 Combined Therapy with Immunotherapy, Chemotherapy or Radiotherapy

Tumor cell resistance to DNA damaging agents represents a major problem in clinical oncology. One goal of current cancer research is to find ways to improve the efficacy of chemo- and radiotherapy. One way is by combining such traditional therapies with gene therapy. For example, the herpes simplex-thymidine kinase (HS-tk) gene, when delivered to brain tumors by a retroviral vector system, successfully induced susceptibility to the antiviral agent ganciclovir (Culver et al., 1992). In the context of the present invention, it is contemplated that NOEY2 replacement therapy could be used similarly in conjunction with chemo- or radiotherapeutic intervention. It also may prove effective to combine NOEY2 gene therapy with immunotherapy, as described above.

To kill cells, inhibit cell growth, inhibit metastasis, inhibit angiogenesis or otherwise reverse or reduce the malignant phenotype of tumor cells, using the methods and compositions of the present invention, one would generally contact a "target" cell with a NOEY2 expression construct and at least one other agent. These compositions would be provided in a combined amount effective to kill or inhibit proliferation of the cell. This process may involve contacting the cells with the expression construct and the agent(s) or factor(s) at the same time. This may be achieved by contacting the cell with a single composition or pharmacological formulation that includes both agents, or by contacting the cell with two distinct compositions or formulations, at the same time, wherein one composition includes the expression construct and the other includes the agent.

Alternatively, the gene therapy treatment may precede or follow the other agent treatment by intervals ranging from min to wk. In embodiments where the other agent and expression construct are applied separately to the cell, one would generally ensure that a significant period of time did not expire between the time of each delivery, such that the agent and expression construct would still be able to exert an advantageously combined effect on the cell. In such instances, it is contemplated that one would contact the cell with both modalities within about 12–24 h of each other and, more preferably, within about 6–12 h of each other, with a delay time of only about 12 h being most preferred. In some situations, it may be desirable to extend the time period for treatment significantly, however, where several days (2, 3, 4, 5, 6 or 7) to several wk (1, 2, 3, 4, 5, 6, 7 or 8) lapse between the respective administrations.

It also is conceivable that more than one administration of either NOEY2 or the other agent will be desired. Various combinations may be employed, where NOEY2 is "A" and the other agent is "B", as exemplified below:

A/B/A B/A/B B/B/A A/A/B B/A/A A/B/B B/B/B/A B/B/A/B

A/A/B/B A/B/A/B A/B/B/A B/B/A/A B/A/B/A B/A/A/B B/B/B/A

A/A/A/B B/A/A/A A/B/A/A A/A/B/A A/B/B/B B/A/B/B B/B/A/B

Other combinations are contemplated. Again, to achieve cell killing, both agents are delivered to a cell in a combined amount effective to kill the cell.

Agents or factors suitable for use in a combined therapy are any chemical compound or treatment method that induces DNA damage when applied to a cell. Such agents and factors include radiation and waves that induce DNA damage such as, γ-irradiation, X-rays, UV-irradiation, microwaves, electronic emissions, and the like. A variety of chemical compounds, also described as "chemotherapeutic agents," function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide. In certain embodiments, the use of cisplatin in combination with a NOEY2 expression construct is particularly preferred as this compound.

In treating cancer according to the invention, one would contact the tumor cells with an agent in addition to the expression construct. This may be achieved by irradiating the localized tumor site with radiation such as X-rays, UV-light, γ-rays or even microwaves. Alternatively, the tumor cells may be contacted with the agent by administering to the subject a therapeutically effective amount of a pharmaceutical composition comprising a compound such as, adriamycin, 5-fluorouracil, etoposide, camptothecin, actinomycin-D, mitomycin C, or more preferably, cisplatin. The agent may be prepared and used as a combined therapeutic composition, or kit, by combining it with a NOEY2 expression construct, as described above.

Agents that directly cross-link nucleic acids, specifically DNA, are envisaged to facilitate DNA damage leading to a synergistic, antineoplastic combination with NOEY2. Agents such as cisplatin, and other DNA alkylating agents may be used. Cisplatin has been widely used to treat cancer, with efficacious doses used in clinical applications of 20 mg/m$^2$ for 5 days every three wk for a total of three courses. Cisplatin is not absorbed orally and must therefore be delivered via injection intravenously, subcutaneously, intratumorally or intraperitoneally.

Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like. Widely used in a clinical setting for the treatment of neoplasms, these compounds are administered through bolus injections intravenously at doses ranging from 25–75 mg/m at 21 day intervals for adriamycin, to 35–50 mg/m$^2$ for etoposide intravenously or double the intravenous dose orally.

Agents that disrupt the synthesis and fidelity of nucleic acid precursors and subunits also lead to DNA damage. As such a number of nucleic acid precursors have been developed. Particularly useful are agents that have undergone extensive testing and are readily available. As such, agents such as 5-fluorouracil (5-FU), are preferentially used by neoplastic tissue, making this agent particularly useful for targeting to neoplastic cells. Although quite toxic, 5-FU, is applicable in a wide range of carriers, including topical, however intravenous administration with doses ranging from 3 to 15 mg/kg/day being commonly used.

Other factors that cause DNA damage and have been used extensively include what are commonly known as γ-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes. Dosage ranges for X-rays range from daily doses of 50 to 200 roentgens for prolonged periods of time (3 to 4 wk), to single doses of 2000 to 6000 roentgens. Dosage ranges for radioisotopes vary widely, and depend on the half-life of the isotope, the strength and type of radiation emitted, and the uptake by the neoplastic cells.

The skilled artisan is directed to "Remington's Pharmaceutical Sciences" 15th Edition, chapter 33, in particular pages 624–652. Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

The inventors propose that the regional delivery of NOEY2 expression constructs to patients with NOEY2-linked cancers will be a very efficient method for delivering a therapeutically effective gene to counteract the clinical disease, and particularly to cancers such as ovarian and breast cancer. Similarly, the chemo- or radiotherapy may be directed to a particular, affected region of the subjects body. Alternatively, systemic delivery of expression construct and/or the agent may be appropriate in certain circumstances, for example, where extensive metastasis has occurred.

In addition to combining NOEY2-targeted therapies with chemo- and radiotherapies, it also is contemplated that combination with other gene therapies will be advantageous. For example, targeting of NOEY2 and p53 or p16 mutations at the same time may produce an improved anti-cancer treatment. Any other tumor-related gene conceivably can be targeted in this manner, for example, p21, Rb, APC, DCC, NF-1, NF-2, BCRA2, p16, FHIT, WT-1, MEN-I, MEN-II, BRCA1, VHL, FCC, MCC, ras, myc, neu, raf erb, src, fms, jun, trk, ret, gsp, hst, bcl and abl.

It also should be pointed out that any of the foregoing therapies may prove useful by themselves in treating a NOEY2-related cancer. In this regard, reference to chemotherapeutics and non-NOEY2 gene therapy in combination should also be read as a contemplation that these approaches may be employed separately.

4.19 ELISAs and Immunoprecipitation

ELISAs may be used in conjunction with the invention. In an ELISA assay, proteins or peptides incorporating tumor suppressor protein antigen sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of milk powder. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 h, at temperatures preferably on the order of about 25° to about 27° C. Following incubation, the antisera-contacted surface is washed so as to remove non-immuno-complexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease or peroxidase-conjugated anti-human IgG for a period of time and under conditions which favor the development of immunocomplex formation (e.g., incubation for 2 h at room temperature in a PBS-containing solution such as PBS Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectra spectrophotometer.

The anti-tumor suppressor protein antibodies of the present invention are particularly useful for the isolation of other tumor suppressor protein antigens by immunoprecipitation. Immunoprecipitation involves the separation of the target antigen component from a complex mixture, and is used to discriminate or isolate minute amounts of protein. For the isolation of membrane proteins cells must be solubilized into detergent micelles. Nonionic salts are preferred, since other agents such as bile salts, precipitate at acid pH or in the presence of bivalent cations.

In an alternative embodiment the antibodies of the present invention are useful for the close juxtaposition of two antigens. This is particularly useful for increasing the localized concentration of antigens, e.g. enzyme-substrate pairs.

4.20 Western Blots

The NOEY2 compositions of the present invention will find great use in immunoblot or western blot analysis. The anti-NOEY2 antibodies may be used as high-affinity primary reagents for the identification of proteins immobilized onto a solid support matrix, such as nitrocellulose, nylon or combinations thereof. In conjunction with immuno-precipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

4.21 Definitions

The following words and phrases have the meanings set forth below:

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Structural gene: A gene that is expressed to produce a polypeptide.

Transformation: A process of introducing an exogenous DNA sequence (e.g., a vector, a recombinant DNA molecule) into a cell or protoplast in which that exogenous DNA is incorporated into a chromosome or is capable of autonomous replication.

Transformed cell: A cell whose DNA has been altered by the introduction of an exogenous DNA molecule into that cell.

Transgenic cell: Any cell derived or regenerated from a transformed cell or derived from a transgenic cell.

Vector: A DNA molecule capable of replication in a host cell and/or to which another DNA segment can be operatively linked so as to bring about replication of the attached segment. A plasmid is an exemplary vector.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1

Isolation and Characterization of the NOEY2 Gene

The inventors have utilized differential display of mRNA by means of the polymerase chain reaction (DDPCR™) (Liang and Pardee, 1992) to isolate a novel gene-NOEY2 from normal ovarian epithelial cells, it may serve as a tumor suppresser gene in ovarian and breast cancer.

Since 1990, the inventors have adapted a system developed by Dr. Nellie Auersperg (Pizon et al., 1988) for maintaining normal human ovarian surface epithelial (OSE) cells in culture to facilitate comparison with malignant ovarian cancer cell lines or with tumor cells isolated directly from ascites fluid. The normal OSE cells culture are obtained by gently scraping the surface of ovaries from patients undergoing surgery for nonmalignant gynecological diseases. OSE cells can only be maintained in culture for 8 to 10 passages. The cell cycle studies showed that most of OSE cells stably arrest growth with a GI DNA content, only small part of OSE cells had the ability to enter S phase. Since epithelial cystoadenocarcinoma constitute the large majority of ovarian malignancies, OSE cells provide a good model to investigate this cancer.

Using Differential Display Polymerase Chain Reaction (DDPCR™), the inventors have isolated and cloned a novel gene—NOEY2—it is expressed in normal ovarian epithelial cells but consistently absent or down-regulated in the ovarian cancer cell lines.

Using rapid amplification of cDNA ends (RACE), the sequence of NOEY2 was amplified from OSE mRNA template between a defined internal site and unknown 5' end of the mRNA. The first strand cDNA is synthesized from ovarian epithelial cell RNA using an NOEY2-specific primer SP1, AMV reverse transcriptase and the deoxynucleotide mixture. Then terminal transferase is used to add a homopolymeric A-tail to the 3' end of the cDNA. Tailed cDNA is then amplified by PCR™ using a NOEY2 specific primer SP2 and the oligo dT-anchor primer. As a result the 5' RACE products were cloned into the TA vector for subsequent characterization, which included sequencing and restriction mapping. A cDNA library from OSE cells constructed in Lambda ZAPII® were screened with the extended NOEY2 cDNA. 5 μg of mRNA was purified from OSE cells. The ZAP-cDNA synthesis kit (Stratagene, La Jolla, Calif.) was used to construct OSE cDNA library. This cDNA library provided a method by which the transcription and processing of ovarian epithelial cell mRNA can be examined. The extended NOEY2 cDNA from RACE (Boehringer Mannheim, Indianapolis, Ind.) was $^{32}$P-dCTP labeled by a random primer and used for screening OSE cDNA library. This screening procedure is performed on bacteriophage plaques, the OSE cDNA library is spread out on agarose plates, then the clones were transferred to filter membranes. The clones were hybridized to NOEY2 DNA probe. The positive clones were subsequently analyzed, they encoded the mRNA sequence and allowed prediction of the amino acid sequence. Using these two techniques, close to a full-length NOEY2 cDNA sequence and open reading from (ORF) was obtained (FIG. 1A and FIG. 1B). The nucleotide sequence (SEQ ID NO:1) contains a 5' untranslated region of 149 bp, an open reading frame of 684 bp encoding a protein of 228 amino acids (SEQ ID NO:2) ending with a TGA codon and 646 bp of 3' untranslated sequence. Translation of the NOEY2 protein yielded a protein of approximately 26 kDa. The nucleotide and amino acid sequence of the ORF was used to search the Genbank EST database using Netscape search GenBank of National Center for Biotechnology Information (NCBI) in EST database level I and level II. The most significant similarity detected was with members of the Ras and Rap gene family. NOEY2 shares 58% amino acid homology with Rap1A, 56% with Rap1B, 58% with Rap 2, 61% with Rap2B, 51% with c-K-Ras and 54% with H-Ras. The NOEY2 gene ORF exhibits three features similar to those of Ras/Rap family members: (a) a highly conserved GTP binding domain, (b) a putative effector domain YLPTIENTY (SEQ ID NO:3), and (c) the membrane localizing CAAX motif (where C is cysteine, A is an aliphatic amino acid and X is any amino acid) at the COOH terminus (FIG. 2).

Within the effector domain, however, NOEY2 differs both from Ras and Rap family members where the sequence YDPTIEDSY (SEQ ID NO:4) is found in all Ras and Rap genes. NOEY2 instead has YLPTIENTY. NOEY2 sequence had substitutions of alanine for glycine at amino acid 12 and valine for glutamine at amino acid 61 when compared to p21$^{ras}$, consistent with constitutive activation of the G protein if it behaved in a manner similar to Ras.

NOEY2 cDNA was hybridized and analyzed on Northern blots. Total RNA was isolated form confluent cell cultures using Trizol reagent (GIBCO BRL, Grand Island, N.Y.). RNA samples (15 μg) were size-fractionated by formaldehyde/agarose gel electrophoresis and transferred to a hybond-nylon membrane. The membranes were UV-cross liked, prehybridized and hybridized to $^{32}$P-labeled NOEY2 DNA probes. Hybridization was performed at 42° C. in 10× Denhard's solution and 50% formamide. 1×SSC, 10 mM EDTA, 0.1% SDS and 300 μg/ml denatured Salmon Sperm DNA. A NOEY2 message of 1.9 kb was expressed in all eleven primary normal OSE cultures and all ten primary normal breast epithelial cultures, but was lost in 11 of 12 ovarian cancer cell lines (FIG. 3A) and 9 of 9 breast cancer cell lines (FIG. 3B). One ovarian cancer cell line CAOV3 expressed NOE. Even in this line, however, NOEY2 was detected at lower levels than in normal epithelial cells. NOEY2 expression was also lost in each of 9 primary ovarian cancer cell preparations that were separated and purified from patients' ascites (FIG. 3C). Using multiple tissue blots containing polyA RNA from sixteen different normal human tissues, the NOEY2 gene was found in several other normal tissues, including heart, liver, pancreas, brain, but the highest expression occurred in normal ovary (FIG. 3D). The blots were obtained from Clontech (CLONTECH Laboratories, Palo Alto, Calif.), and Northern blots performed as described above. The inventors constructed the recombinant plasmids that express GST fusion proteins. The NOEY2 cDNA fragment which included all four GTP binding domains has been obtained by PCR™ amplification and fused in-frame into pGEX-2T vectors to produce recombinant constructs GST-NOEY2 which expressed a fusion protein with M$_r$ 53,000 (53 kDa), of which 27 kDa was GST and 26 kDa was NOEY2 derived. Large quantities of fusion protein were prepared and purified by preparative SDS-polyacrylamide gel electrophoresis (PAGE). Rabbit antiserum and monoclonal antibodies are being prepared by a standard protocol. Eight monoclonal antibodies against GST-NOEY2 have been obtained and used for detecting NOEY2 protein. By Western blot analysis, a 26 kDa protein were expressed by normal ovarian and breast epithelial cells, but could not be detected in ovarian and breast cancer cell lines (FIG. 3E).

Genes with the ability to regulate growth often have conserved counterparts in phylogenetically related organisms. The inventors examined genomic DNA from four other vertebrate species (mouse NIH3T3, Rat1A, Monkey COS7 and chicken CHO cell lines) by hybridizing with the NOEY2 probe. Under standard hybridization stringencies, homologous sequences were detected in all samples. Genomic DNA was isolated from confluent cell cultures by DNAzol reagent (GIBCO BRL, Grand Island, N.Y.). DNA samples (50 μg) were digested with restriction enzymes, separated by agarose gel electrophoresis and transferred to a hybond-nylon membrane. The Southern blot hybridization procedure was same as in Northern blot.

P1 clones from the DuPont P1 Genomic Library were screened with NOEY2 specific primer pairs Y2F3/B1-2 or Y2-19T/3Y2SP2 and used to determine their locations on human chromosome by fluorescence in situ hybridization (FISH). Probe DNA was extracted and labeled with digoxigenin-11-dUTP by nick translation. The hybridized signal was detected by anti-digoxigenin conjugated with FITC. The location of the probes was determined by digital image microscopy following FISH and localized by the fractional length from the p-terminus (Flpter). NOEY2 has been mapped to chromosome 1p31 and Bacs obtained. LOH at 1p31 has been observed in a significant percent of breast and ovarian cancer (Kitayama et al., 1989). Using an intragenic TA dinucleotide repeat length polymorphism as a marker, the inventors have detected LOH within the NOEY2 gene in 9 of 18 ovarian cancers (50%).

Sense and antisense constructs of NOEY2 were transfected with lipofectamine into three ovarian cancer cell lines (OVCA433, OVCA429, Hey), one breast cancer cell line (SKBr3) that did not express NOEY2 and one lung cancer cell line that did express NOEY2 (A-549) (FIG. 4A). NOEY2 cDNA was excised from the EcoRI cloning sites from the Bluescript/λZapII® vector. This fragment was 1 Kb in size and included the ORF, it was inserted into the pcDNA3 neo eukaryotic expression vector (Invitrogen, San Diego, Calif.) in the sense and antisense orientation. The constructs were transfected into three ovarian cancer cell lines (OVCA433, OVCA429, Hey), one breast cancer cell lines (SKBr3) and one lung cancer cell line (A549) by lipofectamin method (GIBCO BRL Grand Island, N.Y.). As controls, similar amounts of carrier DNA and the vector DNA only were also transfected into cells. The mixtures of lipofectamin and constructs were exposed to the cells for six h at 37° C., then replaced by cell culture medium. After incubation for 48 h at 37° C., transfected cells were trypsinized and seeded into 100 mm dishes, select medium with G418 400 μg/ml to 1000 μg/ml was added to the cells. Replaced the select medium every four days. After 2–3 wk, transformed colonies began to appear, the dishes were stained by 0.1% coomassie blue in 30% methanol and 10% acetic acid.

To explore mechanisms underlying growth inhibition, the inventors have determined the effect of NOEY2 expression on other growth regulatory molecules. NOEY2 sense constructs, but not antisense constructs, strongly inhibited cyclin D1 promoter activity when cotransfected with a plasmid containing the luciferase gene under the control of the cyclin D1 promoter in Saos-2 and NIH3T3 as well as ovarian and breast cancer cell lines whose growth could be inhibited (FIG. 4B). As cyclin D1 is required for G1-S progression (Albanese et al., 1995), the potent inhibition of the cyclin D1 promoter activity by NOEY2 could contribute to the observed growth inhibition. Cyclin D1 expression is upregulated in 25–30% of ovarian cancers in the absence of gene amplification (Worsley et al., 1997).

Multiple growth factors, including epidermal growth factor (EGF), insulin, hydrocortisone and bovine pituitary extract (BPE) can stimulate growth of primary breast (FIG. 5A) and ovarian epithelial cells. Increased growth rates were associated with down-regulation of both NOEY2 and p21$^{WAF1/CIP1}$ in Northern analysis (FIG. 5B). To examine the interaction between NOEY2 and p21$^{WAF1/CIP1}$, an NOEY2 fragment that included the entire ORF was fused in frame with a plasmid that contained a triple hemagglutinin (HA) repeat and this HA-NOEY2 construct was transfected into NIH3T3 cells, two color immunofluorscent staining demonstrated that HA-NOEY2 transfectants had higher $p21^{WAF1/CIP1}$ protein expression than did nontransfected cells or cells transfected with a HA-Erk2 cDNA (FIG. 6A, FIG. 6B, FIG. 6C, and FIG. 6D). The $p21^{WAF1/CIP1}$ protein has been shown to arrest cell growth by inhibition of cyclin dependent kinases (Xiong et al., 1993). While $p21^{WAF1/CIP1}$ is a p53 inducible gene (El-Deiry et al., 1993), induction of this inhibitor has also been observed in the absence of functional p53 (Michieli et al., 1994). Similarly, transfections of NOEY2 into the Hey (p53 wild type), SKBr3 (p53 mutant) and Saos-2 (p53 null) cells exerted p53 independent inhibition of cyclin D1 promoter activity. These observations collectively suggest that NOEY2 functions as a negative regulator of cell growth probably through interaction with components of cell cycle control.

The genomic sequence of NOEY2 contains two exons and one intron. The inventors have sequenced the hole coding region and 1.9 Kb upstream to identify putative mutations in NOEY2 using DNA from different cell lines. Eight of the 18 tumor cell lines (SKOv3, OVCAR-3, OVCA429, OVCA432, BT20, MCF-7, MDA-MB-432 and SKBr3) have a heterozygous A to G substitution at −750 (44%), which is also presenting 5 of 36 primary ovarian cancer DNA samples (14%) and 20 of 100 DNA samples from normal peripheral leukocytes (20%). This sequence variation appears to be a functionally significant polymorphism in that induced mutation of A to G at −750 reduces the activity of the NOEY2 promoter by more than 50% in OSE and NBE cells (FIG. 8). IN addition, sequence abnormalities have been found in the promote region of NDA-MB-468 with C(−13)G in one allele and G(+99)A in the other. CAOv3 and BT20 each have a G(coding-231)A alteration encoding an Ala to Thr change, which also was found in 6 of 110 normal control DNA samples (5%). Only one allele of NOEY2 was expressed in each of these cell lines as assessed by RT-PCR™ cDNA sequence analysis and by digestion with HhaI suggesting acquired methylation or germ line imprinting. Hypermethylation of CpG islands surrounding the TATA box was found in 2 or 8 breast cancer cell lines (MDA-MB4-35 and MDA-MB-453). Three OSE, 2 NBE DNA, 9 ovarian cancer and 4 breast cancer cell lines exhibited partial methylation at this site. Expression of only one NOEY2 allele may be important, given the high rate of LOH and the frequent occurrence of a functionally significant polymorphism at −750 in the promoter region. Considering that lack of NOEY2 expression has been observed in more than 90% of ovarian and breast cancer cell lines and freshly isolated ovarian cancer cells, multiple mechanisms, including mutation, hypermethylation and transcriptional regulation may be important in the loss of NOEY2 expression in tumors. The ability of NOEY2 to inhibit tumor growth combined with LOH and genetic alterations suggest that NOEY2 functions as a tumor suppressor.

5.2 Example 2

Significance of NOEY2 Expression Loss in Ovarian Cancers

NOEY2 expression may be assessed at the level of message (with probes and primers already available) and protein (with antibodies developed as described below). Expression may be correlated with histology, stage, grade, outcome and response to chemotherapeutic agents. DNA, RNA and protein may be obtained from primary ovarian epithelial cell cultures, ovarian cancer cell lines, primary ovarian cancer cells from patients' ascites and cryopreserved normal ovary and tumor tissues. Ascites tumor cells may be purified to >95% homogeneity using techniques developed in the inventors' laboratory (Hurteau et al., 1994).

5.2.1 Materials and Methods 5.2.1.1 Northern Blot Analysis

NOEY2 cDNA probe was labeled with $P^{32}$-dCTP by random primer. Fifteen micrograms of total cellular RNA was separated in 1.2% formaldehyde-agarose gels and immobilized on a Hybond-N membrane by standard capillary transfer and UV crosslinking, and then prehybridized and hybridized to NOEY2 probe in 50% formamide. 1×SSC. 10× Denhardt's solution, 10 mM EDTA, 0.1% SDS and 300 µg/ml denatured salmon sperm DNA at 42° C. for 24 h. The blot was washed at 42° C. in 0.1×SSC 0.1% SDS before exposure. Hybridization of the same blot to a probe for 18S-rRNA indicates an equal amount of RNA in all lanes.

5.2.1.2 Cell Culture of Primary OSE Cells and Ovarian Cancer Cell Lines

Cultures of primary normal OSE cells were obtained by gently scraping the surface of ovaries from patients undergoing surgery for nonmaligant gynecological diseases. Epithelial cells were cultured in OSE medium (MCDB105/199 medium supplemented with 15% fetal calf serum and 10 ng/ml EGF). Ovarian cancer cell lines were maintained as previously described (Xu et al., 1991).

5.2.1.3 Purification of Ovarian Cancer Cells from Patient's Ascites

Cryopreserved ovarian cancer ascites tumor cells were thawed and purified to >95% homogeneity using discontinuous Percoll density gradient centrifugation and immunoaffinity removal of CD45 positive inflammatory cells as previously described (Hurteau et al., 1994).

5.2.1.4 Transfection and Colony Formation Assay

NOEY2 cDNA (1 Kb) was released from the EcoRI cloning site in the Bluescript/Lambda ZapII® vector and inserted into the pcDNA3-neo eukaryotic expression vector (Invitrogen, Carlsbad, Calif.) in sense and antisense orientations. The constructs were transfected into three ovarian cancer cell lines (OVCA433, OVCA429, Hey), one breast cancer cell line (SKBr3) and one lung cancer cell line (A-549) using lipofectamine. After incubation for 48 h at 37° C., transfected cells were trypsinized and seeded into 100 mm dishes. Selection medium with G418 (400 µg/ml to 1000 µg/ml) was added. Two wk later, colonies were stained by 0.1% Coomassie blue in 30% methanol and 10% acetic acid.

5.2.1.5 Two Color Immunofluorescent Staining

The HA-NOEY2 and HA-Erk2 constructs were transfected into NIH3T3 cells using lipofectamine. After 24 h, cells were fixed with 4% paraformadehyde permeabilized with 0.5% Triton X-100 and stained with an anti-$p21^{WAF1/CIP1}$ polyclonal antibody (c-19) (Santa Cruz) and anti-rabbit IgG FITC conjugate followed by subsequent incubation with an anti-HA-rhodamine conjugate (Boehringer Mannheim, Indianapolis, Ind.).

5.2.1.6 Genbank Accession Number

NOEY2 has the GenBank accession number U96750.

5.2.1.7 Antibody Preparation and Purification

To facilitate studies of protein expression, specific antibodies may be prepared against recombinantly derived NOEY2 fusion proteins. The inventors have already constructed three recombinant plasmids that express GST fusion proteins. Three fragments (of 0.8 Kb, 0.6 Kb and 0.4 Kb) have been obtained from NOEY2 cDNA clones by PCR™ amplification. One included all four GTP binding domains, the second included the third and fourth domains and the third included the first and second domains. The GST-NOEY2 fusion proteins were prepared and purified by preparative SDS-polyacrylamide gel electrophoresis (PAGE). Rabbits have been immunized with the NOEY2 fusion proteins and initial bleeds may be available in the next few wk. This approach has been utilized to generate antibodies against a number of proteins including signaling molecules (Gibson et al., 1993). To enrich for antibodies recognizing only NOEY2 protein determinants, two affinity columns may be prepared, one with GST protein and the other with the fusion protein. Antisera may be passed through the fusion protein/sepharose column and eluted with glycine buffer (pH 2.3). The eluate may be neutralized and passed through the GST column several times to remove antibody directed against GST.

Anti-NOEY2 murine monoclonal antibodies may be prepared and screened using standard protocols which the inventors have previously used in development of OC125 (Bast et al., 1981) which binds CA125 antigen (Bast et al., 1983). Hybridomas may be screened against the immunizing GST-fusion protein and against GST by ELISA to identify those which specifically react with NOEY2. Polyclonal and monoclonal antibodies may be assessed for utility in immuno-precipitation, western blotting, immunohistochemistry and immunofluorescence utilizing the immunizing fusion protein as control.

5.2.1.8 Statistical Analysis

Patient outcome may be characterized by one of the time-to-event variables 1) survival time or 2) disease-free survival (DFS) or by the binary variable indicating either 3) response or 4) partial response to chemotherapy (Cox, 1972; Modern Applied Statistics with S-Plus, 1994; Grambsch and Therneau, 1994; Harrington and Fleming, 1991). Each of these evaluations may be carried out by regression analysis, with the patient outcome as the response variable in the regression model and NOEY2 included as a predictive covariate along with the established predictors disease stage, disease grade, amount of residual disease post surgery, and other molecular markers, including HER-2, EGFR, fms, and p53. Because NOEY2 is recorded as an ordinal variable taking on the values 0,1,2,3 or 4, it may be evaluated first as a numerical covariate and subsequently as a categorical covariate in each regression analysis. For each patient outcome, specific questions to be addressed include whether NOEY2 per se is predictive, if so whether the effect of NOEY2 on patient outcomes survival of DFS changes over time, and whether any significant effect of NOEY2 persists in the presence of the established predictors noted above. Relationships between pairs of covariates may be evaluated by computing standard Pearson correlations and Spearman rank correlations between numerical variables and constructing their smoothed scattergrams, by cross-tabulating categorical variables, and by carrying out Kruskal-Wallis or Wilcoxon-Mann-Whitney tests to assess the change of a numerical variable across a categorical variable.

Covariate effects on each of the time-to-event outcomes survival and DFS may be evaluated using the Cox proportional hazards regression model (Cox, 1972) and its extensions (Harrington and Fleming, 1991; Therneau, 1994). Goodness-of-fit may be evaluated using the methods of Therneau et al., (1990) and Lin (1991). Smoothed martingale residual plots may be used to determine if any of these markers have a possible "threshold effect" on survival or DFS (Kornblau et al., 1995; Hilsenbeck and Clark, 1996). Possible time-varying covariate effects may be identified and evaluated using the method of Grambsch and Therneau (Grambsch and Therneau, 1994). The amount of variation in survival or DFS explained by NOEY2 and the other covariates may be quantified using the methods of Korn and Simon (1990) and Schemper and Stare (1996). Statistical software for fitting these models has been obtained from T. Therneau (1994).

Effects of NOEY2 and the other covariates on the binary patient outcomes response or partial response may be evaluated using binomial regression, including logistic regression and probit analysis as special cases. Goodness-of-fit may be evaluated using the methods of Pregibon (1982).

5.2.1.9 Sequencing and Methylation

After SSCP analysis of the coding region. PCR™ fragments with abnormal mobility were cloned into the PCR-Script Amp SK (+) cloning vector (Stratagene, LaJolla, Calif.). More than 10 clones of each sample were sequenced using an ABI PRISM 377 DNA automatic sequencer and a Big Dye™ terminator cycle sequencing kit. Upstream promoter region sequences (1.9 Kb) were amplified by four pairs of primers with a −21M13 tail. Purified PCR™ products were directly sequenced using −21M13 Dye™ primer cycle sequencing kit (PE Applied Biosystems). Methylation was measured using restriction enzymes XbaI/SacII in CpG islands surrounding the TATA box by Southern blot analysis.

5.2.1.10 Promoter Activity Assay

NOEY2 promoter fragment was amplified from genomic DNA by PCR™ and cloned into pGL2, a vector with luciferase reporter, its activity was tested by luciferase assay system (Promega, Madison, Wis.). A −750A to G mutant construct was made by site directed mutagenesis (Stratagene). Mutation was confirmed by sequencing.

5.2.2 Discussion

The inventors expect that a loss of NOEY2 will be observed in a significant fraction of advanced stage and high grade ovarian carcinomas. The inventors predict that NOEY2 may be lost in a smaller fraction of grade I and lower stage tumors. Moreover, the inventors predict that loss of NOEY2 may be a rare event in borderline tumors, but that this might correlate with high risk of recurrence. Given the effects of NOEY2 on the growth of ovarian cancer cell lines, the inventors predict that the loss of NOEY2 may correlate with a poor prognosis in frankly invasive lesions. Although the inventors predict that loss of NOEY2 may correlate with conventional risk factors, NOEY2 may be of even greater interest if its loss correlates with shortened survival but not with these conventional factors. Loss of NOEY2 may or may not correlate with drug resistance. If this were the case for some drugs and not for others, the marker might prove particularly valuable in choosing primary therapeutic regimens for individual patients. Lack of a correlation with drug resistance would suggest that loss of NOEY2 was a marker for aggressive biological behavior. Interaction with other biological markers may be of particular interest. If NOEY2 inhibits signaling through the Ras pathway the inventors would anticipate amplification of the poor prognosis associated with persistence of EGFR, overexpression of HER-2 and novel expression of fms. In contrast to tumors at other sites, the inventors' studies with ovarian cancer have demonstrated a high correlation between mutation and overexpression of mutant p53 protein. Considered as a single marker, overexpression of p53 has not correlated consistently with prognosis in ovarian cancer. If NOEY2 plays a role in apoptosis, the mutation and consequent overexpression of p53 might be a poor prognostic marker in that subset of ovarian cancers that have lost NOEY2.

5.3 Example 3

Mechanism of Loss of NOEY2 Expression

NOEY2 has been mapped to 1p31. The inventors' data for 6 highly polymorphic markers located at or near 1p31 indicates that LOH occurred in 5 of 12 informative tumors from matched pairs of ovarian cancer and peripheral blood samples. This rate of 42% loss is higher than that expected given the approximately 20% LOH rate throughout the genome observed in advanced ovarian cancer.

Using the 1p31 chromosomal localization and a series of 8 currently available highly polymorphic markers for 1p31, the inventors may undertake LOH analysis of the region around NOEY2 in DNA from ovarian cancers and normal peripheral blood leukocytes of the same patients. In addition to the inventors' own series of approximately 25 matched pairs currently under analysis, the inventors may assess 100 matched pairs of tumor and normal peripheral blood leukocytes with histological and outcome evaluation. The inventors may correlate LOH at 1p31 with outcome as well as with stage, grade and histology.

Southern blotting analysis has failed to detect abnormalities in the structure of the NOEY2 gene in 6 of 6 ovarian cancer cell lines assessed. The inventors may extend these studies to include the nine freshly isolated ovarian cancer ascites samples from patients which the inventors have already demonstrated do not express detectable amounts of NOEY2 RNA. If, as expected, the NOEY2 gene is intact in the freshly isolated samples as it is in the already characterized tumor cell lines, it is most likely that the loss of NOEY2 expression is due to changes in methylation status rather than due to deletion or to a transcriptional mechanism.

As noted above, hypermethylation is a relatively frequent mechanism for loss of expression of tumor suppressor genes such as VHL, p16 and RB. The inventors may thus assess the effect of decreasing methylation with 5-azacytidine or 5-aza-2-deoxycytidine on expression of NOEY2 in ovarian cancer cell lines. The inventors may also assess whether the promoter for NOEY2 contains CpG islands and is hypermethylated in ovarian cancers as compared to normal epithelium. Alternatively, mutations might be found in the promoter region which may be sequenced in those cell lines and tumors where downregulation of NOEY2 expression cannot be attributed to other mechanisms.

5.3.1 Methods

LOH analysis is performed with 8 commercially available highly polymorphic markers for 1p31 using techniques published previously. The analysis of the 100 samples utilizes a semi-automated microtiter system for analysis providing rapid throughput for the 100 samples and 8 primer pairs.

Southern blotting is performed using standard techniques on DNA isolated from highly purified (>95%) ovarian cancer cells isolated from the ascitic fluid of ovarian cancer patients and tumor cells isolated from solid tumors (samples with >80% tumor cells).

Hypermethylation of promoter regions may be sought in ovarian cancers that lack NOEY2 expression without LOH or an evident abnormality on Southern blots. Ovarian cancer cell lines demonstrated not to express NOEY2 and shown to have a relatively intact NOEY2 gene on Southern analysis are cultured for 48 h to 2 wk in 5-azacytidine (5 M) or 5-aza-2-deoxycytidine (0.75 M) to determine if this alters the expression of NOEY2 as assessed by Northern blot analysis.

The inventors contemplate two BACs may be most appropriate for promoter isolation. Analysis of the NOEY2 promoter is conducted to determine whether the promoter for NOEY2 contains CpG islands. The methylation status of the promoter for NOEY2 in ovarian cancer cell lines is assessed by restriction analysis with methylation-sensitive restriction enzymes including HhaI, NotI and SacII. Alterations in enzyme sensitivity may be due to changes in methylation, and this is analyzed by comparing the restriction patterns with those of normal ovarian epithelial cells which express NOEY2 and with ovarian cancer cell lines incubated with 5-azacytidine or 5-aza-2-deoxycytidine.

To determine whether any CG rich regions in the promoter of NOEY2 are hypermethylated in cells in vivo, ovarian cancer cells may be isolated and purified from ovarian cancer patient's ascites. Ovarian cancer cells can be purified to over 95% homogeneity (Hurteau et al., 1994) and may routinely survive in culture for at least one month. Such cells are assessed for the effect of 5-azacytidine or 5-aza-2-deoxycytidine on NOEY2 expression and restriction analysis with methylation sensitive restriction enzymes including HhaI, NotI and SacII as described for cell lines above.

If the methylation sensitive restriction enzyme approach described above fails to detect methylation of the NOEY2 promoter in freshly isolated cells, a method for methylation detection may be utilized which depends upon the chemical modification of cytosine to uracil by bisulfite treatment (Frommer et al., 1992). This technique is less sensitive to contamination of tumor by normal cells and is more sensitive in detecting hypermethylation than is the restriction enzyme approach described above. In this method, genomic DNA is bisulfite treated and fragments from within the promoter containing region cloned using PCR™ and the TA vector and then subjected to sequence analysis. As bisulfite treatment converts unmethylated cytosines to uracil, but leaves methylated cytosines intact, sequence analysis may reveal the conversion of unmethylated cytosines to thymidines, while methylated cytosines may appear as cytosines in the sequencing analysis. Sequencing of a number of TA vector plasmids from tumors may demonstrate the frequency of methylation of the NOEY2 promoter.

Transcriptional regulation may be evaluated in those cell lines and tumor specimens where loss of NOEY2 expression cannot be attributed to other mechanisms. At least 500 bp of the NOEY2 promoter may be cloned from the BACs already identified that contain the NOEY2 coding sequence. The promoter may be ligated to luciferase as a reporter gene (Gum et al., 1996). Transient expression is sought after transfection of ovarian cancer cell lines that lack NOEY2 expression and, as a positive control, normal ovarian surface epithelial cells that express NOEY2.

5.3.2 Discussion

The inventors' data suggest that more extensive LOH analysis of 1p31 may demonstrate LOH for 1p31 in more than one third of ovarian cancers. The inventors predict that the NOEY2 gene may be intact in ovarian cancers as suggested by Southern blot analysis and that the NOEY2 promoter may be hypermethylated in a fraction of tumors when compared to normal ovarian epithelium. If sought, mutations may well be found in a fraction of those promoters that are not hypermethylated. Transcriptional regulation may be the least frequently occurring abnormality, however, cell lines that exhibit such an abnormality are valuable for elucidating mechanisms of physiologic as well as pathologic regulation of NOEY2 expression.

5.4 Example 4

Effects of NOEY2 Expression on Ovarian Cancers

NOEY2 expression is consistently lost from ovarian cancer cell lines and from freshly isolated cancer cells from patient's ascites. Further, data indicate that expression of NOEY2 decreases clonogenic activity of ovarian and breast cancer cells in a transient transfection assay. This suggests that NOEY2 may alter characteristics of ovarian cancer cells which could lead to initiation or progression of ovarian cancer. The inventors contemplate that upregulation of NOEY2 may inhibit growth, block invasion, reduce metastatic potential, decrease angiogenesis or trigger apoptosis, whereas downregulation of NOEY2 may stimulate growth, increase invasive potential, augment metastatic potential, enhance angiogenesis or inhibit apoptosis. Ras and Rap proteins require appropriate localization and an intact effector domain to mediate their functions. Mutagenesis of any of the amino acids in the CAAX box or the YDPTIEDSY domain impairs the ability of Ras to transform cells.

Conditional expression of normal NOEY2 is used to test whether upregulation of NOEY2 inhibits growth, blocks invasion, reduces metastatic potential, or decreases angiogenesis, and uses a dominant negative NOEY2 (N17-NOEY2 modeled on other dominant negative small G protein constructs) to determine whether downregulation of NOEY2 activity may stimulate growth, increase invasive potential, augment metastatic potential, or enhance angiogenesis. As transient expression of NOEY2 inhibits colony forming activity, the inventors assess whether expression of NOEY2 may alter cell cycle progression or direct cells to apoptosis.

Growth inhibition by a number of mediators including heregulin can require an intact p53 pathway or an intact RB pathway. Approximately 50% of all ovarian cancers have mutations or deletions in p53. All of the ovarian cancer cell lines thus far assessed for growth inhibition by NOEY2 contained normal p53. Although mutations in RB or p16 are rare in freshly isolated ovarian cancer cells, the inventors have identified ovarian cancer cell lines with deletions or mutations in p53, deletions in p16 and cell lines with deletions in RB.

The effector domain of Ras is required for the transforming activity of the protooncogene. The effector domain of Ras and Rap family members is critical for Ras and Rap functions. The effector domain of NOEY2 differs from that of Ras and Rap family members. Site directed mutagenesis may be utilized to convert the effector domain of NOEY2 to the identical sequence to that found in Ras and Rap family members.

5.4.1 Transient NOEY2 Expression

Normal and epitope-tagged NOEY2 has been inserted into CMV and SV40 promoter driven expression constructs. In order to distinguish transfected NOEY2 from native NOEY2 and to demonstrate expression of NOEY2, the NOEY2 gene has been epitope tagged with an hemagglutinin (HA) epitope using a triple HA repeat plasmid. The HA epitope was added to the N terminus of NOEY2 so as to be distant from the potential myristylation site at the C terminus of NOEY2.

5.4.2 Conditional Expression

Ovarian cancer cell lines that lack NOEY2 expression may be transfected to provide conditional expression of NOEY2. Studies demonstrated that stable NOEY2 transfectants could not be developed likely because constitutive NOEY2 expression suppresses cell growth and/or causes cell death. The Tet-Off and Tet-On Gene Expression System provides regulated, high-level gene expression as initially described by Gossen and Bujard (1992). In the first transfection, the Tet-On regulatory protein is introduced into ovarian cancer cell lines by transfection of a "regulator plasmid"-pTet-On (cells already isolated). NOEY2 and epitope tagged NOEY2 have already been inserted into the pTRE (plasmid created) which may be introduced into cells expressing the Tet On plasmid to create double-stable Tet-On cell lines which may express NOEY2 only in the presence of tetracycline. NOEY2 gene expression should be negligible in the absence of tetracycline and induced by the addition of tetracycline. The Tet-on system has the advantage over most inducible systems in having very low levels of non-induced expression (leakiness) and in being compatible with induction both in vitro and in vivo.

5.4.3 Colony Formation

The ability of mutation of NOEY2 to alter its activity in colony formation activity may be assessed as described. Mutant or normal NOEY2 may be transfected into ovarian cancer cells along with a hygromycin resistance plasmid. Cells may be incubated with hygromycin for 2–3 wk and colonies assessed by staining with 1% Coomassie blue in 30% methanol and 10% acetic acid.

5.4.4 Proliferation, Invasiveness and Apoptosis

Proliferative capacity may be judged by $^3$H-thymidine incorporation, growth by MTT assay and clonogenicity by growth in soft agar in the presence and absence of tetracycline. Invasion of matrigel membranes may be studied using techniques already established in the inventors' laboratory (Berchuck et al., 1992). Apoptosis may be evaluated by morphology, free DNA ends (Apoptag kit), DNA ladders and loss of membrane asymmetry (Annexin V staining).

5.4.5 In Vivo Tumorigenicity

The methods for murine tumorigenicity assays have been described. Briefly, the parental ovarian cancer cell lines-SKOv3 and Hey are tumorigenic in nude mice (HEY forms subcutaneous tumors whereas the HEY-A8 cell line forms intraperitoneally tumors and metastasizes). Five to $10 \times 10^6$ stably transfected tumor cells from each cell line may be injected subcutaneously and intraperitoneally into athymic nude mice. All recipients should develop tumors within 2 wk. If the behavior of transfected cells reflects the parental phenotype, tumor cells may form nodules, ascites, and metastasize to the lungs where nodules can be detected grossly and by histologic examination. However, when doxycycline is given to the mice at a dosage sufficient to establish an appropriate doxycycline concentration, NOEY2 gene expression in the tumor cells should be upregulated and growth inhibited. Doxycycline can be delivered either orally as a glucose suspension or optimally as a long release pellet (Innovative Research). Subcutaneous tumors may be measured twice a wk and animals examined every other day for ascites.

5.4.10 Discussion

NOEY2 inhibits colony forming activity of breast and ovarian cancer cell lines. The effects of NOEY2 may be expressed at many levels by inhibiting proliferation, colony formation, anchorage independent growth, invasiveness and ability to form tumors in nude mice. The global inhibitory activity of NOEY2 may extend to an ability to block production of growth factors and angiogenic factors such as VEGF. NOEY2 may thus decrease the ability of tumors to grow in the peritoneal cavity, to metastasize and to enlarge due to lack of neovascularization. Data indicate that even 48 h following transfection of NOEY2, there are decreased levels of reporter constructs and markedly decreased numbers of transfected cells as indicated by contransfection of the GFP plasmid. This suggests that NOEY2 expression is likely to induce apoptosis.

5.5 Example 5

Mechanism of NOEY2 Interference with Signal Transduction

Data indicate that NOEY2 appears to function as a tumor suppressor in ovarian cancer. NOEY2 could function as a tumor suppressor by interfering with signal transduction from surface receptors, by interfering with signaling cascades, or by altering the function or expression of proteins required for cell cycle progression. Alternatively, NOEY2 may target cells for apoptosis. This specific aim may attempt to identify the site at which NOEY2 mediates it tumor suppressor activity.

By analogy with members of the Rap family with which NOEY2 shares similarity in the effector domain, the product of the NOEY2 gene may act as an antagonist of Ras p21 protein signaling. Ras provides a convergence point for signal transduction induced by tyrosine kinase linked and G protein linked receptors. A major pathway activated by p21-Ras is the Ras-Raf-MEK-ERK (MAPK) module which plays an essential role in cell growth and differentiation. Due to its structural similarities to p21-Ras, NOEY2 protein may compete for the upstream or downstream regulators and effectors of Ras. This is a suggested mechanism of action for the ability of Rap family members to decrease Ras-mediated signaling.

By analogy to members of the Rac family with which NOEY2 has homology in the effector domain, the product of the NOEY2 gene may act as an agonist of the JNK pathway. Similar to the p21-Ras MAPK cascade, the JNK pathway includes a similar G protein-cascade module, RAC-MEKK1-SEK/MKK4-JNK/SAPK. In contrast to MAP kinases, JNK has been linked to stress response, growth inhibition and programmed cell death. Since the JNK pathway is a negative regulator of cell proliferation, an agonistic activity of NOEY2 in this pathway could explain the tumor suppressor-like activity of NOEY2. Thus it is possible that NOEY2 protein inhibits cell growth through activation of the JNK pathway.

Since NOEY2 decreases colony forming activity, it is likely that it inhibits cell cycle progression. The inventors may assess whether intact p53, p16 or RB are required for NOEY2 to inhibit colony forming cell activity. If the p53 or p16/RB pathways are obligatory for NOEY2 inhibition of colony forming cell activity, the inventors may assess the effect of NOEY2 on activation of these pathways.

As an alternative to inhibition of cell cycle progression, NOEY2 may decrease colony forming cell activity through induction of apoptosis. If NOEY2 increases the rate of apoptosis, the inventors may assess the ability of NOEY2 to alter expression of members of the Bcl-2 family of proteins which play a major role in the regulation of programmed cell death in ovarian cancer cells according to the inventors' data.

Small G proteins are active in the GTP bound state and inactive in the GDP bound state. Several of the amino acids present in NOEY2, if present in Ras would result in activating mutations. One may assess whether the GTP/GDP ratio of NOEY2 is similar to that of normal Ras in resting fibroblasts or whether it is similar to that of activated Ras. The localization of Ras and other small G proteins through myristylation is critical for their function. One may determine the localization of NOEY2 in ovarian epithelium. Because NOEY2 may function at a number of levels in suppressing tumorigenesis, it may be interesting to determine whether NOEY2 inhibits the transforming activity of growth factor receptors (EGFR, HER-2), intracellular tyrosine kinases (src), activated Ras and downstream mediators of Ras (RAF).

It has been well established that stimulation of tyrosine kinase receptors (with EGF) or G-protein coupled receptors (with lysophosphatidic acid) activates MAPK through the Ras-Raf-MEK-ERK pathway. If NOEY2 expression indeed impairs EGF- or LPA-induced MAPK activation, further studies using activated Ras, Raf or MEK may be conducted to determine where NOEY2 protein inhibits MAPK activation, e.g. upstream or downstream of Ras. Expression of activated forms of Ras (V12 Ras), Raf (v-raf) or MEK causes constitutive activation of MAPK. Expression plasmids carrying V12 Ras, v-raf or MEK may be cotransfected with NOEY2 or an empty vector. MAPK activity in transfected cells may then be determined using an epitope-tagged cotransfected MAPK. A complete or partial inhibition of Ras-, Raf- or MEK-stimulated MAPK activation by NOEY2 would be expected if NOEY2 inhibits the Ras signaling cascade.

The RAC and CDC42 small G proteins activate the JNK signaling pathway which negatively regulates cell proliferation targeting cells to programmed cell death. As the effector domain of NOEY2 has a sequence which is similar to that of RAC and CDC42, the inventors may assess whether NOEY2 activates the JNK kinases. The inventors may also assess whether NOEY2 is required for activation of the JNK kinases by TNF, IL1, FAS, lysophospholipids, and protein synthesis inhibitors (anisomycin) all of which the inventors have shown activate JNK kinases in ovarian cancer cells or activate ovarian cancer cells and have been demonstrated to activate JNK kinases.

The inventors may assess whether intact p16 or intact RB is required for NOEY2 to mediate inhibition of colony formation. If p16 or intact RB is required for the inhibition of cell proliferation, the inventors may assess the effect of NOEY2 on p 16 and cyclin D1 levels, on CDK4 kinase activity and on RB phosphorylation status. The inventors may also assess whether normal p53 is required for NOEY2 to mediate inhibition of colony formation. If p53 is required for NOEY2 to mediate inhibition of colony formation, the inventors may assess whether NOEY2 alters expression or stability of p3, expression of cyclin D1, CDK2 kinase activity and expression of the P21/WAF1/CIP mediator of p3 action.

5.5.1 Methods

The inventors have developed polyclonal (9613, 9617) and eight monoclonal (17G6, 15E11, 12C7, 6B4, 6D2, 12A8, 3H2 and 16C6) antibodies to NOEY2 with techniques that the inventors have successfully utilized in the past. The inventors have tagged NOEY2 with HA-epitope allowing the inventors to distinguish transfected NOEY2 from endogenous NOEY2. Until polyclonal or monoclonal antibodies specific to NOEY2 are available, the inventors may utilize transfection of epitope-tagged NOEY2 to demonstrate function. The HA antibody (for which the inventors have access to the hybridoma) immunoprecipitates tagged proteins and works well in Western blotting.

GTP/GDP ratios NOEY2 GTP/GDP ratios are assessed using $^{32}PO_4$-loaded cells as reported previously for determining Ras GTP/GDP ratios (Kruk et al., 1990). NOEY2 may be immunoprecipitated and washed. GTP and GDP may be separated by thin layer chromatography and $^{32}P$-containing GTP and GDP identified by autoradiography and comparison with ninhydrin stained standards.

5.5.2 NOEY2 Localization

Normal ovarian epithelial cells which contain more NOEY2 protein than ovarian cancer cell lines may be used. Cells may be labeled with $^{35}S$-methionine for 3 h and nuclear, cytoplasmic and membrane fractions prepared by differential centrifugation. Equivalent amounts of each sample may be immunoprecipitated and analyzed by SDS-PAGE. To complement $^{35}S$-methionine labeling, NOEY2 may be western blotted to determine localization. If insufficient NOEY2 is present to allow direct western blotting, NOEY2 may be immunoprecipitated from each cellular fraction and localization determined by western blotting of each fraction. NOEY2 may be identified by immunoprecipitation of transfected HA epitope tagged NOEY2 until such time as NOEY2 antibodies are available. Normal ovarian epithelial cells can be effectively transfected.

To complement subcellular fractionation, HA may be immunolocalized using confocal microscopy and immuno-electron microscopy. The HA antibody and epitope tagged NOEY2 cannot be utilized for this purpose due to cross-reactivity of the HA antibody with cellular proteins. These studies may be performed when appropriate affinity purified polyclonal or monoclonal antibodies are available.

5.5.3 Target of Signaling Inhibition

NOEY2, antisense NOEY2 and dominant negative NOEY2 may be cotransfected at a 5:1 ratio with activated erbB, HER-2, src, Ras and RAF into NIH 3T3 cells to ensure that NOEY2 is present in all transfected cells. The effect of NOEY2 on focus forming activity induced by each oncogene may then be assessed. The inventors have NIH3T3 cells in the laboratory with a low baseline focus forming rate which are appropriate for this assay. NIH 3T3 cells constitutively overexpressing myc are available, which may be used to determine whether NOEY2 may inhibit the focus forming activity of these oncogenes in the presence of high levels of myc.

5.5.4 Signal Transduction

The ability of NOEY2 to alter activation of Ras, MAPK, or JNK may be assessed by cotransfection of NOEY2, antisense NOEY2, and dominant negative NOEY2 (not epitope tagged) and an epitope tagged target. Alternatively if conditional tetracycline-induced NOEY2 containing cell lines are developed, the inventors may study endogenous targets with and without Tet induction of NOEY2 expression. The inventors may also assess whether NOEY2 affects the ability of activation of tyrosine kinase linked receptors (EGF and heregulin), activation of protein kinase C (phorbol esters) and G protein linked receptors (lysophosphatidic acid) to stimulate the activity of these signaling molecules. Although Ras and MAPK activity are elevated in several of the cell lines under study, Ras can be incrementally activated by each of these agents in ovarian cancer cell lines (Patton et al., 1994).

GTP/GDP ratios on Ras may be determined as described above with $^{32}P$ labeling and immunoprecipitation of epitope-tagged Ras with the anti-HA antibody or in conditional NOEY2 expressing cells with the Y13-259 anti-Ras antibody (hybridoma in house).

5.5.5 MAPK Assay

The effect of NOEY2 on MAPK activation may be assessed by four assays: 1) gel mobility shift. 2) Western blotting with an activation specific epitope antibody (UBI) 3) in gel kinase assay (the epitope tagged MAPK runs at a different size from the native MAPK) and 4) in vitro kinase using MBP as a substrate (Xu et al., 1994).

5.5.6 JNK Assay

JNK activity may be determined by in vitro kinase assay using a GST-N-terminal portion fusion protein of Jun as substrate. The inventors may also assess whether expression of NOEY2 or of dominant negative (N17 NOEY2) may alter anisomycin, TNF, IL1 or FAS induced activation of JNK.

5.5.7 CYCLIN D1 Expression

If conditional tetracycline-induced NOEY2 containing cell lines are developed, the inventors may study endogenous cyclin D1 levels with and without Tet induction of NOEY2 expression. Alternatively, if conditional NOEY2 containing cell lines are not available, the inventors may utilize cotransfection of NOEY2 and a cyclin D1 luciferase expression construct as a reporter.

CDK4 and CDK2 kinase activity may be assessed following immunoprecipitation using recombinant RB (UBI) as a substrate. p21/WAF1/CIP1 and p16 levels may be assessed using western blotting with UBI antibodies. RB phosphorylation may be measured by gel shift assay using RB specific antibodies (UBI). p53 levels may be assessed by immunohistochemistry and western blotting. Although p53 levels are normally low, they can be increased by transcriptional or post transcriptional mechanisms which can be detected by an increase in levels as detected by these methods. The inventors may assess the effect of NOEY2 on expression of these proteins by western blotting or by immunoprecipitation followed by western blotting where protein levels are low.

Sequence analysis of NOEY2 predicts that NOEY2 may have constitutively high GTP/GDP ratios. As NOEY2 contains a CAAX Box, the inventors predict that NOEY2 may be primarily a membrane associated protein. The inventors have demonstrated that NOEY2 inhibits the growth of ovarian cancer cells which contain activated or mutant Ras. The inventors predict that NOEY2 may function similar to Rap family members and may inhibit activation of the Ras by tyrosine kinase, and G protein linked receptors. The inventors predict that NOEY2 may inhibit MAPK activation induced by tyrosine kinase and G protein linked receptors and by activated Ras. By analogy, the inventors predict that NOEY2 may not inhibit activation of the Ras pathway by activated RAF or MEK. The inventors predict that NOEY2 may function at the G1 phase of the cell cycle. The inventors expect that NOEY2 may block cell cycle progression in G1 by inhibiting the pathway leading to RB phosphorylation. Without further data, it is impossible to predict at which level in the CDI/CDK/Cyclin RB cascade that be regulated by NOEY2.

5.6 Example 6

Genomic Sequence of NOEY2 (SEQ ID NO:5)

FIG. 7 shows the genomic structure of the NOEY2 locus. The genomic sequence of this region appears below:

```
NAGAANAGGGTCCAAGGNGTGGGAGAATAGNTTGTGTANACATTGNAGGA
AGACNGAAGATACAGGCAGAACATCNGTCAATAGAGGGNAGGGANAACAT
GGGTTTGACCNGGAAAGCCGGTACATTTNGGAGGAGGAGGGGTNTGGCCA
GTGGTGGCAGGAGGGAGGTTGTGGAAGCCAGGGTTCTTGTTACATATGNG
AAGCCTGTAATATGCTTCAGAAAGAATAGANGGCATATGTACCTCAAAAG
GTAAATGACCTTAAACGGTGTCAGACTNTNAGTTAAATCTCTCCCGGATC
AGAGAAAGACCTGGAAAGGGAAGGAGATTGTCCACAGAACACAAATTTCC
CTCGCAAAAGATAGCATTGCACAGGACCATTCCAAAATATGTCAGAAATA
TATTNTGGGGTAAAATACTTTGATCGCCCTTAGGGCTGNTACCTGTCATG
TGATGCTATACCAGAATCAGGTTGGAATTTGTTTTGAGACAGGTTCTCAC
TTTGTTGCTCAGATTGGAGTACAGTGGCAGTGATCACGGCTCACTGCAGC
CTCGATCTCCTTGATGTGGGAGGCTCAAGTGATCNTCCCACATCAGCCTC
CCAAATAGCTGGGACTACAGGCGGCCACCACCACACTGGGCGATATTNTT
TAAAAGTAGAGACAAGTTCTCCCCATGTTGCCCAGGCTGGTNTNTAACTC
NTGGCCTCAACCTCCTTATTTTNTAGGATTACAGGCGCCAGGNTAGACCT
CACAGGTCTTTAGACTTTTACGCACCAGGTACCTGGTAGGGGAGGGATT
ATAGTGGCAGAAGAGCAGTACCAGTGGCCCACACCACACACCCTGGCNTC
AGCTGGCTGGGCACACAAAACCAGGTGCTACCGTCAACGACTAGGCCCA
TAGGGTACTGCTGTCAAAACCTGCTGCCAACAANTTCCACACACTCCCCA
AAACGCTCGGTAGGCGGTGGTGCGCAGCTTTCAATGCATCCGCCGCCAGG
CGCTCACAGGCAAGGGAGAAAGAAGCCAGACGGAGCTCGGAGATGTGGAG
GGCAGACGCAGGCGCATTTGGAAAAGGGACTGGCGGTGGGAGGCGCAGAG
GGAAAAAGGAACGACACAATCGGGCTTCNTAGCCGCTGGCGGACCCGATG
GGGCGTCCTGCGAGGGTTCGGCGAGGGTTCTGCCAGGATAGTAGCATTGC
GCCCAAGGAGTGAGAGGCACCCGGGGNTACTGGAGCCAGACCCTCAACCC
GCCCTAGTGGGAGGCGAAGAACAACGAAAGCCTCGTATTCCCATTTCTNT
AATGGCTAATGACATTAAAGGTTTTCATATGGTTATTTGCCATCTGCATA
TCTTCAGTGAAATGTCTGTTTATGTCTTCTGACTATTCTCTAATTGGATT
TTTAAAAATAATTGGTTTTTGAGTTATTTACATATTCTAGATACTGGTTG
TATGCCAGATATATGGCTTGTAAATATTTTCTCCTAGGTAAACCTTTTCA
GTATCGTTACAGGGTCTTTCACAAAGCAAAAGTTTTAAATTTATGGAGTC
TAATTCATCAACATTTCTTTTTACCGGTCTTGCCACTAATGTCAATTTAA
GAACCTTTTGCCTAGCCTTAGACAATAGTTTGTTGTTTTTAAAACCGTT
TTGTAATTTTACTCGTCACAGTTATATCTAGCCATTAATTTTTATGTAAG
GGTTATTTTTGGCGGGGGGAATNTATAGATGTCCTGTCTTTTCAGTATC
ATTTGTGGAAAAGATTATNTGTCCTGCATTAAANTGCTTTTGGACTTTNG
```

```
TCTAAAATCAGTTGGACCGGTTTTTGTTGGCAAAGTTTTGCCTGAAGCTT
ATTCCAACAGGTGAGAAAAAGTCCACAGTTTAACAGTTCNTCCCCAACCT
GTAACCCCGCCTTGAACTTTTGGAATAGCCCCTCGATTGTTGTAGATGCC
AAGCGGACCTCGCGCCGCTNTGCGTTGGGCCAGCCCCTCACAGCTGGTTT
NTTACCANGTATTGCGCAAGCGGAATTTATGCNTGTTACCCACACTCCNT
GCGCCCCCGCACCCCGNTCCTGTGCGCAAGTCGGAATATAAAACCGCGGA
GGAGTGAGCTCTTGGGGTGTCCAGTTGGTTGCCGCGGCAGTCTCTCCGAG
CAGCGCATTTGTCTTCTAGGCTGCTTGGTTCGTGCCTCCGAGAAAGGTAA
GTCTTTCTTTCGCTTTTTTAGGGGTACTTGAAAACAACAAGTGTCAGACA
AAGCAGCAGATGCTGTTGCGCAGTANAAGTTTATGGGCGAGTTGTCCCTG
AAACTGGAACCAGGTCTTTCTTGGCGCGATTACGCAAGAACCACCCGCAG
CCCTGCGGGCTCCTGGCAGGTCCTGCAACTGCACTTTGGATAGTCCCGTT
GGGAAGCTAGCACTTTTTAATATAAAAGAACGAGGTTTGATAAGTGTGCG
AGCTTAAAGGTTGACACAGTGTCCACTATTACAGCTGCGTANGTAGCTAG
TGTTCAGGAAGTAATAGTGGAGTCATGTAGTGTGAAAGTAAGATTGAAAT
GGGCGAGGAGGGTAGCAGCCGCCACAGCCACCAGAGAGAAACCTGACCTT
GCAGGTGCGTGGTGATGTCCATGAGCCAGGCTGGTGCCGCAACAGCAGCG
GCGGGACCTTGAGCTCCGCACGGCCGCTGGGTTTGGACGCCCTCTGGTTC
CTGGAAACTTTCACCTCCCCCTCAGCCTGAGGCCAGGTGGCCTGGGAAGG
TGGAACGAGTGTGGAGGGGAGTGGGGGGGGGGTCCACTGCCTGANAATG
ANAATTCTCTTCACATCTGGAAATTCAGTTATCACGTGTGTCCTTTACCA
ATTTTTTTCTTTTATTTTCTTTTTGATAGAGACGGCGGTCTCCCTATGT
TACCCAGGCTAGTCTTGAACTCCTGTGCTTAAGCGATCCTCCCACCTTGA
CTTCCCAAAGTGCTGGAATTACAGGCATGAGCCAATGCGCCCGGCTGCTT
TACCAATTTTCTATGAATGAATTTGTACATACATCCCCTAGANCAGGAAG
TNATGTANAACAGAATAATTAGTAATGCACATTTCCTAATGTGGGATGTT
GGTGGCCACAGATATTTGGTCTTTACTGGAACTCTTGATACTAACATGG
NAGTTTATAATAGTTGTGGAGAGTGCAGACAAGGCTAGGATTTCTGTGAC
TAGAGAACTCTTAGTGCGTGAAGACCTAAGGAAAGCTGGATTGTTGATTT
TTGTTAATAAATAAGATGTGAAAGATTGCATCACTGTAGCAGAAATCTCC
TAGTTTTTTAAGCTAAATTCTATTAAAGGTCATCATTGCTAAAGGAATTG
TGCCCAGGATTTGGATAGCTGATGTCATTACTTAATATTAGATGATATCA
ACTAACCACATCTCATAGACTGGAATAAAGTGCTAGATTTTACCTGAAAG
CTGCAAAAATGAATGGTTTAGATATATGTATGTATTTATTTTATATCAAT
TTCAAATATTTACTGTATTAACCTCCCTGGCCCCCTTTAATCAAGAATAT
AAAATCATCTACTTAAATTTTGCCACTTAAGTTTAGAACACTCTTAGAAT
CACACTATCTTAAAGAAGCCAGACTAGAATTAGAAGCAANTTAANTCTGA
AGATATAACAACCAGCAACAACATTTTTTTTTTCAAATGAAAACTCTAA
TATGGGGTGGGTATGTTGTGTCACACCTGTAATCCCAACACTTTGGGAGG
CTGATGCAGGAGGATCACTTGAACACAGGAGTTCAAGACCANCCTGGACA
```

-continued

```
ACATAGCAAAACCCTGTCCCTACAAAAAATAANAAAATTAGCTGGGCATG
GTGTCACATGCCTGTAGTCCCAGCTACTCGGGAGGCTGAGGTGANAGGAT
TGATTGATCCCAGGAGGTTGAGGCTGCAGTGAGTCATGATCGCATGACTG
CACTCCAACCTGAGGGACANAGCAAGACCCTGACTCAAAAAAAAAAAACA
AAAAAAAAAAAACCACCACCAAAACTCTAATATGGACATATTACTCTCTC
ATGGGACTTGCACATTCTAAAAAGGGTCCTTTTCCCCAGTACTGGGANAN
TATNTGTTCAACTACGCAGCCAGCAANACAGGCTATTTTATATAGGGAGT
GTGCTATTCACAAAAAGCCTCTCTTCTCTTTCTGGTATTGTACATGACAC
AATCATAGCTGTACCTGAAAAAAANTGCATTTTAAGGACCATCATCACCT
AAAAACATGTNTAAATTTCTATACCTAGTGCCACAGGAATNACATTGCCT
TGTACTATTCCTACCTCTGTCCAAAGGCCAGCTATGTGGTCTGTCTGCAT
GGTGCCTAAAACTTTTTCCATCTGACCTAGGATGCTTCTGAAGCAGTCCC
CCTGGGCAGCTGTCTGGTATTTAGGATATACCTGTGAGAAAANTTNCTTA
CAACCCTAATCTACTATGTTTATTCCTGAACTCAAAAANTTCATTTGACT
GTTCAATTCCTGAAATTTNCTCTATTTCCANAAGGCTGAATTAAAATTAC
TTTGTTAAAGGTANTAGCCATGGCAAAAAAAAAACCACTGTTCTGTAAAA
AAACTCATTCAATATTTACAATCTTTTCTAATCAAAAATTANATCCTGAA
AAGAAAGGTTCATATATATATATATATATATATATATATATATATATATA
TATATATATATATCTTTTTTTTTTTTTTTTTTTTTTTTTACTC
CACTGTCATTGTGACTAAGGATTCATGAACTAAGACCCCTCCCTCAGCTT
TTGGTGGCACATGGTGACAGCATGCTCAGAGCAAAGGTGCTCCCCATGCC
TNTTCTGGGGNTGCACTGACTGCAGGTACCTCCCCTTTTTACATCCCACA
CCAGTGAATCCAAAAACCCCCTCCTTTCTCCTGTANTGATGACTCTGTAG
CTTTAACCAGGGNGACGGTGTCACTNTAAATGTCACCTTGGCATTCAGCC
CCATAGAGTGGGAAAATTCCCTCACCTGTTTCTCTTTGACTGTTCAGTC
CACTTCAATTAAAATCTTAATTTTACAAGCGAGGAAATGAGAGTGTTTCT
TGTAGGGTGTAGTGAGAATTTAATAAAACAGTTTAAGGAAAGAAAACAA
AAGGTAGTATTGCTGCACTTTNTAGATGGTAAAAAGCAAACCACCATGTC
TGTTTAATATATATCACCTGCTGGTCCNTCGGTCTAGCAGGCTGAACTGT
GTGCCTGGGAATTTTTTTCTCGCTGTGTGCACCCCTTTACGTCACAGGGT
GGATCTCTTCAGAGTCCATGNGGAGCAGCTGGCCAGGCTGACATGATCTG
ACAAGATTGTAGGTTACCANTACCATCTCTCACCGTCTCACTTTCTTCCT
AGGGGTCTCCTGCTGCCAGCTAAGTGTGGGAGAACTTGTGCACGTATCTC
CCCTCCGAATCCCAACGATGGGTAACGCCAGCTTTGGCTCCAAGGAACAG
AAGCTGCTGAAGCGGTTGCGGCTTCTGCCCGCCCTGCTTATCCTCCGCGC
CTTCAAGCCCCACAGGAAGATCAGAGATTACCGCGTCGTGGTAGTCGGCA
CCGCTGGTGTGGGAAAAGTACGCTGCTGCACAAGTGGGCGAGCGGCAAC
TTCCGTCATGAGTACCTGCCGACCATTGAAAATACCTACTGCCAGTTGCT
GGGCTGCAGCCACGGTGTGCTTTCCCTGCACATCACCGACAGCAAGAGTG
GCGACGGCAACCGCGCTCTGCAGCGCCACGTTATAGCCCGGGGCCACGCC
TTCGTCCTGGTCTACTCAGTCACCAAGAAGGAAACCCTGGAAGAGCTGAA
GGCCTTCTATGAGCTGATCTGCAAGATCAAAGGTAACAACCTGCATAAGT
TCCCCATCGTGCTGGTGGGCAATAAAAGTGATGACACCCACCGGGAGGTG
GCCCTGAATGATGGTGCCACCTGTGCGATGGAGTGGAATTGCGCCTTCAT
GGAGATTTCAGCCAAGACCGATGTGAATGTGCAGGAGCTGTTCCACATGC
TGCTGAATTACAAGAAAAAGCCCACCACCGGCCTCCAGGAGCCCGAGAAG
AAATCCCAGATGCCCAACACCACTGAGAAGCTGCTTGACAAGTGCATAAT
CATGTGAGCCCTGGGCCTTAAGAGCCAGCTCTTCCTATCCTGTAGCGTGT
AGAAAACGTGGACTCATTTCACTATGTTACATGTACATGGTTGATTTTGT
GCTGTTGTTTGGACTGTAACATCCATGTTGTCAATACGTATACCTTGTAA
GTGGATAACTTTTCTTTTTCCCAGGCCAGAGAATTCAAATTGTTAAAACA
TTGGCATTTGAAGAGGAGAACAAAATGTAGCATGATGTATTTAAAGTAAG
GCCTTTAGTAATGAATGTAATGAGAGAAAATGTTTTGAAAAGAACAAAAC
ATCAAAATGAATAGAAAGAAAAATTGGAAGGCGTCCTTTTGGTAACCCGA
TTATTGTGTATTACCTTTAAATATTTCACATCCTGTAAGTGCTTAATCAT
ATCTTTTAATTGTGTATTTAAGAAAAGTGTTTTCACAACAAAAGCTTTTG
ATAAATTGCTGCGTGACATATACTAAATAAAAAAATGAATATGTTGATCA
TTAGGGGTGTGGGAGCAGAGAAAATTGTGAAAGTGACTCTCACTAAAGAT
GTTAGTAGTTTCTCATGTCATTTAAAAATGTTTGAGTATTCTGCATAGCA
GTTTGTAAAAGTGTAACAGCTTATTGACTTAATAAAGCTTTTCCTGCATG
CAATCAGCTGTAANAATTTGTCTCACCANAAAACAAAACATTGCCCATTG
TATTAAAATTTAAACCATATCTGTTAAAAGTTTCCAATAAGAACTTCACA
CATGGATGTCCTTGCCATGTTGAAATTATCCAATATGGGAGGGGGTGTT
TTAGGGAGGTCTCTGCAATACANAGCTGTTTTGTGTCTTTCCTGAACTGA
CATCCCGAAAAACTCCAGGCATCTTTGAGGAAAATGGTCACAGTGTTGCT
GTCTCANAGGAAGCGGGTGAAAAGCAAGCCTCTGCCTTCTGCCTCTTCCT
ATATTCTGAAATACTGGATATAGGCAATAGGGAGCAGAATGAAAGACAAG
GGGAGGAATGATATTTGAGANACTCCCCCATAAGGGAGTTTTTAAAGAGA
TTATATTTGAACATAATTTTTTGAGCGAGGGAATAAAGTATACATATCCT
TGCTTTTGANAGTTTTTTTTTTTTTTTAAATTGGGAAANGTTCAGGGGA
GGCNCTAATCTANTGATTTTTTTCCCCCCNAAATNTTATTGAACNAATA
TCTATTGAACAATNTTNTNTNTTTCTACACAAAAANCACATTGTTCC
```

6.0 REFERENCES

The following references, to the extent that they provide exemplary procedural or other details supplementary to those set forth herein, are specifically incorporated herein by reference.

U.S. Pat. No. 4,196,265, issued Apr. 1, 1980.
U.S. Pat. No. 4,237,224, issued Dec. 2, 1980.
U.S. Pat. No. 4,329,332, issued May 11, 1982.
U.S. Pat. No. 4,489,055, issued Dec. 18, 1984.
U.S. Pat. No. 4,554,101, issued Nov. 19, 1985.
U.S. Pat. No. 4,683,195, issued Jul. 28, 1987.
U.S. Pat. No. 4,683,202, issued Jul. 28, 1987.

U.S. Pat. No. 4,800,159, issued Jan. 24, 1989.
U.S. Pat. No. 4,800,159, issued Jan. 24, 1989.
U.S. Pat. No. 4,873,191, issued Oct. 10, 1989.
U.S. Pat. No. 4,883,750, issued Nov. 28, 1989.
U.S. Pat. No. 4,913,908, issued Apr. 3, 1990.
U.S. Pat. No. 4,965,188, issued Oct. 23, 1990.
U.S. Pat. No. 4,987,071, issued Jan. 22, 1991.
U.S. Pat. No. 5,176,995, issued Jan. 5, 1993.
U.S. Pat. No. 5,225,341, issued Jul. 6, 1993.
U.S. Pat. No. 5,276,269, issued Jan. 4, 1994.
U.S. Pat. No. 5,279,721, issued Jan. 18, 1994.
U.S. Pat. No. 5,334,711, issued Aug. 2, 1994.
U.S. Pat. No. 5,354,855, issued Oct. 11, 1994.
U.S. Pat. No. 5,384,253, issued Jan. 24, 1995.
U.S. Pat. No. 5,451,410, issued Sep. 19, 1995.
U.S. Pat. No. 5,482,852, issued Jan. 9, 1996.
U.S. Pat. No. 5,500,224, issued Mar. 19, 1996.
U.S. Pat. No. 5,508,468, issued Apr. 16, 1996.
U.S. Pat. No. 5,550,318, issued Aug. 27, 1996.
U.S. Pat. No. 5,556,617, issued Sep. 17, 1996.
U.S. Pat. No. 5,620,708, issued Apr. 15, 1997.
U.S. Pat. No. 5,631,359, issued May 20, 1997.
U.S. Pat. No. 5,641,515, issued Jun. 24, 1997.
U.S. Pat. No. 5,698,515, issued Dec. 16, 1997.
Int. Pat. Appl. Publ. No. PCT/US87/00880.
Int. Pat. Appl. Publ. No. PCT/US89/01025.
Int. Pat. Appl. Publ. No. WO 84/03564.
Int. Pat. Appl. Publ. No. WO 88/10315.
Int. Pat. Appl. Publ. No. WO 88/10315.
Int. Pat. Appl. Publ. No. WO 89/06700.
Int. Pat. Appl. Publ. No. WO 89/06700.
Int. Pat. Appl. Publ. No. WO 91/03162.
Int. Pat. Appl. Publ. No. WO 92/07065.
Int. Pat. Appl. Publ. No. WO 93/15187.
Int. Pat. Appl. Publ. No. WO 93/23569.
Int. Pat. Appl. Publ. No. WO 94/02595.
Int. Pat. Appl. Publ. No. WO 94/13688.
Eur. Pat. Appl. Publ. No. EP 0273085.
Eur. Pat. Appl. Publ. No. EP 0360257.
Eur. Pat. Appl. Publ. No. EP 92110298.4.
Eur. Pat. Appl. Publ. No. EP 320,308.
Eur. Pat. Appl. Publ. No. EP 329,822.
Great Britain Pat. Appl. Publ. No. GB 2,202,328.
"Manipulating the Mouse Embryo: A Laboratory Manual," 2nd edition (eds., Hogan, Beddington, Costantimi and Long, Cold Spring Harbor Laboratory Press, 1994.
"Modern Applied Statistics With S-Plus," Venables W N, Ripley, B D Springer-Verlag. New York, 1994.
"Remington's Pharmaceutical Sciences," 15th ed., pp. 1035–1038 and 1570–1580.
Albanese et al., "Transforming $p21^{ras}$ mutants and c-Ets-2 activate the cyclin D1 promoter through distinguishable regions," *J. Biol. Chem.*, 270:23589–23597, 1995.
Arshady, "In vivo targeting of colloidal carriers by novel graft copolymers," *J. Mol. Recognit.*, 9(5–6):536–542, 1996.
Baichwal and Sugden, "Vectors for gene transfer derived from animal DNA viruses: Transient and stable expression of transferred genes," In: *Gene transfer*, Kucherlapati R, ed., New York: Plenum Press, pp. 117–148, 1986.
Barany and Merrifield, "A chromatographic method for the quantitative analysis of the deprotection of dithiasuccinoyl (Dts) amino acids," *Ana. Biochem.*, 95(1):160–170, 1979.
Baselga and Mendelsohn, "Receptor blockade with monoclonal antibodies as anti-cancer therapy," *Pharmacology & Therapeutics*, 64(1):127–54, 1994.

Baselga, Norton, Masui, Pandiella, Coplan, Miller, Mendelsohn, "Antitumor effects of doxorubicin in combination with anti-epidermal growth factor receptor monoclonal antibodies," *J. Nat. Cancer Inst.*, 85(16):1327–33, 1993.
Bast, Feeney, Lazarus, Nadler, Colvin, Knapp, "Reactivity of a monoclonal antibody with human ovarian carcinoma," *J. Clin. Invest.*, 68:1331–1337, 1981.
Bast, Jacobs, Berchuck, "Editorial: Malignant transformation of ovarian epithelium," *J. Natl. Cancer Inst.*, 84:556–558, 1992.
Bast, Klug, St. John, Jenison, Niloff, Lazarus, Berkowitz, Leavitt, Griffiths, Parker, Zurawski, Knapp, "A radioimmunoassay using a monoclonal antibody to monitor the course of epithelial ovarian cancer," *New Engl. J. Med.*, 309:883–887, 1983.
Benvenisty and Neshif, "Direction introduction of genes into rats and expression of the genes," *Proc. Nat. Acad. Sci. USA*, 83:9551–9555, 1986.
Berchuck, Kamel, Whitaker, Kems, Olt, Kinney, Soper, Dodge, Clarke-Pearson, Marks, McKenzie, Yin, Bast, "Overexpression of HER-2/neu is associated with poor survival in advanced epithelial ovarian cancer," *Cancer Res.*, 50:4087–4091, 1990.
Berchuck, Kohler, Marks, Wiseman, Boyd, Bast, "The p53 tumor suppressor gene frequently is altered in gynecologic cancers," *Am. J. Obstet. Gynecol.*, 170:246–252, 1994.
Berchuck, Rodriguez, Kamel, Dodge, Soper, Clarke-Pearson, Bast, "Epidermal growth factor receptor expression in normal ovarian epithelium and ovarian cancer. I. Correlation of receptor expression with prognostic factors in patients with ovarian cancer," *Am. J. Obstet. Gynecol.*, 164:669–674, 1991.
Berchuck, Rodriguez, Olt, Whitaker, Boente, Arrick, Clarke-Pearson, Bast, "Regulation of growth of normal ovarian epithelial cells and ovarian cancer cell lines by transforming growth factor-β," *Am. J. Obstet. Gynecol.*, 166:676–684, 1992.
Berenbaum, "Synergy, additivism and antagonism in immunosuppression. A critical review," *Clin. Exp. Immunol.*, 28:1–18, 1977.
Bourne, Sanders, McCormick, "The GTPase superfamily: conserved structure and molecular mechanism," *Nature*, 349:117–127, 1991.
Brinster et al., "Factors affecting the efficiency of introducing foreign DNA into mice by microinjecting eggs," *Proc. Natl. Acad. Sci. USA*, 82(13):4438–4442, 1985.
Brown, "Some properties of the Spearmann estimator in bioassay," *Biometrika*, 48:293–302, 1961.
Brown-Shiner, Johnson, Hill, Bruskin, "Effect of protein tyrosine phosphatase 1B expression on transformation by the human neu oncogene," *Cancer Res.*, 52:478–482, 1992.
Calvo, Vila-Jato, Alonso, "Effect of lysozyme on the stability of polyester nanocapsules and nanoparticles: stabilization approaches," *Biomaterials*, 18(19):1305–1310, 1997.
Calvo, Vila-Jato, Alonso, "Improved ocular bioavailability of indomethacin by novel ocular drug carriers," *J. Pharm. Pharmacol.*, 48(11):1147–1152, 1996.
Campa, Cnang, Vedia, Reep, Lapetina, "Inhibition of Ras-induced germinal vesicle breakdown in *Xenopus* oocytes by Rap-1B," *Biochem. Biophys. Res. Commun.*, 174:1–5, 1991.

Campbell, "Monoclonal Antibody Technology, Laboratory Techniques in Biochemistry and Molecular Biology," Vol. 13, Burden and Von Knippenberg, Eds. pp. 75–83, Elsevier, Amsterdam, 1984.

Capaldi et al., "Changes in order of migration of polypeptides in complex III and cytochrome C oxidase under different conditions of SDS polyacrylamide gel electrophoresis," Biochem. Biophys. Res. Commun., 74(2):425–433, 1977.

Capaldi et al., "Isolation of a major hydrophobic protein of the mitrochondrial inner membrane," Biochem. Biophys. Res. Commun., 55(3):655–659,1973.

Capaldi, "Identification of the major enzymic activities of the mitochondrial inner membrane in terms of their migration in sodium dodecyl sulfate polyacrylamide gel electrophoresis," Aech. Biochem. Biophys., 163(1):99–105, 1974.

Cech et al., "In vitro splicing of the ribosomal RNA precursor of Tetrahymena: involvement of a guanosine nucleotide in the excision of the intervening sequence," Cell, 27(3 Pt 2):487–496, 1981.

Chang et al., "Foreign gene delivery and expression in hepatocytes using a hepatitis B virus vector," Hepatology, 14:124A, 1991.

Chen and Okayama, "High-efficiency transfection of mammalian cells by plasmid DNA," Mol. Cell Biol., 7:2745–2752, 1987.

Chen et al., Nucl. Acids Res., 20:4581–4589, 1992.

Chowrira and Burke, Nucl. Acids Res., 20:2835–2840, 1992.

Clayman, Liu, Overholt, Mobley, Wang, Janot, Goepfert, "Gene therapy for head and neck cancer: comparing the tumor suppressor gene p53 and a cell cycle regulator WAF1/CIP1 (p21)," Arch. Otolaryngol., 122(5):489–93, 1996.

Coffin, "Retroviridae and their replication," In: Virology, Fields B N, Knipe D M, ed., New York: Raven Press, pp. 1437–1500, 1990.

Collins and Olive, "Reaction conditions and kinetics of self-cleavage of a ribozyme derived from Neurospora VS RNA," Biochem., 32(11):2795–2799, 1993.

Cook, Rubinfield, Albert, McCormick, "RapV12 antagonizes Ras-dependent activation of ERK1 and ERK2 by LPA and EGF in Rat-1 fibroblasts," EMBO J., 12:3475–3485, 1993.

Couch et al., "Immunization with types 4 and 7 adenovirus by selective infection of the intestinal tract," Am. Rev. Resp. Dis., 88:394–403, 1963.

Coupar et al., "A general method for the construction of recombinant vaccinia virus expressing multiple foreign genes," Gene, Vol 68:1–10, 1988.

Cox, "Regression Models and Life Tables" J. Royal Statistical Society, B, 34:187–220, 1972.

Culver et al., "In vivo gene transfer with retroviral vector-producer cells for treatment of experimental brain tumors," Science, 256:1550–1552, 1992.

Cusack, Spitz, Nguyen, Zhang, Cristiano, Roth, "High levels of gene transduction in human lung tumors following intralesional injection of recombinant adenovirus," Cancer Gene Therapy, 3(4):245–249, 1996.

Damge, Vonderscher, Marback, Pinget, "Poly(alkyl cyanoacrylate) nanocapsules as a delivery system in the rate for octreotide, a long-acting somatostatin analogue," J. Pharm. Pharmacol., 49(10):949–954, 1997.

Dorsch, Hock, Kunzendorf, Diamantstein, Blankenstein, "Macrophage colony-stimulating factor gene transfer into tumor cells induces macrophage infiltration but not tumor suppression," Eur. J. Immunol., 23(1):186–90, 1993.

Dropulic, Lin, Martin, Jeang, "Functional characterization of a U5 ribozyme: intracellular suppression of human immunodeficiency virus type 1 expression," J. Virol., 66(3):1432–41, 1992.

Dubensky et al., "Direct transfection of viral and plasmid DNA into the liver or spleen of mice," Proc. Nat. Acad. Sci. USA, 81:7529–7533, 1984.

Egli, Usman, Rich, "Conformational influence of the ribose 2'-hydroxyl group: crystal structures of DNA-RNA chimeric duplexes," Biochem., 32(13):3221–3237, 1993.

El-Deiry et al., "WAF1, a potential mediator of p53 tumor suppression," Cell, 75:817–825, 1993.

Elroy-Stein and Moss, "Cytoplasmic expression system based on constitutive synthesis of bacteriophage T7 RNA polymerase in mammalian cells," Proc. Natl. Acad. Sci. USA, 87:6743–7, 1990.

Fan, Baselga, Masui, Mendelsohn, "Antitumor effect of anti-epidermal growth factor receptor monoclonal antibodies plus cis-diamminedichloroplatinum on well established A431 cell xenografts," Cancer Res., 53(19):4637–42, 1993.

Fechheimer et al., "Transfection of mammalian cells with plasmid DNA by scrape loading and sonication loading," Proc. Natl. Acad. Sci. USA, 84:8463–8467, 1987.

Feig, Bast, Knapp, Cooper, "Somatic activation of RasK gene in a human ovarian carcinoma," Science, 223:698–700, 1984.

Ferkol, Lindberg, Chen, Perales, Crawford, Ratnoff, Hanson, "Regulation of the phosphoenolpyruvate carboxykinase/human factor IX gene introduced into the livers of adult rats by receptor-mediated gene transfer," FASEB J., 7(11):1081–1091, 1993.

Ferrari, Fomasiero, Isetta, "MTT colorimetric assay for testing macrophage cytotoxic activity in vitro," J. Immunol. Methods, 131:165–172, 1990.

Finney, "Statistical Methods in Biologic assays," Third Edition. New York Macmillan, 374–401, 1978.

Fodor et al., "Light-directed, spatially addressable parallel chemical synthesis," Science, 251(4995):767–773, 1991.

Forster and Symons, "Self-cleavage of plus and minus RNAs of a virusoid and a structural model for the active sites," Cell, 49:211–220, 1987.

Fraley et al., "Entrapment of a bacterial plasmid in phospholipid vesicles: Potential for gene transfer," Proc. Natl. Acad. Sci. USA, 76:3348–3352, 1979.

Frankel and Mills, "Peptide and lipid growth factors decrease cisplatin-induced cell death in human ovarian cancer cells," Clin. Cancer Res., 2:1307–1313, 1996.

Freifelder et al., "Dialysis of small samples in agarose gels," Anal. Biochem., 123(1):83–85, 1982.

Freifelder et al., "Studies on Escherichia coli sex factors. I. Specific labeling of F'Lac DNA," J. Mol. Biol., 32(1):15–23, 1968a.

Freifelder et al., "Studies on Escherichia coli sex factors. II. Some physical properties of F'Lac and F DNA," J. Mol. Biol., 32(1):15–23, 1968b.

Freshner, "Animal Cell Culture: a Practical Approach", Second Edition, Oxford/New York, IRL Press, Oxford University Press, 1992.

Friedmann, "Progress toward human gene therapy," Science, 244:1275–1281, 1989.

Frohman, In: PCR™ Protocols: A Guide to Methods and Applications, Academic Press, New York, 1990.

Frommer, McDonald, Millar, Collis, Watt, Grigg, Molloy, Paul, "A genomic sequencing protocol that yields a positive display of 5-methylcytosine residues in individual DNA strands," *Proc. Natl. Acad. Sci. USA*, 89(5):1827–1831, 1992.

Gao and Huang, "Cytoplasmic expression of a reporter gene by co-delivery of T7 RNA polymerase and T7 promoter sequence with cationic liposomes," *Nuc. Acids Res.*, 21:2867–2872, 1993.

Gefter et al., *Somatic Cell Genet.* 3:231–236, 1977.

Gerlach et al., "Construction of a plant disease resistance gene from the satellite RNA of tobacco rinspot virus," *Nature* (London), 328:802–805, 1987.

Ghosh and Bachhawat, "Targeting of liposomes to hepatocytes," In: *Liver diseases, targeted diagnosis and therapy using specific receptors and ligands*, Wu G, Wu C ed., New York: Marcel Dekker, pp. 87–104, 1991.

Ghosh-Choudhury, Haj-Ahmad, Graham, "Protein IX, a minor component of the human adenovirus capsid, is essential for the packaging of full-length genomes," *EMBO J.*, 6:1733–1739, 1987.

Gibson, Leung, Squire, Hill, Arima, Goss, Hogg, Mills, "Identification, cloning and characterization of a novel human T cell specific tyrosine kinase located at the hematopoietin complex on chromosome 5q," *Blood*, 82:1561–1572, 1993.

Gill, Hamel, Zhe, Zachsenhaus, Gallie, Phillips, "Characterization of the human RB1 promoter and of elements involved in transcriptional regulation," *Cell Growth and Differentiation*, 5(5):467–474, 1994.

Goding, "Monoclonal Antibodies: Principles and Practice," pp. 60–74. 2nd Edition, Academic Press, Orlando, Fla., 1986.

Gomez-Foix, Coats, Baque, Alam, Gerard, Newgard, "Adenovirus-mediated transfer of the muscle glycogen phosphorylase gene into hepatocytes confers altered regulation of glycogen," *J. Biol. Chem.* 267:25129–25134, 1992.

Gopal, "Gene transfer method for transient gene expression, stable transfection, and cotransfection of suspension cell cultures," *Mol. Cell Biol.*, 5:1188–1190, 1985.

Gossen and Bujard, "Tight control of gene expression in mammalian cells by tetracycline responsive promoters," *Proc. Natl. Acad. Sci. USA*, 89:5547–5551, 1992.

Graff, Herman, Lapidus, Chopra, Xu, Jarrard, Isaacs, Pitha, Davidson, Baylin, "E-cadherin expression is silenced by DNA hypermethylation in human breast and prostate carcinomas," *Cancer Res.*, 55(22):5195–5199, 1995.

Graham and Prevec, "Adenovirus-based expression vectors and recombinant vaccines," *Biotechnology*, 20:363–390, 1992.

Graham and Prevec, "Manipulation of adenovirus vector," In: *Methods in Molecular Biology: Gene Transfer and Expression Protocol*, E. J. Murray (ed.), Clifton, N.J.: Humana Press, 7:109–128, 1991.

Graham et al., "Characteristics of a human cell line transformed by DNA from human adenovirus type 5", *J. Gen. Virol.*, 36:59–72, 1977.

Graham and van der Eb, "Transformation of rat cells by DNA of human adenovirus 5," *Virology*, 54(2):536–539, 1973.

Grambsch and Therneau, "Proportional Hazards Tests and Diagnostics Based On Weighted Residuals," *Biometrika*, 81:5515–5526, 1994.

Grunhaus and Horwitz, "Adenovirus as cloning vector," *Seminar in Virology*, 3:237–252, 1992.

Guerrier-Takada, Gardiner, Marsh, pace, Altman, "The RNA moiety of ribonuclease P is the catalytic subunit of the enzyme," *Cell*, 35:849, 1983.

Gum, Lengyel, Juarez, Chen, Sato, Seiki, Boyd, "Stimulation of 92-kDa gelatinase B promoter activity by ras is mitogen-activated protein kinase 1-independent and requires multiple transcription factor binding sites including closely spaced PEA3/ets and AP-1 sequences," *J. Biol. Chem.*, 271(18):10672–10680, 1996.

Hagopian, Mills, Khokhar, Bast, Siddik, "Studies of cisplatin (CDDP) resistance with 1R,2R-diaminocyclohexane (DACH)-diacetato-dichloro-Pt(IV) (acetato-Pt) in ovarian cancer cell lines," *Proc. Amer. Assoc. Cancer Res.*, 37:402(A#1399), 1996.

Hampel and Tritz, "RNA catalytic properties of the minimum (-)s TRSV sequence," *Biochem.*, 28:4929, 1989.

Hampel, Tritz, Hicks, Cruz, "'Hairpin' catalytic RNA model: evidence for helices and sequence requirement for substrate RNA," *Nuc. Acids Res.*, 18:299, 1990.

Harland and Weintraub, "Translation of mammalian mRNA injected into *Xenopus oocytes* is specifically inhibited by antisense RNA," *J. Cell Biol.*, 101:1094–1099, 1985.

Harlow and Lane, "Antibodies: A Laboratory Manual," Cold Spring Harbor Laboratory, Cold Spring Harbor, N.Y., 1988.

Harrington and Fleming, "Counting Processes and Survival Analysis," John Wiley and Sons, New York, 1991.

Hata, Kaibuchi, Kawamura, Hiroyoshi, Shirataki, Takai, "Enhancement of the actions of smg p21 GDP/GTP exchange protein by the protein kinase A-catalyzed phosphorylation of smg p21," *J. Biol. Chem.*, 166:6571–6577, 1991.

Havrilesky, Hurteau, Whitaker, Elbendary, Wu, Rodriguez, Bast, Berchuck, "Regulation of apoptosis in normal and malignant ovarian epithelial cells by transforming growth factor-$\beta$" *Cancer Res.*, 55:944–948, 1995.

Herman, Jen, Merlo, Baylin, "Hypermethylation-associated inactivation indicates a tumor suppressor role for p15INK4B," *Cancer Res.*, 56(4):722–727, 1996.

Herman, Latif, Weng, Lerman, Zbar, Liu, Samid, Duan, Gnarra, Linehan et al., "Silencing of the VHL tumor-suppressor gene by DNA methylation in renal carcinoma," *Proc. Natl. Acad. Sci. USA*, 91(21):9700–9704, 1994.

Hermonat and Muzycska, "Use of adenoassociated virus as a mammalian DNA cloning vector: Transduction of neomycin resistance into mammalian tissue culture cells," *Proc. Natl. Acad. Sci. USA*, 81:6466–6470, 1984.

Hersdorffer et al., "Efficient gene transfer in live mice using a unique retroviral packaging line," DNA Cell Biol., 9:713–723, 1990.

Hertel, Pardi, Uhlenbeck, Koizumi, Ohtsuka, Uesugi, Cedergren, Eckstein, Gerlach, Hodgson et al., "Numbering system for the hammerhead," *Nucl. Acids Res.*, 20(12):3252, 1992.

Herz and Gerard, "Adenovirus-mediated transfer of low density lipoprotein receptor gene acutely accelerates cholesterol clearance in normal mice," *Proc. Natl. Acad. Sci. USA*, 90:2812–2816, 1993.

Hilsenbeck, and Clark, "Practical p-Value Adjustment for Optimally Selected Cutpoints," *Statistics in Medicine*, 15:103–112, 1996.

Hoggard, Brintnell, Howell, Weissenbach, Varley, "Allelic imbalance on chromosome 1 in human breast cancer. II. Microsatellite repeat analysis," *Genes, Chromosomes Cancer*, 12:24–31, 1995.

Horwich et al., "Synthesis of hepadnavirus particles that contain replication-defective duck hepatitis B virus genomes in cultured HuH7 cells," *J. Virol.*, 64:642–650, 1990.

Hurteau, Rodriguez, Whitaker, Shah, Mills, Bast, Berchuck, "Transforming growth factor-β inhibits proliferation of human ovarian cancer cells obtained from ascites," *Cancer,* 74:93–99, 1994.

Innis et al., "DNA sequencing with *Thermus aquaticus* DNA polymerase and direct sequencing of polymerase chain reaction-amplified DNA," *Proc. Natl. Acad. Sci. USA,* 85(24):9436–9440, 1988.

Jacobs, Kohler, Wiseman, Marks, Whitaker, Kerns, Humphrey, Berchuck, Ponder, Bast, "Clonal origin of epithelial ovarian cancer: Analysis by loss of heterozygosity, p53 mutation and X chromosome inactivation," *J. Natl. Cancer Inst.,* 84:1793–1798, 1992.

Jacobs, Smith, Wiseman, Futreal, Harrington, Osborne, Leach, Molyneaux, Berchuck, Ponder, Bast, "A deletion unit on chromosome 17q in epithelial ovarian tumors distal to the familial breast/ovarian cancer locus," *Cancer Res.,* 53:1218–1221, 1993.

Jaeger, Turner, Zuker, "Improved predictions of secondary structures for RNA," *Proc. Natl. Acad. Sci. USA,* 86(20):7706–7710, 1989.

Jahnke, Van de Stolpe, Caldenhoven, Johnson, "Constitutive expression of human intercellular adhesion molecule-1 (ICAM-1) is regulated by differentially active enhancing and silencing elements, *Eur. J. Biochem,* 228(2):439–446, 1995.

Jameson and Wolf, "The antigenic index: a novel algorithm for predicting antigenic determinants," *Compu. Appl. Biosci.,* 4(1):181–186, 1988.

Jelinek and Hassell, "Reversion of middle T antigen-transformed Rat-2 cells by Krev-1: implications for the role of p21c-Ras in polyomavirus-mediated transformation," *Oncogene,* 7:1687–1698, 1992.

Jones and Shenk, "Isolation of deletion and substitution mutants of adenovirus type 5," *Cell,* 13:181–188, 1978.

Joyce, "RNA evolution and the origins of life," *Nature,* 338:217–244, 1989.

Kacinski, "CSF-1 and its receptor in ovarian, endometrial and breast cancer," *Ann. Med,* 27(1):79–85, 1995.

Kacinski, Mayer, King et al., "Neu protein overexpression in benign, borderline, and malignant ovarian neoplasms," *Gynecol. Oncol.,* 44:245–253, 1992.

Kaneda et al., "Increased expression of DNA cointroduced with nuclear protein in adult rat liver," *Science,* 243:375–378, 1989.

Karlan, Baldwin, Cirisano, Mamula, Jones, Lagasse, "Secreted ovarian stromal substance inhibits ovarian epithelial cell proliferation," *Gyn. Onc,* 59(1):67–74, 1995.

Kashani-Saber et al., *Antisense Res. Dev.,* 2:3–15, 1992.

Kato et al., "Expression of hepatitis B virus surface antigen in adult rat liver," *J. Biol. Chem.,* 266:3361–3364, 1991.

Kitayama, Sugimoto, Matsuzaki, Ikawa, Noda, "A Ras-related gene with transformation suppressor activity," *Cell,* 56:77–84, 1989.

Klein et al., *Proc. Natl. Acad. Sci. USA,* 85:8502–8505, 1988.

Klein, Wolf, Wu, Sanford, "High-velocity microprojectiles for delivering nucleic acids into living cells," *Nature,* 327:70–73, 1987.

Kohler and Milstein, "Derivation of specific antibody-producing tissue culture and tumor lines by cell fusion," *Eur. J. Immunol.,* 6(7):511–519, 1976.

Kohler and Milstein, "Continuous cultures of fused cells secreting antibody of predefined specificity," *Nature,* 256 (5517):495–497, 1975.

Kohler, Marks, Wiseman, Jacobs, Davidoff, Clarke-Pearson, Soper, Bast, Berchuck, "Spectrum of mutation and frequency of allelic deletion of the p53 gene in ovarian cancer," *J. Natl. Cancer Inst.,* 85:1513–1519, 1993.

Korn, and Simon, "Measures of explained variation for survival data," *Statistics in Medicine,* 9:487–503, 1990.

Kornblau, Thall, Yang, Estey, Andreeff, "Analysis of CD7 Expression in acute myelogenous leukemia: Martingale residual plots combined with 'optimal' cutpoint analysis reveals absence of prognostic significance," *Leukemia,* 9:1735–1741, 1995.

Kroning, Jones, Hom, Chuang, Sanga, Los, Howell, Christen, "Enhancement of drug sensitivity of human malignancies by epidermal growth factor," *Brit. J. Cancer,* 72(3):615–619, 1995.

Kruk, Maines-Bandiera, Auersperg, "A simplified method to culture human ovarian surface epithelium," *Lab. Invest.,* 63(1):132–136, 1990.

Kuby, "Immunology" 2nd Edition. W.H. Freeman & Company, New York, 1994.

Kunkel, Roberts, Zakour, "Rapid and efficient site-specific mutagenesis without phenotypic selection," *Methods Enzymol.,* 154:367–382, 1987.

Kwoh et al., *Proc. Natl. Acad. Sci, USA,* 86(4):1173–1177, 1989.

Kyte and Doolittle, *J. Mol. Biol.,* 157:105–132, 1982.

L'Huillier, David, Bellamy, "Cytoplasmic delivery of ribozymes leads to efficient reduction in alpha-lactalbumin mRNA levels in C1271 mouse cells," *EMBO J.,* 11(12):4411–4418, 1992.

Le Gal La Salle, Robert, Berrard, Ridoux, Stratford-Perricaudet, Perricaudet, Mallet, "An adenovirus vector for gene transfer into neurons and glia in the brain," Science, 259:988–990, 1993.

Lee et al., "Human retinoblastoma susceptibility gene: cloning, identification, and sequence," *Science,* 235:1394–1399, 1987.

Levrero, Barban, Manteca, Ballay, Balsamo, Avantaggiati, Natoli, Skellekens, Tiollais, Perricaudet, "Defective and nondefective adenovirus vectors for expressing foreign genes in vitro and in vivo," *Gene,* 101:195–202, 1991.

Li, Han, Resnik, Carcangiu, Schwartz, Yang-Feng, "Advanced ovarian carcinoma: molecular evidence of unifocal origin," *Gyn. Onc.,* 51(1):21–5, 1993.

Liang and Pardee, "Differential display of eukaryotic messenger RNA by means of the polymerase chain reaction," *Science,* 257:967–971, 1992.

Lidor, Shpall, Peters, Bast, "Synergistic cytotoxicity of different alkylating agents for epithelial ovarian cancer," *Int. J. Cancer,* 49(5):704–710, 1991.

Lidor, Xu, Martinez-Maza, Olt, Marks, Berchuck, Ramakrishnan, Berek, Bast, "Constitutive production of macrophage colony stimulating factor and interleukin-6 by human ovarian surface epithelial cells," *Exp. Cell Res.,* 207:332–339, 1993.

Lieber, Sandig, Sommer, Bahring, Strauss, "Stable high-level gene expression in mammalian cells by T7 phage RNA polymerase," *Methods Enzymol.,* 217:47–66, 1993.

Lin, "Goodness-of-fit analysis for the Cox regression model based on a class of parameter estimators," *J. American Statistical Association,* 86:725–728. 1991.

Lisziewicz et al., *Proc. Natl. Acad. Sci. USA,* 90:8000–8004, 1993.

Lounis et al., "Primary cultures of normal and tumoral human ovarian epithelium: a powerful tool for basic molecular studies," *Exp. Cell Res.,* 215:303–309, 1994.

Loupart, Armour, Walker, Adams, Brammar, Varley, "Allelic imbalance on chromosome 1 in human breast cancer. I. Ministellite and RFLP analysis," *Genes Chromosomes Cancer,* 12:16–23, 1995.

Lowe and Temple, "Calcitonin and insulin in isobutylcyanoacrylate nanocapsules: protection against proteases and effect on intestinal absorption in rats," 46(7):547–552, 1994.

Lynch, Smyrk, Lynch, "Overview of natural history, pathology, molecular genetics and management of HNPCC (Lynch Syndrome)," Int. J. Cancer, 69(1):38–43, 1996.

Malkin, Li, Strong et al., "Germ line p53 mutations in a familial syndrome of breast cancer, sarcomas, and other neoplasms," *Science,* 250:1233–1238, 1990.

Maloy et al., "Microbial Genetics" 2nd Edition. Jones and Barlett Publishers, Boston, Mass., 1994.

Mann et al., "Construction of a retrovirus packaging mutant and its use to produce helper-free defective retrovirus," *Cell,* 33:153–159, 1983.

Markowitz et al., "A safe packaging line for gene transfer: Separating viral genes on two different plasmids," *J. Virol.,* 62:1120–1124, 1988.

Merrifield B., "Solid phase synthesis," *Science,* 232(4748): 341–347, 1986.

Michael, *Biotechniques,* 16:410–412, 1994.

Michel and Westhof, "Modeling of the three-dimensional architecture of group I catalytic introns based on comparative sequence analysis," *J. Mol. Biol.,* 216:585–610, 1990.

Michieli et al., "Induction of WAF1/CIP1 by a p53-independent pathway," *Cancer Res.,* 54:3391–3395, 1994.

Miki, Swensen, Shattuck-Eidens et al., "A strong candidate for the breast and ovarian cancer susceptibility gene BRCA1," *Science,* 266:66–71, 1994.

Miura, Kaibuchi, Itoh, Corbin, Francis, Takai, "Phosphorylation of smg p21B/Rap1B p21 by cyclic GMP-dependent protein kinase," *FEB. Lett.,* 297:171–174, 1992.

Mok, Tsao, Knapp, Fishbaugh, Lau, "Unifocal origin of advanced human epithelial ovarian cancers," *Cancer Res.,* 52:5119–5122, 1992.

Morishige, Kurachi, Amemiya, Adachi, Inoue, Miyake, Tanizawa, Sakoyama, "Involvement of transforming growth factor alpha/epidermal growth factor receptor autocrine growth mechanism in an ovarian cancer cell line in vitro," *Cancer Res.,* 51(21):5951–5955, 1991.

Moser, Young, Rodriguez, Pizzo, Bast, Stack, "Secretion of extracellular matrix-degrading proteinases is increased in epithelial ovarian carcinomas," *Int J. Cancer,* 56:552–559, 1994.

Mujoo, Maneval, Anderson, Gutterman, "Adenoviral-mediated p53 tumor suppressor gene therapy of human ovarian carcinoma," *Oncogene,* 12(8):1617–1623, 1996.

Nagai, Negrini, Carter, Gillum, Rosenberg, Schwartz, Croce, "Detection and cloning of a common region of loss of heterozygosity at chromosome 1p in breast cancer," *Cancer Res.,* 55:1752–1757, 1995.

Nicolas and Rubenstein, "Retroviral vectors," In: *Vectors: A survey of molecular cloning vectors and their uses,* Rodriguez R L, Denhardt D T, ed., Stoneham: Butterworth, pp. 493–513, 1988.

Nicolau and Sene, "Liposome-mediated DNA transfer in eukaryotic cells," *Biochim. Biophys. Acta,* 721:185–190, 1982.

Nicolau et al., "Liposomes as carriers for in vivo gene transfer and expression," *Methods Enzymol.,* 149:157–176, 1987.

Ohara et al., *Proc. Natl. Acad. Sci. USA,* 86(15):5673–5677, 1989.

Ohara, Dorit, Gilbert, "Direct genomic sequencing of bacterial DNA: the pyruvate kinase I gene of *Escherichia coli,*" *Proc. Natl. Acad. Sci. USA,* 86(18):6883–6887, 1989.

Ohkawa, Yuyama, Taira, "Activities of HIV-RNA targeted ribozymes transcribed from a 'shot-gun' type ribozyme-trimming plasmid," *Nucl. Acids Symp. Ser.,* 27:15–6, 1992.

Ohtani-Fujita, ujita, Aoike, Osifchin, Robbins, Sakai, "CpG methylation inactivates the promoter activity of the human retinoblastoma tumor-suppressor gene," *Oncogene,* 8(4):1063–1067, 1993

Ojwang, Hampel, Looney, Wong-Staal, Rappaport, "Inhibition of human immunodeficiency virus type 1 expression by a hairpin ribozyme," *Proc. Natl. Acad. Sci. USA.,* 89(22):10802–10806, 1992.

Paskind et al., "Dependence of moloney murine leukemia virus production on cell growth," *Virology,* 67:242–248, 1975.

Patton, Jameson, Martin, Altschuler, Bast, Ostrowski, "Activated ras signaling and uPA expression in ovarian carcinoma," *Fifth Meeting on the Molecular Basis of Cancer,* Hood College, Frederick, Md., 1994.

Pease et al., Light-generated oligonucleotide arrays for rapid DNA sequence analysis," *Proc. Natl. Acad. Sci. USA,* 91(11):5022–5026, 1994.

Pelletier and Sonenberg, "Internal initiation of translation of eukaryotic mRNA directed by a sequence derived from poliovirus RNA," *Nature,* 334(6180):320–325, 1988.

Perales, Ferkol, Beegen, Ratnoff, Hanson, "Gene transfer in vivo: sustained expression and regulation of genes introduced into the liver by receptor-targeted uptake," *Proc. Natl. Acad. USA,* 91(9):4086–4090, 1994.

Perreault, Wu, Cousinequ, Ogilvie, Cedergren, "Mixed deoxyribo- and ribo-oligonucleotides with catalytic activity," *Nature,* 344(6266):565, 1990.

Perrotta and Been, "Cleavage of oligoribonucleotides by a ribozyme derived from the hepatitis delta virus RNA sequence," *Biochem.,* 31(1):16, 1992.

Pieken, Olsen, Benseler, Aurup, Eckstein, "Kinetic characterization of ribonuclease-resistant 2'-modified hammerhead ribozymes," *Science,* 253(5017):314, 1991.

Pignon et al., "Exhaustive analysis of the P53 gene coding sequence by denaturing gradient gel electrophoresis: application to the detection of point mutations in acute leukemias," *Hum. Mutat.,* 3(2):126–132, 1994.

Pizon, Chardin, Lerosey, Olofsson, Tavitian, "Human cDNAs Rap1 and Rap2 homologous to the *Drosophila* gene DRas3 encode proteins closely related to Ras in the 'effector' region," *Oncogene,* 3:210–204, 1988.

Potter et al., "Enhancer-dependent expression of human k immunoglobulin genes introduced into mouse pre-B lymphocytes by electroporation," *Proc. Nat. Acad. Sci. USA,* 81:7161–7165, 1984.

Pregibon, "Resistant fits for some commonly used logistic models with medical applications," *Biometrics,* 38:485–498, 1982.

Prokop and Bajpai, *Ann. N.Y. Acad. Sci.,* Vol. 646, 1991.

Quilliam, Mueller, Bohl, Prossnitz, Sklar, Der, Bokoch, "Rap1A is a substrate for cyclic AMP-dependent protein kinase in human neutrophils," *J. Immunol.,* 147:1628–1635, 1991.

Ragot, Vincent, Chafey, Vigne, Gilgenkrantz, Couton, Cartaud, Briand, Kaplan, Perricaudet, Kahn, "Efficient adenovirus-mediated transfer of a human minidystrophin gene to skeletal muscle of mdx mice," *Nature* 361:647–650, 1993.

Reinhold-Hurek and Shub, "Self-splicing introns in tRNA genes of widely divergent bacteria," *Nature*, 357:173–176, 1992.

Rich et al., "Development and analysis of recombinant adenoviruses for gene therapy of cystic fibrosis," *Hum. Gene Ther.*, 4(4):461–476, 1993.

Ridgeway, "Mammalian expression vectors," In: *Vectors: A survey of molecular cloning vectors and their uses*, Rodriguez R L, Denhardt D T, ed., Stoneham: Butterworth, pp. 467–492, 1988.

Rippe et al., "DNA-mediated gene transfer into adult rat hepatocytes in primary culture," *Mol. Cell Biol.*, 10:689–695, 1990.

Rodriguez, Berchuck, Whitaker, Schlossman, Clarke-Pearson, Bast, "Epidermal growth factor receptor expression in normal ovarian epithelium and ovarian cancer. II. Relationship between receptor expression and response to epidermal growth factor" *Am. J. Obstet. Gynecol.*, 164: 745–750, 1991.

Rosenfeld, Yoshimura, Trapnell, Yoneyama, Rosenthal, Dalemans, Fukayama, Bargon, Stier, Stratford-Perricaudet, Perricaudet, Guggino, Pavirani, Lecocq, Crystal, "In vivo transfer of the human cystic fibrosis transmembrane conductance regulator gene to the airway epithelium," *Cell*, 68:143–155, 1992.

Rosenfeld, Siegfried, Yoshimura, Yoneyama, Fukayama, Stier, Paakko, Gilardi, Stratford-Perricaudet, Perricaudet, Jallat, Pavirani, Lecocq, Crystal, "Adenovirus-mediated transfer of a recombinant ∀1-antitrypsin gene to the lung epithelium in vivo," *Science*, 252:431–434, 1991.

Rossi, Elkins, Zaia, Sullivan, "Ribozymes as anti-HIV-1 therapeutic agents: principles, applications, and problems," *AIDS Res. Hum. Retrovir.*, 8(2): 183, 1992.

Roux et al., "A versatile and potentially general approach to the targeting of specific cell types by retroviruses: Application to the infection of human cells by means of major histocompatibility complex class I and class II antigens by mouse ecotropic murine leukemia virus-derived viruses," *Proc. Natl. Acad. Sci. USA*, 86:9079–9083, 1989.

Rubin, Finstad, Wong et al, "Prognostic significance of HER-2/neu expression in advanced ovarian cancer," *Am. J. Obstet. Gynecol.*, 168:162–169, 1993.

Sahyoun, McDonald, Farrell, Lapetina, "Phosphorylation of a Ras-related GTP-binding protein, Rap-1b, by a neuronal Ca2+/calmodulin-dependent protein kinase, CaM kinase Gr," *Proc. Natl. Acad. Sci. USA*, 88:2643–2647, 1991.

Sakoda, Kaibuchi, Kishi, Kishida, Doi, Hoshino, Hattori, Takai, "smg/Rap1/Krev-1/p21s inhibit the signal pathway to the c-fos promoter/enhancer from c-Ki-Ras p21 but not from c-raf-1 kinase in NIH3T3 cells," *Oncogene*, 7:1705–1711, 1992.

Sambrook et al., "Molecular Cloning: A Laboratory Manual," Cold Spring Harbor Laboratory, Cold Spring Harbor, N.Y., 1989.

Sarver, Cantin, Chang, Zaia, Ladne, Stephens, Rossi, "Ribozymes as a potential anti-HIV-1 therapeutic agents," *Science*, 247(4947):1222–1225, 1990.

Saville and Collins, "A site-specific self-cleavage reaction performed by a novel RNA in *Neurospora* mitochondria," *Cell*, 61(4):685–696, 1990.

Saville and Collins, "RNA-mediated ligation of self-cleavage products of a *Neurospora* mitochondrial plasmid transcript," *Proc. Natl. Acad. Sci. USA*, 88(19):8826–8830, 1991.

Scanlon, Jiao, Funato, Wang, Tone, Rossi, Kashani-Sabet, "Ribozyme-mediated cleavage of c-fos mRNA reduces gene expression of DNA synthesis enzymes and metallothionein,", *Proc. Natl. Acad. Sci. USA*, 88(23):10591–10595, 1991.

Scaringe, Francklyn, Usman, "Chemical synthesis of biologically active oligoribonucleotides using beta-cyanoethyl protected ribonucleoside phosphoramidites," *Nucl. Acids Res.*, 18(18):5433–5441, 1990.

Schemper and Stare, "Explained Variation in Survival Analysis," *Statistics in Medicine*, 15:1999–2012, 1996.

Segal, "Biochemical Calculations," 2nd Edition, John Wiley & Sons, New York, 1976.

Shultz, Schwaitzer, Rajan, Yi, Ihle, Mathews, Thomas, Beier, "Mutations at the murine motheaten locus are within the hematopoietic cell protein-tyrosine phosphatase (Hcph) gene," *Cell*, 73(7):1445–54, 1993.

Stampfer, "Isolation and growth of human mammary epithelial cells," *J. Tissue Culture Methods*, 9:107–115, 1985.

Steel and Peckham, "Exploitable mechanisms in combined ratiotherapy-chemotherapy: The concept of additivity," *Int. J. Radiation Oncol. Biol. Phys.*, 5:85–91, 1979.

Stewart et al., "Immunochemical studies on tobacco mosaic virus protein. IV. The automated solid-phase synthesis of a decapeptide of tobacco mosaic virus protein and its reaction with antibodies to the whole protein," *Biochemistry*, 5(11):3396–3400, 1966.

Stratford-Perricaudet and Perricaudet, "Gene transfer into animals: the promise of adenovirus," *p.* 51–61, In: *Human Gene Transfer*, Eds, O. Cohen-Haguenauer and M. Boiron, Editions John Libbey Eurotext, France, 1991.

Stratford-Perricaudet et al., "Evaluation of the transfer and expression in mice of an enzyme-encoding gene using a human adenovirus vector," *Hum. Gene Ther.*, 1:241–256, 1990.

Stromberg, Collins, Gordon, Jackson, Johnson, "Transforming growth factor-alpha acts as an autocrine growth factor in ovarian carcinoma cell lines," *Cancer Res.*, 52(2): 341–347, 1992.

Symmans, Liu, Knowles, Inghirami, "Breast cancer heterogeneity: evaluation of clonality in primary and metastatic lesions," *Hum. Path.*, 26:210–216, 1995.

Taira, Nakagawa, Nishikawa, Furukawa, "Construction of a novel RNA-transcript-trimming plasmid which can be used both in vitro in place of run-off and (G)-free transcriptions and in vivo as multi-sequences transcription vectors," *Nucl. Acids Res.*, 19(19):5125–5130, 1991.

Temin, "Retrovirus vectors for gene transfer: Efficient integration into and expression of exogenous DNA in vertebrate cell genome," In: *Gene transfer*, Kucherlapati R, ed., New York: Plenum Press, pp. 149–188, 1986.

Therneau, "A Package for Survival Analysis in S," *Mayo Foundation*, 1994.

Therneau, Grambsch, Fleming, "Martingale-based Residuals for Survival Models," *Biometrika*, 77:147–160, 1990.

Tomic, Sunjevaric, Savtchenko, Blumenberg, "A rapid and simple method for introducing specific mutations into any position of DNA leaving all other positions unaltered," *Nucl. Acids Res.*, 18(6):1656, 1990.

Top et al., "Immunization with live types 7 and 4 adenovirus vaccines. II. Antibody response and protective effect against acute respiratory disease due to adenovirus type 7," *J. Infect. Dis.*, 124:155–160, 1971.

Tornaletti and Pfeifer, "Complete and tissue-independent methylation of CpG sites in the p53 gene: implications for mutations in human cancers," *Oncogene* 10(8):1493–1499, 1995.

Tur-Kaspa et al., "Use of electroporation to introduce biologically active foreign genes into primary rat hepatocytes," *Mol. Cell Biol.*, 6(2):716–718, 1986.

Upender, Raj, Weir, "Megaprimer method for in vitro mutagenesis using parallel templates," *Biotechniques*, 18:29–31, 1995.

Usman and Cedergren, "Exploiting the chemical synthesis of RNA," *Trends in Biochem. Sci.*, 17(9):334, 1992.

Usman et al., *J. Am. Chem. Soc.*, 109:7845–7854, 1987.

Varmus et al., "Retroviruses as mutagens: Insertion and excision of a nontransforming provirus alter the expression of a resident transforming provirus," *Cell*, 25:23–36, 1981.

Venables, Ripley, Springer-Verlag, "Modern Applied Statistics With S-Plus," New York, 1994.

Ventura, Wang, Ragot, Perricaudet, Saragosti, *Nucl. Acids Res.*, 21(14):3249–3255, 1993.

Voss et al., "Synthesis of the protected tridecapeptide (56–68) of the VH domain of mouse myeloma immunoglobulin M603 and its reattachment to resin supports," *Int J. Pept. Protein Res.*, 22(2):204–213, 1983.

Wagner, Zenke, Cotten, Beug, Birnstiel, "Transferrin-polycation conjugates as carriers for DNA uptake into cells," *Proc. Natl. Acad. Sci. USA*, 87:3410–3414, 1990.

Walker, Little, Nadeau, Shank, "Isothermal in vitro amplification of DNA by a restriction enzyme/DNA polymerase system," *Proc. Natl. Acad. Sci. USA*, 89(1):392–396, 1992.

Watson, et al., *Molecular Biology of the Gene*, 4th Ed., W. A. Benjamin, Inc., Menlo Park, Calif., 1987.

Weerasinghe, Liem, Asad, Read, Joshi, "Resistance to human immunodeficiency virus type 1 (HIV-1) infection in human CD4+ lymphocyte-derived cell lines conferred by using retroviral vectors expression an HIV-1 RNA-specific ribozyme," *J. Virol.*, 65(10):5531–5534, 1991.

Weinberg, "Positive and negative controls on cell growth," *Biochemistry*, 28:8263–8269, 1989.

Wiener, Hurteau, Kems, Whitaker, Conaway, Wu, Berchuck, Bast, "Overexpression of the tyrosine phosphatase PTP1B is associated with human ovarian carcinomas," *Am. J. Obstet. Gynecol.*, 170:1177–1183, 1994.

Wiener, Kassim, Yu, Mills, Bast, "Transfection of human ovarian cancer cells with the HER-2/neu receptor tyrosine kinase induces a selective increase in PTP-H1, PTP-1B, and PTP-expression," *Gynecol. Oncol.*, 61:223–240, 1996.

Wolf et al., "An Integrated Family of Amino Acid Sequence Analysis Programs," *Compu. Appl. Biosci.*, 4(1):187–191, 1988.

Wolf, Bazelle, Mills, Bast, Roth, Gershenson, "Growth inhibition of human ovarian cancer cells by transfection with adenovirus-mediated p53 is independent of endogenous p53 status," *Proc. Amer. Assoc. Cancer Res.*, 37:205(A#1399), 1996.

Wong et al., "Appearance of β-lactamase activity in animal cells upon liposome mediated gene transfer," *Gene*, 10:87–94, 1980.

Woolf, Melton, Jennings, *Proc. Natl. Acad. Sci. USA*, 89(16):7305–7309, 1992.

Wooster, Neuhausen, Mangion et al., "Localization of a breast cancer susceptibility gene, BRCA2, to chromosome 13q12–13," *Science*, 265:2088–2090, 1994.

Worsley, Ponder, Davies, "Overexpression of cyclin D1 in epithelial ovarian cancers," *Gynecol. Oncol.*, 64:189–195, 1997.

Wu and Wang, "Sequence-selective DNA binding to the regulatory subunit of cAMP-dependent protein kinase," *J. Biol. Chem.*, 264(17):9989–9993, 1989.

Wu and Wu, "Evidence for targeted gene delivery to HepG2 hepatoma cells in vitro," *Biochemistry*, 27:887–892, 1988.

Wu and Wu, "Receptor-mediated in vitro gene transfections by a soluble DNA carrier system," *J. Biol. Chem.*, 262:4429–4432, 1987.

Wu and Wu, Adv. Drug Delivery Rev., 12:159–167, 1993.

Wu, Rodabaugh, Martinez-Maza, Watson, Silberstein, Boyer, Peters, Weinberg, Berek, Bast, "Stimulation of ovarian tumor cell proliferation with monocyte products including interleukin-1, interleukin-6, and tumor necrosis factor-alpha," *Am. J. Obstet. Gynecol.*, 166:997–1007, 1992.

Wu and Dean, "Functional significance of loops in the receptor binding domain of *Bacillus thuringiensis* CryIIIA δ-endotoxin," *J. Mol. Biol.*, 255(4):628–640, 1996.

Xiong et al., "p21 is a universal inhibitor of cyclin kinases," *Nature,* 366:701–704, 1993.

Xu et al., "Development of two new monoclonal antibodies reactive to a surface antigen present on human ovarian epithelial cancer cells," *Cancer Res.,* 51:4012–4019, 1991.

Xu, Fang, Gaudette, Holub, Casey, Mills, "Lysophospholipids activate ovarian and breast cancer cells," *Biochem. J,* 309:933–940. 1995.

Xu, Ramakrishnan, Daly, Soper, Berchuck, Clarke-Pearson, Bast, "Increased serum levels of macrophage colony-stimulating factor in ovarian cancer," *Am. J. Obstet. Gynecol.,* 165:1356–1362, 1991.

Xu, Rodriguez, Bae, Whitaker, Boyer, Mills, Yu, Bast, "Heregulin and anti-p185c-erb$^{B-2}$ antibodies inhibit proliferation, increase invasiveness and enhance tyrosine autophosphorylation of breast cancer cells that overexpress p185c-erb$^{B-2}$," *Proc. Amer. Assoc. Cancer Res.,* 35:38(A#225), 1994.

Xu, Yu, Boyer, Walch, Khan, Mills, Bast, "Stimulation or inhibition of ovarian cancer cell proliferation by heregulin is dependent on the ratio of HER2 to HER3 or HER4 expression," *Proc. Amer. Assoc. Cancer Res.,* 37:191 (A#1305), 1996.

Yang et al., "In vivo and in vitro gene transfer to mammalian somatic cells by particle bombardment," *Proc. Natl. Acad. Sci. USA,* 87:9568–9572, 1990.

Yatani, Quilliam, Brown, Bokoch, "Rap1A antagonizes the ability of Ras and Ras-Gap to inhibit muscarinic K+ channels," *J. Biol. Chem.,* 266:22222–22226, 1991.

Young, Rodriguez, Moser, Bast, Pizzo, Stack, "Coordinate expression of urinary-type plasminogen activator and its receptor accompanies malignant transformation of the ovarian surface epithelium," *Am. J. Obstet. Gynecol.,* 170:1285–1296, 1994.

Young, Rodriguez, Rinehart, Bast, Pizzo, Stack, "Characterization of gelatinases linked to extracellular matrix invasion in ovarian adenocarcinoma: purification of matrix metalloproteinase 2," *Gyn. Oncol.,* 62:89–99, 1996.

Yu and Chang, "Submicron polymer membrane hemoglobin nanocapsules as potential blood substitutes: preparation and characterization," *Artif Cells Blood Substit. Immobil. Biotechnol.,* 24(3): 169–183, 1996.

Yu, Ojwang, Yamada, Hampel, Rapapport, Looney, Wong-Staal, "A hairpin ribozyme inhibits expression of diverse strains of human immunodeficiency virus type 1," *Proc. Natl. Acad. Sci. USA,* 90:6340–6344, 1993.

Yu, Henry, Xu, Hamilton, "Expression of a murine cytomegalovirus early and late protein in latently infected mice," *J. Infectious Diseases,* 172:371–379, 1995a.

Yu, Matin, Xia, Sorgi, Huang, Hung, "Liposome-mediated in vivo E1A gene transfer suppressed dissemination of ovarian cancer cells that overexpress HER-2/neu," Oncogene, 11(7):1383–1388, 1995b.

Zelenin et al., "High-velocity mechanical DNA transfer of the chloramphenicol acetyltransferase gene into rodent liver, kidney and mammary gland cells in organ explants and in vivo," *FEBS Lett.,* 280:94–96, 1991.

Zhang, Calaf, Russo, "Allele loss and point mutation in codons 12 and 61 of the c-Ha-ras oncogene in carcinogen-transformed human breast epithelial cells," *Mol. Carcin.,* 9:46–56, 1994.

Zhou, Giordano, Durbin, McAllister, *Mol. Cell Biol.,* 10(9): 4529–4537, 1990.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

What is claimed is:

1. An isolated or purified polynucleotide that encodes the amino acid sequence of SEQ ID NO:2, or the complete complement of such a polynucleotide.

2. The polynucleotide of claim 1, further defined as comprising the nucleic acid sequence of from position 150 to position 833 of SEQ ID NO:1 or the nucleic acid sequence of SEQ ID NO:5.

3. The polynucleotide of claim 1, further defined as a sequence complementary to the nucleic acid sequence of from position 150 to position 833 of SEQ ID NO:1 or the nucleic acid sequence of SEQ ID NO:5.

4. The polynucleotide of claim 1, wherein said polynucleotide is operably linked to a promoter.

5. The polynucleotide of claim 1, comprised within a vector.

6. The polynucleotide of claim 5, wherein said vector is a plasmid, cosmid, phagemid, virus, baculovirus, yeast artificial chromosome, bacterial artificial chromosome or phage.

7. The polynucleotide of claim 6, wherein said virus is an adenovirus, an adenoassociated virus, a retrovirus, a Herpes virus, or a vaccinia virus.

8. A host cell comprising the polynucleotide selected from the group consisting of the polynucleotides of any one of claims 1–3 and 4–7.

9. The host cell of claim 8, further defined as a bacterial cell.

10. The host cell of claim 9, wherein said bacterial cell is an E. coli, Pseudomonas sp. or salmonella cell.

11. The host cell of claim 8, further defined as a eukaryotic cell.

12. The host cell of claim 11, further defined as an animal cell, a yeast cell, or a fungal cell.

13. The host cell of claim 12, wherein said animal cell is a human, mouse, rat, monkey, chicken, dog, cat, horse, pig, cow, sheep, goat or hamster cell.

14. The host cell of claim 12, wherein said animal cell is a tumor cell.

15. The host cell of claim 14, wherein said tumor cell is an ovarian cancer or breast tumor cell.

16. The host cell of claim 8, wherein said polynucleotide is introduced into said cell by means of a vector.

17. The host cell of claim 16, wherein said host cell expresses said polynucleotide to produce a tumor suppressor polypeptide.

18. A method of preparing a polypeptide, comprising the steps of:
    (a) providing a polynucleotide in accordance with claim 5;
    (b) introducing said vector into a host cell;
    (c) culturing said host cell under conditions effective to allow expression of the encoded polypeptide; and
    (d) collecting the polypeptide so expressed.

19. An isolated polynucleotide fragment of SEQ ID NO:1 or SEQ ID NO:5 comprising at least 100 continuous nucleotides thereof.

20. The isolated polynucleotide fragment of claim 19, further defined as a polynucleotide fragment of SEQ ID NO:1 or SEQ ID NO:5 comprising at least 200 contiguous nucleotides thereof.

21. A nucleic acid detection kit comprising, in suitable container means, the polynucleotide fragment selected from the group consisting of the polynucleotide fragments of claims 19–20, and a detection reagent.

22. A recombinant vector comprising the nucleotide fragment of claim 19.

23. The recombinant vector of claim 22, further defined as comprising the nucleotide fragment of claim 20.

* * * * *

UNITED STATES PATENT AND TRADEMARK OFFICE
CERTIFICATE OF CORRECTION

PATENT NO.         : 7,183,401 B1                                           Page 1 of 1
APPLICATION NO. : 10/166325
DATED              : February 27, 2007
INVENTOR(S)        : Yu et al.

It is certified that error appears in the above-identified patent and that said Letters Patent is hereby corrected as shown below:

In claim 5, column 119, line 46, after "claim 1", insert --or any one of claims 19-20-- therefor.

Signed and Sealed this

Thirteenth Day of November, 2007

JON W. DUDAS
*Director of the United States Patent and Trademark Office*